(12) United States Patent
Garlich et al.

(10) Patent No.: US 6,949,537 B2
(45) Date of Patent: Sep. 27, 2005

(54) PI-3 KINASE INHIBITOR PRODRUGS

(75) Inventors: Joseph R. Garlich, Westfield, IN (US);
Donald L. Durden, Decatur, GA (US);
Mary Patterson, Carmel, IN (US);
Jingdong Su, Westfield, IN (US);
Robert G. Suhr, Greenfield, IN (US)

(73) Assignee: Semafore Pharmaceuticals, Inc., Indianapolis, IN (US)

(*) Notice: Subject to any disclaimer, the term of this patent is extended or adjusted under 35 U.S.C. 154(b) by 0 days.

(21) Appl. No.: 10/818,145

(22) Filed: Apr. 5, 2004

(65) Prior Publication Data

US 2004/0242631 A1 Dec. 2, 2004

Related U.S. Application Data

(60) Provisional application No. 60/460,137, filed on Apr. 3, 2003.

(51) Int. Cl.[7] .................. A61K 31/535; A61K 31/418; C07D 311/76; C07D 268/30; C07C 381/00
(52) U.S. Cl. .................. 514/183; 514/232.5; 514/320; 514/392; 514/429; 514/453; 514/459; 540/450; 540/467; 544/150; 544/151; 546/196; 548/229; 548/528; 549/315; 549/347; 549/383; 549/401; 549/403; 558/13; 424/1.21; 424/450
(58) Field of Search ................. 549/403, 401, 549/383, 347, 315; 544/151, 150; 546/196; 548/229, 525; 514/232.5, 320, 392, 429, 183; 558/453, 459, 13; 540/450, 467

(56) References Cited

U.S. PATENT DOCUMENTS 3,937,719 A * 2/1976 Sellstedt et al. ............ 549/401
5,116,954 A * 5/1992 Briet et al. .................. 534/551

FOREIGN PATENT DOCUMENTS

WO WO 91/19707 12/1991
WO WO 01/53266 A1 7/2001
WO WO 03/024949 A1 3/2003

OTHER PUBLICATIONS

Bantick, J., et al., "Synthesis of 2–Aminochromones, Studies on the Nucleophilic Displacement of Sulphinyl and Sulphonyl Groups in the 2–Position of 5,8–Dimethoxychromone," J. Het. Chem., vol. 18, pp. 679–684 (1981).

Chiosis, G., et al., "LY294002–Geldanamycin Heterodimers as Selective Inhibitors of the PI3K and PI3K–related Family," Bioorganic & Medicinal Chemistry Letters, vol. 11, pp. 909–913 (2001).

Vlahos, C., et al., "A Specific Inhibitor of Phosphatidylinositol 3–Kinase, 2–(4–Morpholinyl)–8–phenyl–4H–1–benzopyran–4–one (LY294002)" Journal of Biological Chemistry, vol. 269, No. 7, pp. 5241–5248 (1994).

Walker, E., et al., "Structural Determinants of Phosphoinositide 3–Kinase Inhibition by Wortmannin, LY294002, Quercetin, Myricetin, and Staurosporine," Molecular Cell, vol. 6, pp. 909–919 (2000).

Wermuth, C., et al., "Designing Prodrugs and Bioprecursors I: Carrier Prodrugs," The Practice of Medicinal Chemistry, Academic Press Limited, pp. 671–696 (1996).

PCT International Search Report for PCT/US2004/010399 dated Aug. 12, 2004.

* cited by examiner

Primary Examiner—Cecilia J. Tsang
Assistant Examiner—Raymond Covington
(74) Attorney, Agent, or Firm—Howrey LLP; David W. Clough; Teddy C. Scott, Jr.

(57) ABSTRACT

The invention provides novel prodrugs of inhibitors of PI-3 kinase. The novel compounds are LY294002 and analogs thereof comprising a reversibly quaternized amine.

20 Claims, 8 Drawing Sheets

Inhibition of Phagocytosis by LY294002

UV 254 Chromatogram CC1126 (A036-33)

ELS Chromatogram CC1126 (A036-33)

A. Control   B. RADfV   C. RGDfV
D. RGDS     E. CC1101  F. CC1126
(All at 20 uM)

PI-3 KINASE INHIBITOR PRODRUGS

CROSS REFERENCE TO RELATED APPLICATIONS

This application claims priority to U.S. Provisional Application No. 60/460,137, filed Apr. 3, 2003.

BACKGROUND OF THE INVENTION

1. Field of the Invention

The present invention relates to prodrugs of PI-Kinase inhibitors and methods of using these inhibitors.

2. Description of Related Art

PI-3 kinases are a large family of lipid kinases that phosphorylate phosphatidylinositol in the D3 position to generate an important second messenger, phosphatidylinositol 3'-phosphate. Members of the PI-3 kinase family are divided into 3 classes based on sequence homology and the product formed by enzyme catalysis. The class I PI-3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, which suggests that control of this pathway may lead to important therapeutic effects.

Inhibition of class I PI-3 kinase induces apoptosis, blocks tumor induced angiogenesis in vivo, and increases the radiosensitivity of certain tumors. LY294002 (2-(4-morpholinyl)-8-phenyl-4H-1-benzopyran-4-one) (Compound 1) is a well known specific inhibitor of class I PI-3 kinases and has been demonstrated to possess anti-cancer properties.

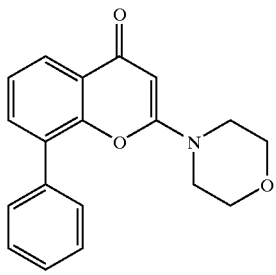

(Compound 1)

However, the anti-cancer applications of LY294002 are severely limited by its lack of aqueous solubility and its poor pharmacokinetics. Moreover, LY294002 has no tissue specific properties and has been demonstrated to be rapidly metabolized in animals. Because of these factors, LY294002 would need to be administered at frequent intervals and thus has the potential to also inhibit PI-3 kinases in normal cells thereby leading to undesirable side effects.

There continues to be a need for class I PI-3 kinase inhibitors with improved pharmacokinetic and pharmacodynamic properties. The present invention fulfills these needs and provides other related advantages.

SUMMARY OF THE INVENTION

The present invention is related to pro-compounds comprising a quaternary nitrogen, wherein one bond of the quaternary nitrogen is hydrolyzable and after hydrolysis of said bond yields a compound of the formula:

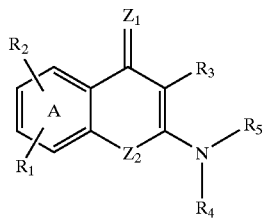

wherein, $R_1$ and $R_2$ independently are H, optionally substituted aliphatic, optionally substituted aryl, hydroxyl, halogen, alkoxy, heterocycle, cyano, amino, or, are taken together to form an optionally substituted cycloaliphatic or optionally substituted aryl;

$R_3$ represents H, optionally substituted aliphatic, and optionally substituted aryl; and $R_4$ and $R_5$ independently are H, optionally substituted aliphatic, optionally substituted aryl, heterocycle, aryloxy, carboxy, or, are taken together to form an optionally substituted heterocycle or optionally substituted heteroaryl.

The pro-compound may be of the formula:

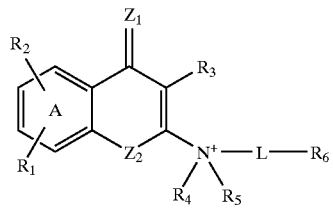

wherein,

Ring A is benzo;

$Z_1$ and $Z_2$ independently are S or O;

$R_1$ and $R_2$ independently are H, optionally substituted aliphatic, optionally substituted aryl, hydroxyl, halogen, alkoxy, heterocycle, cyano, amino, or, are taken together to form an optionally substituted cycloaliphatic or optionally substituted aryl;

$R_3$ represents H, optionally substituted aliphatic, and optionally substituted aryl;

$R_4$ and $R_5$ independently are H, optionally substituted aliphatic, optionally substituted aryl, heterocycle, aryloxy, carboxy, or, are taken together to form an optionally substituted heterocycle or optionally substituted heteroaryl;

$R_6$ represents H, optionally substituted aliphatic, optionally substituted aryl, alkoxy, carboxy, amino, heterocycle, aryloxy, and optionally substituted therewith a targeting agent; and L represent a linker group.

The targeting agent may be a vitamin, peptide, protein, liposome, bone-seeking agent or cartilage-seeking agent The present invention is also related to intermediate compounds of the formula:

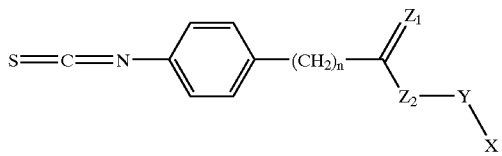

wherein,
X represents a halo group, preferably Cl or I;
Y represents —$CH_2$—, —$CH(CH_3)$—, —CH(Ph)-, —$C(CH_3)(COOH)$— or CH(CH($CH3$)2)—;
$Z_1$ and $Z_2$ independently are S or O; and
n=0 to 1.

The present invention is also related to the use of the pro-compounds for the treatment of a condition associated with PI-3 kinase activity, inflammatory disease, age-related macular degeneration, conditions associates with a mutant PTEN, hypertension, pancreatitis, ulcers, cancer; disrupting leukocyte function; inducing apoptosis; enhancing the chemosensitivity of tumor cells; enhancing the radiosensitivity of tumor cells; inhibiting tumor induced angiogenesis; inhibiting angiogenic processes associated with non-cancer diseases; improving performance of a stent; inhibiting phosphatidylinositol 3-kinase in a whole cell of a patient, comprising administering to a patient in need thereof an effective amount of a composition comprising the pro-compounds of the present invention. The pro-compounds may be administered to the patient by slow I.V. fusion.

The present invention is also related to a method for suppressing differentiation of progenitor cells comprising contacting progenitor cells with an effective amount of a composition comprising a pro-compound of the present invention.

The present invention is also related to the purification of the pro-compounds of the present invention comprising adding the pro-compounds to a solution comprising at least 0.1% (v/v) acid. The solution comprising the pro-compound is the chromatographed, preferably by HPLC, to isolate the pro-compound.

DETAILED DESCRIPTION

Figure 1:
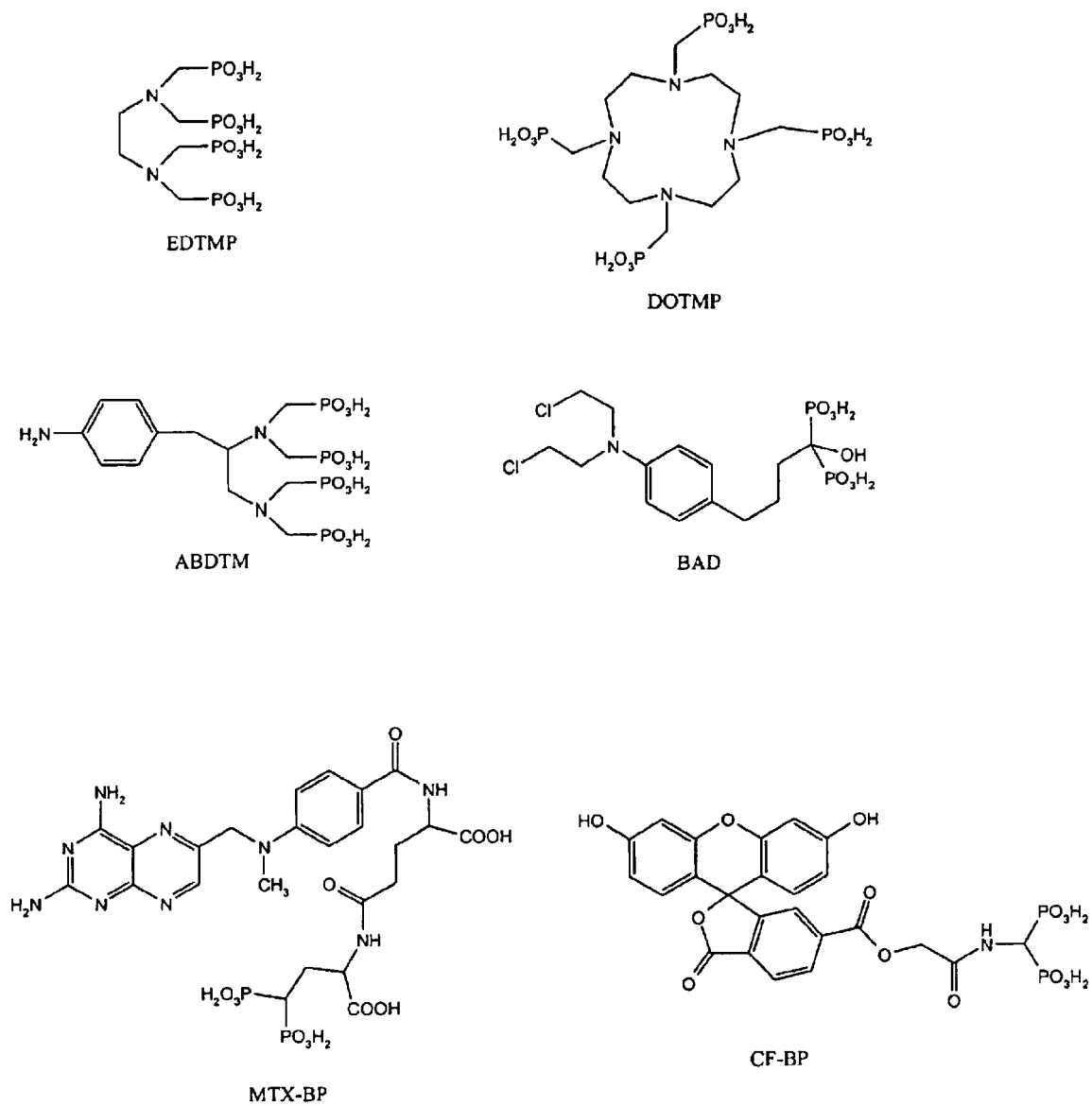
FIG. 1 shows the chemical structure of EDTMP, DOTMP, ABDTMP, BAD, MTX-BP and CF-BP.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

1. Definitions

The term "branched" as used herein refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, —$CH_2CH_2CH(CH3)CH_2CH_3$, —$CH_2CH(CH_2CH_3)CH_2CH_3$, —$CH_2CH_2C(CH_3)_2CH_3$, —$CH_2CH_2C(CH_3)_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, —$CH_2CH_2CH=CH_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group having 4n+2 delocalized π(pi) electrons, which may be substituted or unsubstituted. The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents.

An atom with two substituents is denoted with "di," whereas an atom with more than two substituents is denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

The term "unsubstituted" as used herein refers to a group that does not have any further groups attached thereto or substituted therefor.

The term "alkyl" as used herein alone or in combination refers to a branched or unbranched, saturated aliphatic group. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like.

The term "alkenyl" as used herein alone or in combination refers to a branched or unbranched, unsaturated aliphatic group containing at least one carbon-carbon double bond which may occur at any stable point along the chain. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Representative examples of aryl groups include, but are not limited to, phenyl, benzyl, naphthyl, benzylidine, xylyl, styrene, styryl, phenethyl, phenylene, benzenetriyl and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The term "halogen," "halide" or "halo" as used herein alone or in combination refers to fluorine "F", chlorine "Cl", bromine "Br", iodine "I", and astatine "At". Representative examples of halo groups include, but are not limited to, chloroacetamido, bromoacetamido, idoacetamido and the like.

The term "hetero" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" as used herein refers to a cyclic group containing a heteroatom. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "acryl" as used herein alone or in combination refers to a group represented by $CH_2=C(O)C(O)O—$ where Q is an aliphatic or aromatic group.

The term "cyano," "cyanate," or "cyanide" as used herein alone or in combination refers to a carbon-nitrogren double bond. Representative examples of cyano groups include, but are not limited to, isocyanate, isothiocyanate and the like.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and alkyl where there is a substitution.

The term "effective amount," when used in reference to a compound, product, or composition as provided herein, means a sufficient amount of the compound, product or composition to provide the desired result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

The term "suitable" as used herein refers to a group that is compatible with the compounds, products, or compositions as provided herein for the stated purpose. Suitability for the stated purpose may be determined by one of ordinary skill in the art using only routine experimentation.

The term "hydrolyzable" as used herein refers to whether the group is capable of or prone to hydrolysis (i.e., splitting of the molecule or group into two or more new molecules or group).

2. Compounds

The present invention provides a compound, which upon cleavage of one bond of a quaternary amine yields a compound of the formula:

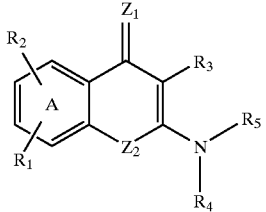

(Compound 2)

wherein,
Ring A is benzo;
$Z_1$ and $Z_2$ independently are S or O;
$R_1$ and $R_2$ independently are H, optionally substituted aliphatic, optionally substituted aryl, hydroxyl, halogen, alkoxy, heterocycle, cyano, amino, or, are taken together to form an optionally substituted cycloaliphatic or optionally substituted aryl,;
$R_3$ represents H, optionally substituted aliphatic, and optionally substituted aryl; and
$R_4$ and $R_5$ independently are H, optionally substituted aliphatic, optionally substituted aryl, heterocycle, aryloxy, carboxy, or, are taken together to form an optionally substituted heterocycle or optionally substituted heteroaryl.

Preferably, cleavage of one bond of a quaternary amine yields LY294002 (Compound 1).

The present invention also provides a compound of the formula:

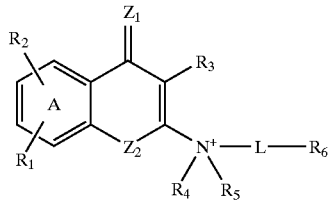

(Compound 3)

wherein,
Ring A is benzo;
$Z_1$ and $Z_2$ independently are S or O;
$R_1$ and $R_2$ independently are H, optionally substituted aliphatic, optionally substituted aryl, hydroxyl, halogen, alkoxy, heterocycle, cyano, amino, or, are taken together to form an optionally substituted cycloaliphatic or optionally substituted aryl;
$R_3$ represents H, optionally substituted aliphatic, and optionally substituted aryl;

$R_4$ and $R_5$ independently are H, optionally substituted aliphatic, optionally substituted aryl, heterocycle, aryloxy, carboxy, or, are taken together to form an optionally substituted heterocycle or optionally substituted heteroaryl; and $R_6$ represents H, optionally substituted aliphatic, optionally substituted aryl, alkoxy, carboxy, amino, heterocycle, aryloxy, and optionally substituted therewith a targeting agent; and L represents a linker group.

In a preferred embodiment, Compounds 2–3 of the present invention are those compounds wherein, $R_1$-Ring A-$R_2$ is selected from the group consisting of the following:

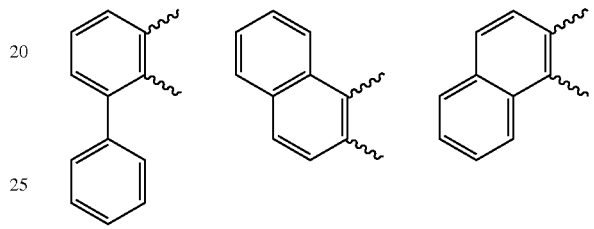

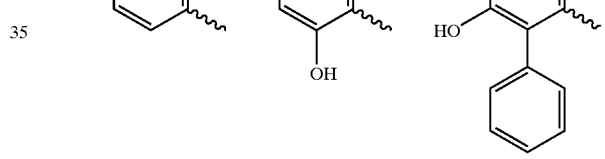

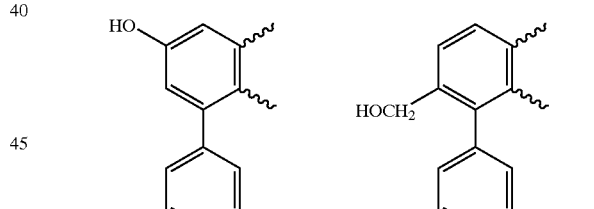

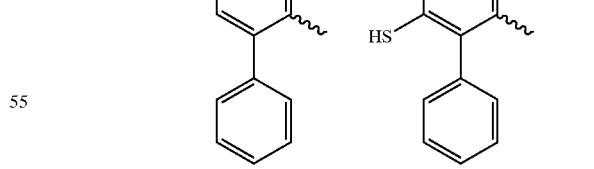

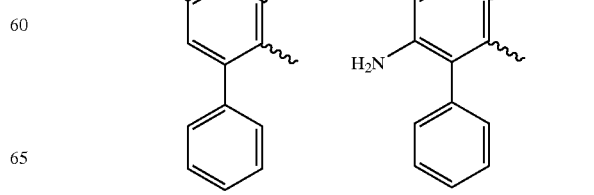

-continued
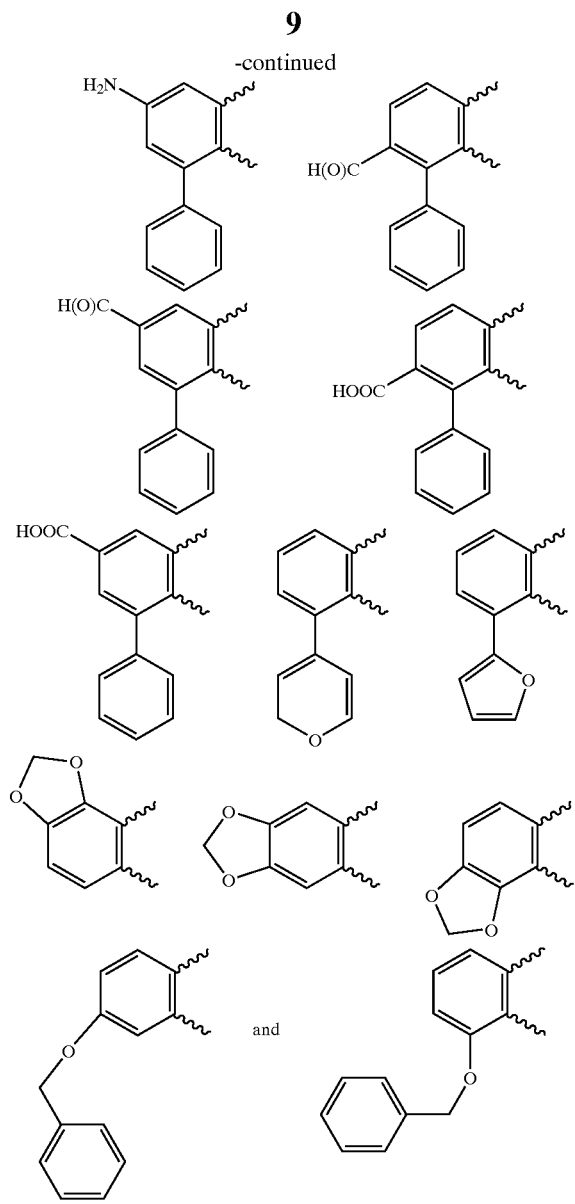
In a preferred embodiment, Compounds 2–3 of the present invention are those compounds wherein, $R_4$—N—$R_5$ is selected from the group consisting of the following:
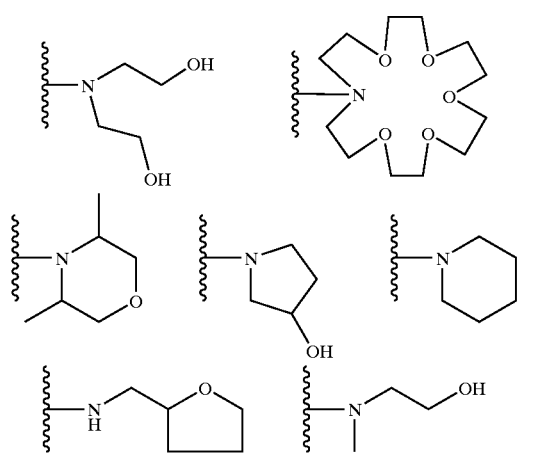
-continued
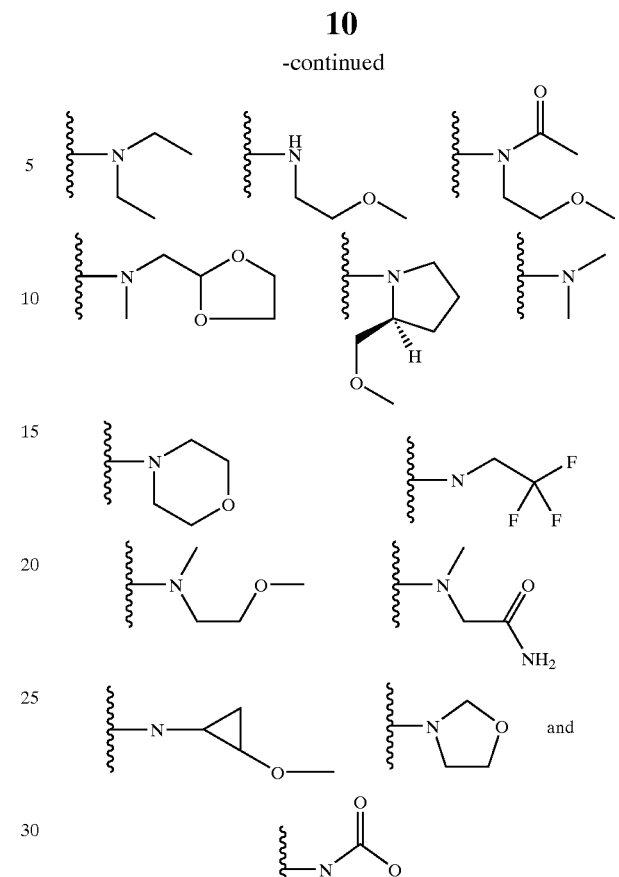
In another embodiment Compounds 2–3 of the present invention are those compounds wherein, $R_6$ is selected from the group consisting of the following:
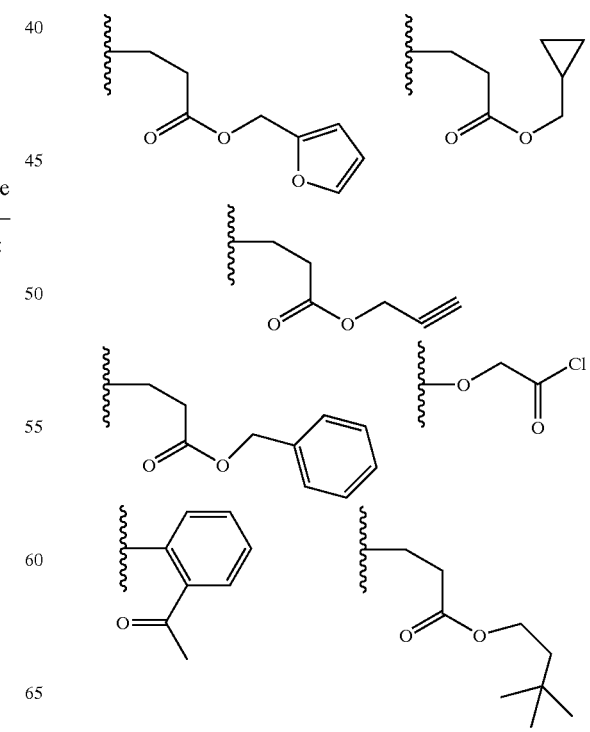

-continued
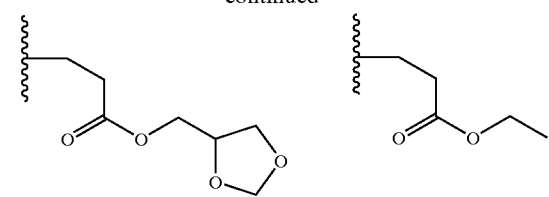
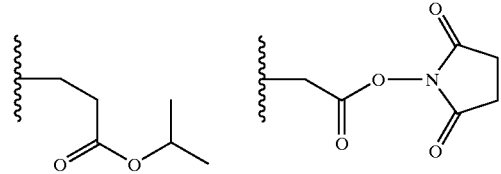
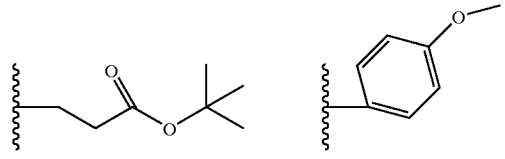
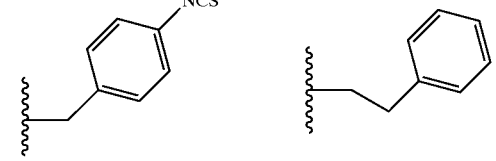
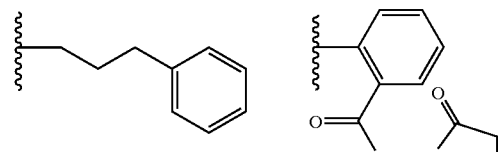
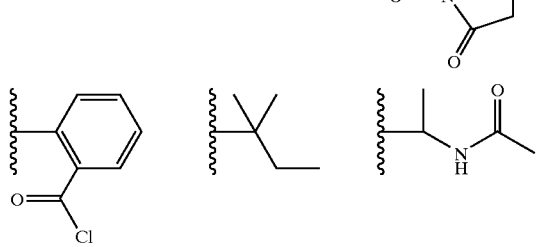
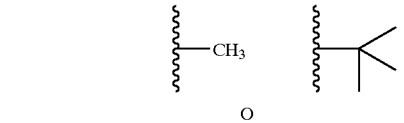
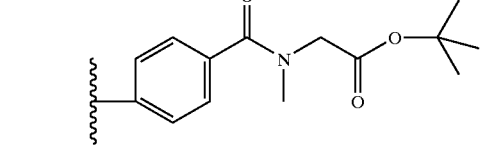
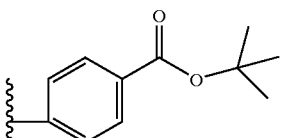
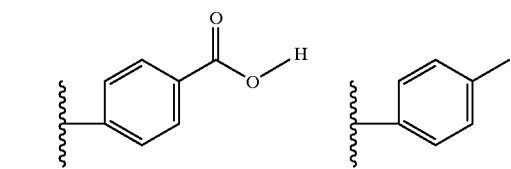
-continued
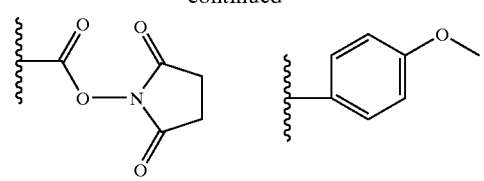
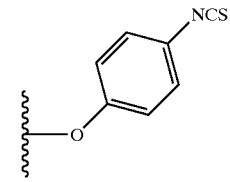
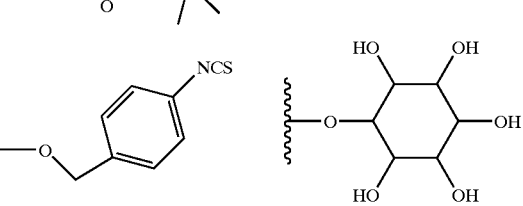
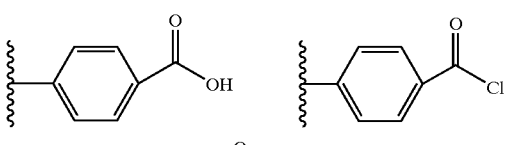
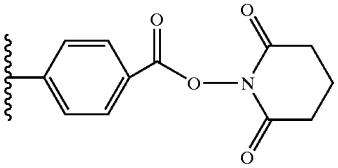
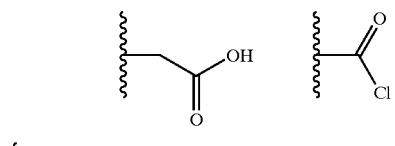
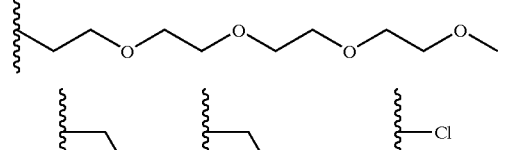
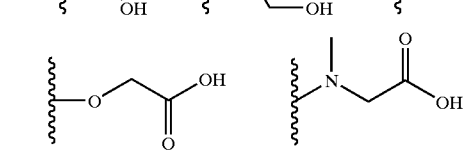
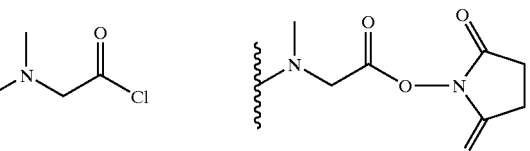
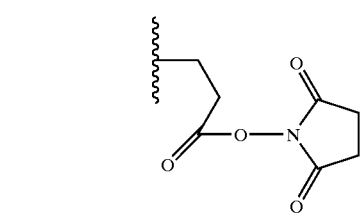

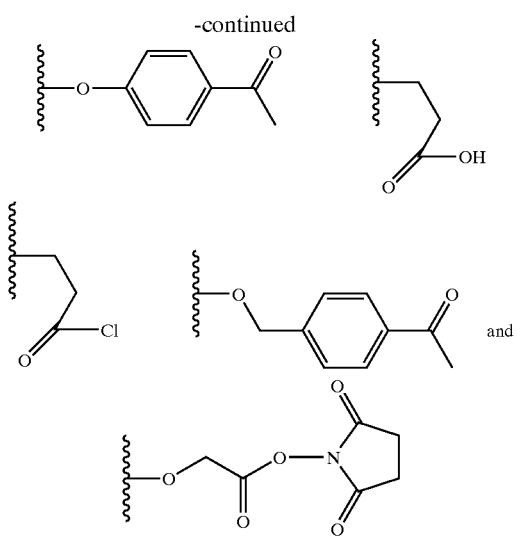

a. Linker

In another embodiment, Compound 3 of the present invention are those compounds wherein, the linker group is hydrolyzable. The linker group of the prodrug may be cleaved by enzymatic cleavage or preferably by hydrolysis under physiological conditions including but not limited to, aqueous conditions in living animals, to yield Compound 2. The rate of hydrolysis of the linker group under physiological conditions is preferably from about 1 minute half-life to about 48 hour half-life.

b. Hydrolysis

The term "hydrolyzable" as used herein refers to whether the group is capable of or prone to hydrolysis (i.e., splitting of the molecule or group into two or more new molecules or groups due to the net insertion of a water molecule) at a rate of about 1 minute half-life to 48 hour half-life.

The linker group may be any group that may be hydrolyzed or enzymatically cleaved to yield Compound 2. In a preferred embodiment, the linker group is of the formula:

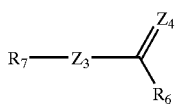

wherein, $Z_3$ and $Z_4$ independently are S or O; and $R_7$ represents —$CH_2$—, —$CH(CH_3)$—, —$CH(Ph)$-, —$C(CH3)(COOH)$— or $CH(CH(CH3)2)$—.

A representative example of the hydrolysis of the linker group of the prodrug to yield Compound 2 is presented in (Scheme 1), wherein $Z_3$ and $Z_4$ independently are each O. Hydrolysis or enzymatic cleavage of the $R_6$ ester yields a hemiaminal that collapses with liberation of the $R_7$ aldehyde, thereby generating Compound 2 comprising a free tertiary amine. Both $R_6$ and $R_7$ can be selected to give different rates of conversion back to the free tertiary amine. For example, increasing substitution at $R_6$ or $R_7$, or a combination thereof, may increase the stability towards hydrolysis. Furthermore, electron withdrawing groups on the $R_6$ moiety decreases the stability. In addition to the varying of $R_6$ or $R_7$ disclosed herein, additional factors that may be vary the stability of the quaternary amine may be found in N. Bodor, Journal of Medicinal Chemistry 1980, vol 23 #5 pp 469–480 "Soft Drugs. 1. Labile Quaternary Ammonium Salts as Soft Antimicrobials"; and G. Brouillette et al; Journal of Pharmaceutical Sciences, 1996, vol 85 #6, pp620–623, the contents of which are incorporated herein by reference.

SCHEME 1

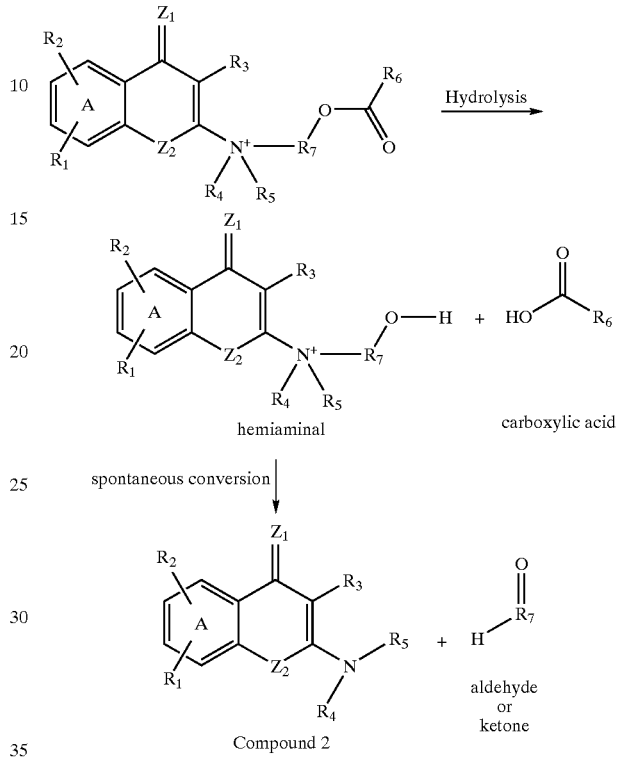

c. Targeting Agent

In another embodiment, compounds of the present invention are those compounds wherein, $R_6$ further comprises one or more targeting agents (T) covalently attached thereto. Targeting agents allow the prodrugs of the present invention to be delivered selectively to specific types of cells, tissues, organs or extracellular structures. As discussed above, treatment with Compound 1 (LY294002) suffers from poor bioavailability, rapid metabolism and side effects because the compound is not tissue specific. Therefore, it is highly desirable to limit the location of the drug to that of the area of treatment or at least prevent it from reaching the tissues where if can cause side effects, and to ensure that at any particular time effective, but not excessive, amounts of the drug are used. The use of targeting agents may allow the prodrugs of the present invention to be concentrated at the site of treatment rather than evenly distributed throughout the entire body or to be metabolized prematurely or excreted too quickly. Once being delivered to the site of treatment, the linker may be enzymatically cleaved or hydrolyzed as described above to yield Compound 2. Moreover, the use of targeting agents may limit the dosage required to be administered in order to achieve an effective concentration of the drug at the site of treatment. The use of targeting agents may also allow for more infrequent dosage or even alternative methods of administration in order to achieve an effective concentration of the drug at the site of treatment.

The targeting agent are preferentially attached to the compounds of the present invention via a covalent bond which may be formed by methods including, but not limited to, a nucleophilic or electrophilic group of the targeting agent that is covalently reacted with an electrophilic or nucleophilic group (respectively) on the linker.

In one embodiment of the present invention, Compounds 2–3 of the present invention are those compounds wherein, $R_6$-T is selected from the group consisting of the following:

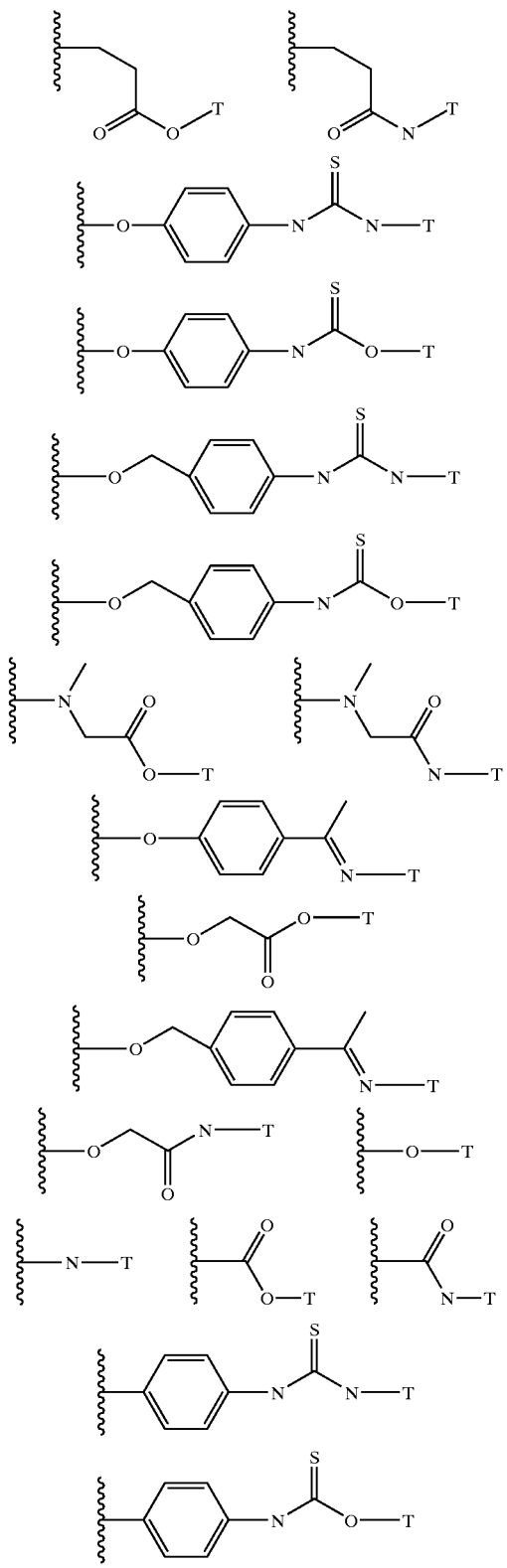

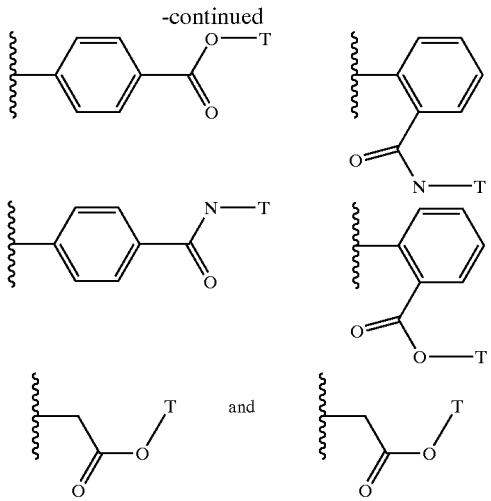

Targeting agents which may be reacted with the prodrugs of the present invention include, but are not limited to, carbohydrates, vitamins, peptides, proteins, nucleosides, nucleotides, nucleic acids, liposomes, lipids, bone-seeking agents and cartilage-seeking agents. The targeting agent may also be a molecule which is bound by a receptor in a desired tissue and optionally transported into a cell by a receptor-mediated process. Representative examples of such targeting agents include, but are not limited to, diazepines that bind to peripheral benzodiazepine receptors (PBRs) present in glial cells in the brain. Representative examples of such diazepines are discussed in G. Trapani, et al. Bioconjugate Chem. 2003, vol 14, pp830–839 "Peripheral Benzodiazepine Receptor Ligand-Melphalan Conjugates for Potential Selective Drug Delivery to Brain Tumors," the contents of which are incorporated by reference.

Representative vitamins that may be used as targeting agents include, but are not limited to, folate, vitamin $B_{12}$ or vitamin C. The term "folate" encompasses folic acid derivatives with capacity to bind with folate-receptors. Representative examples of folates that may be used as targeting agents include, but are not limited to, folic acid, folinic acid, pteropolyglutamic acid, and folate receptor-binding pteridines such as tetrahydropterins, dihydrofolates, tetrahydrofolates and their deaza and dideaza analogs. Other suitable folates are folate analogs including, but not limited to, aminopterin, amethopterin (methotrexate), $N_{10}$-methylfolate, 2-deamino-hydroxyfolate, deaza analogs such as 1-deazamethopterin or 3-deazamethopterin, and 3'5'-dichloro4-amino-4-deoxy-$N_{10}$-methylpteroyl-glutamic acid (dichloromethotrexate). Methods of conjugating molecules to folates that are suitable for covalent attachment to compounds of the present invention are disclosed in U.S. Pat. Nos. 6,576,239, 5,820,847, 5,688,488, 5,108,921, 5,635,382, and 5,416,016 the contents of which are incorporated herein by reference. Methods of conjugating molecules to vitamin C that are suitable for covalent attachment fo compound of the present invention are dislosed in S. Manfrdini J. Med. Chem. Vol 45, pp559–562, 2002 the contents of which are incorporated herein by reference.

Representative peptides and peptidomimetics that may be used as targeting agents include, but are not limited to, an RGD-containing peptide selected from the group consisting of RGDs, c(RGDfK), vitronectin, fibronectin, somatostatin-receptor agonists and somatostatin-receptor antagonists. Molecules that bind to the avb3 integrin receptor and act as antagonists may be used at targeting agents as described in U.S. Pat. Nos. 6,552,079, 6,426,353B, WO 2002/40505A2, and U.S. Patent Publications 2002/0055499, 2002/0061885, 2002/0065291, 2002/0072500, U.S. 2002/0072518; W. Arap et al. Science vol 279, number 16, 1998, pp 377–380; R J Kok et al. Biojonjugate Chem. 2002, vol 13, pp128–135; D A Sipkins et al. Nature Medicine vol 4, number 5, 1998 pp623–626; P M Winter et al. Cancer Research 2003, vol 63, pp5838–5843; and J D Hood et al. Science vol 296, pp2404–2407; the contents of which are incorporated herein by reference. Representative proteins that may be used as targeting agents include, but are not limited to, antibodies or fragments thereof, such as a tumor-specific monoclonal antibody or fragment thereof. Representative bone-seeking agents that may be used as targeting agents include, but are not limited to, phosphonate, phosphonic acid, aminomethylphosphonic acid, phosphate, polyphosphate, and hydroxyapatite-binding polypeptides. Other peptides include chlorotoxin (U.S. Pat. No. 6,429,187B1) and tissue factor (G. M. Lanza, et al. "Targeted Antiproliferative Drug Delivery to Vascular Smooth Muscle Cells with a Magnetic Resonance Imaging Nanoparticle Contrast Agent"; Circulation, 2002 volume 106 pp2842–2847).

Other suitable targeting agents include antibodies. The antibodies may be of classes IgG, IgM, IgA, IgD or IgE, or fragments or derivatives thereof, including Fab, $F(ab')_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibodies may also be a chimeric antibody. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include, but are not limited to, such antigens as are and include, but are not limited to, carcinoembryonic antigen (CEA), mucins such as TAG-72, human milk fat globule antigens, prostate serum antigent (PSA), prostate specific membrane antigen (PSMA), PS (phosphatidyl serine), and receptors including, but not limited to, the IL-2, EGF, VEGF and transferrin receptors. Other representative antigens associated with tumors include, but are not limited to, those tumor associated antigens described in Zalcberg and McKenzie, J. Clin. Oncology, Vol. 3; pp. 876–82 (1985), WO 01/68709A1, and U.S. Patent Publication US2004/0009122A1, the contents of which are incorporated herein by reference.

Other suitable targeting agents include glucose, galactose, mannose, mannose 6-phosphate, hormones (e.g., insulin, growth hormone, and the like), growth factors or cytokines (e.g., TGFβ, EGF, insulin-like growth factor, and the like), YEE(GalNAcAH).sub.3 or derivatives, cobalamin, α-2 macroglobulins, asialoglycoprotein, albumin, texaphyrin, metallotexaphyrin, antibodies, antibody fragments (e.g., Fab), single-chain antibody variable region (scFv), transferrin, any vitamin and any coenzyme The targeting agent may also be an agent that delivers the prodrug to bones. Bone targeting agents include, but are not limited to, EDTMP DOTMP, and ABEDTMP, which are disclosed in U.S. Pat. Nos. 4,937,333, 4,882,142, 5,064,633 and WO-94/00143, the contents of which are incorporated herein by reference. DOTMP and EDTMP may be attached to the linker moiety by any method including, but not limited to, the coupling chemistry shown in FIG. 3 and the alkylation chemistry shown in FIG. 4 where the R group can have an appropriate electrophilic or nucleophilic group that reacts with the nucleophilic or electrophilic (respectively) group of the linker moiety. Further details of the coupling chemistry are provided in Tetrahedron 1999, 55, pp12997–13010, the contents of which are incorporated by reference. Further details of the alkylation chemistry are provided in Proc. SPIE-Int. Soc. Opt. Eng. 1999, 3600 (Biomedical Imagn. Reporters Dyes & Instrumental, pp99–106; U.S. Pat. No. 5,177,054; J. Med. Chem. 1994, 37, 498–511; Tetrahedron Letters, 1989, 30 #51 pp7141–7144; and U.S. Pat. No. 5,955,453, the contents of which are incorporated by reference.

The targeting agent may be used to deliver the prodrug to bones as a slow release reservoir site for the compounds of the present invention. The targeting agent may be a bone seeking (osteotropic) moiety attached to the compounds of the present invention via an acid cleavable linker attached to the quaternary amine. Examples of an acid cleavable linker include, but are not limited to, an ortho acid-amide linkage. Under acidic conditions the protein-ACL-3 amide linkage is readily cleaved freeing the native amino group of the amide functionality as described in WO-94/00143 the contents of which are incorporated by reference. During osteoclastic bone resorption, which involves an acidic mediated mechanism, the attachment tethering the prodrug to bone may be cleaved releasing the compounds of the present invention.

The targeting agent used to deliver the prodrugs to bones may be a molecule that binds with notch receptors. Notch signaling plays a key role in the development and differentiation of various hematopoietic lineages. As discussed in Jundt et al., Blood, 102(11): 928a (2003), ligand-induced notch signaling is a novel growth factor for multiple myeloma cells and suggests that these interactions contribute to lymphomagenesis of multiple myeloma in vivo.

The bone targeting agent may have a high affinity for calcium ions in hydroxyapatite, the major constituent of bone. The compound of the invention can be targeted to calcium deposits in regions of the body other than bone, such as calcium deposits in the arteries, heart, kidney, or gall bladder. However, the bone targeting agent ideally selectively binds to bone tissue. A bone targeting agent of the invention is attracted to the bone tissue of the subject, preferably binds to the bone with a higher affinity than non-bone tissues, and remains bound for a certain length of time thereby delivering the composition to a bone environment. In other words, the bone targeting agent preferably binds to bone tissue with at least 2-fold greater affinity (e.g., at least 3-fold, at least 5-fold, at least 10-fold, or at least 25-fold greater affinity) than the bone targeting agent binds to non-bone tissue. The bone targeting agent reversibly binds to bone tissue, meaning that the bone targeting agent is eventually released from bone and expelled from the body.

The bone targeting agent may remain bound to bone tissue for a sufficient period of time to allow the quaternary prodrug to be hydrolyzed, thereby delivering the active drug to the target cells (e.g., bone marrow cells). The bone targeting agent can remain bound to bone for about 1 day (e.g., about 2 days, about 3 days, or about 7 days) to about 1 year (e.g., about 330 days, about 365 days, or about 400 days), after which the bone targeting agent is expelled from the body. The bone targeting agent can remain bound to bone for about 7 days (e.g., about 7 days, about 14 days, or about 21 days) to about 6 months (e.g., about 90 days, about 120 days, or about 150 days). For example, a bone targeted prodrug can remain bound to the bone for 30 days, during which time the drug is released. After about 45 days the bone targeting agent would be released from the bone and eventually excreted. Thus, a bone targeting agent for use in the invention can be selected based on binding kinetics to bone tissue. Candidate bone targeting agents can be screened in vitro by determining affinity to bone tissue (e.g., hydroxyapatite) in, for example, a multi-well format. Candidate bone targeting agents also can be screened in vivo by assessing the rate and timing of excretion of candidate bone targeting agents from the body. In this respect, the bone targeting agent preferably is expelled from the body via the kidneys.

Figure 7:
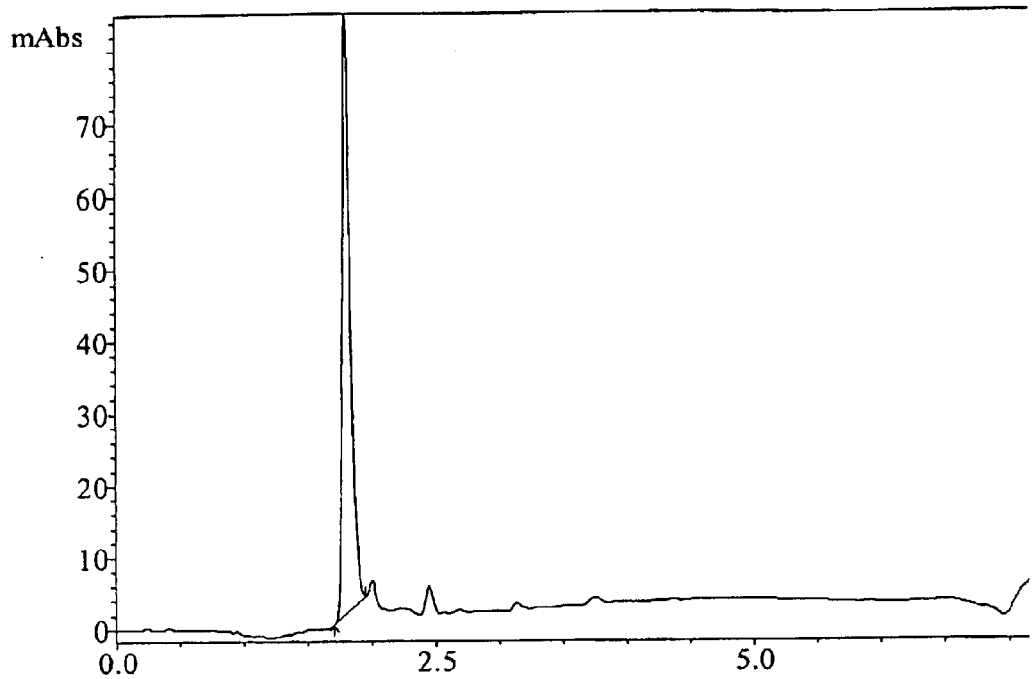
FIG. 7 shows the UV and ELS Chromatograms of Compound 1126 (A036-33).
Figure 7:
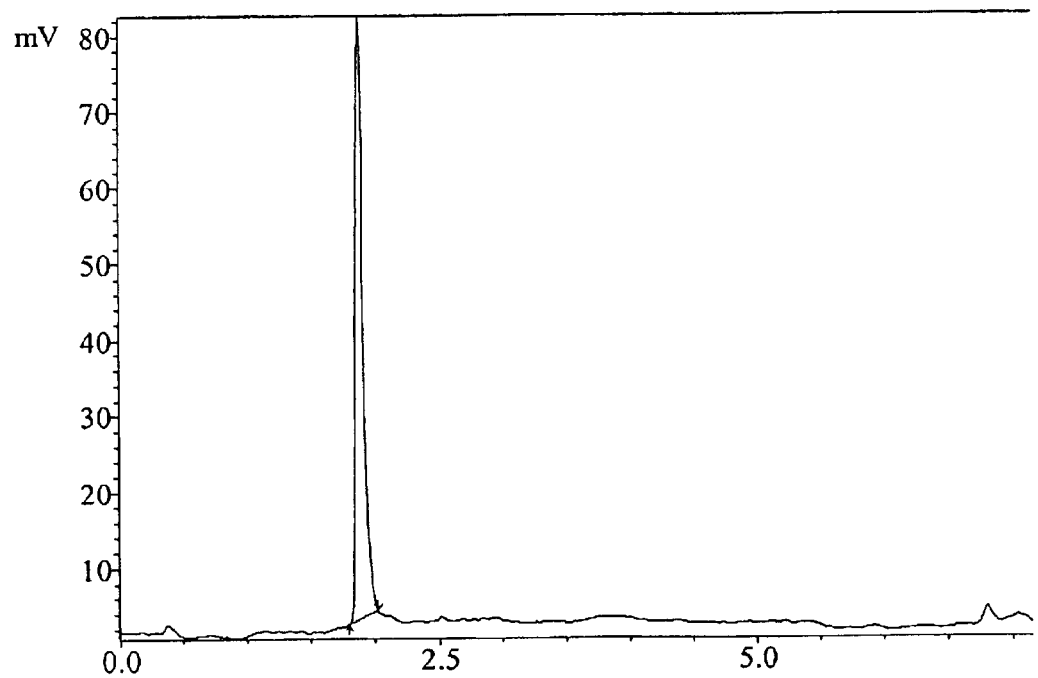

The bone targeting agent desirably is selected from the group consisting of a phosphate, a phosphonate, a bisphosphonate, a hydroxybisphosphonate, an aminomethylenephosphonic acid, and an acidic peptide. The bone targeting agent of the invention can carry one, more than one, or a mixture of these groups. For example, the bone targeting agent can be a phosphonate, meaning that the bone targeting agent may comprise one phosphonate, two phosphonates, or three or more phosphonates. One suitable bone targeting agent for use in the invention is EDTMP (ethylene diamine-N,N,N',N'-tetrakis(methylenephophonic acid), the chemical structure of which is set forth in FIG. 1, currently FDA approved (Quadramet™) as the radioactive $^{153}$Sm complex for delivering a selective radiation dose to bone metastases for pain palliation. EDTMP is a phosphonate that contains four phosphonic acid groups, and is therefore a tetraphosphonate. Compounds such as $^{153}$Sm-EDTMP are selectively localized in bone where tumors are present versus normal bone in a ratio of more than 10:1, probably because metabolic turnover of calcium is very high in the metastatic region. The $^{153}$Sm-EDTMP reportedly is rapidly taken up by the skeleton in osteoblastic bone metastases and cleared from the plasma. That portion of the compound that does not accumulate in the skeleton reportedly is rapidly excreted, and excretion is almost complete within 6 hours after administration (Jimonet et al., Heterocycles, 36, 2745 (1993)). The pain palliation is thought to be due to the radiation originating from the isotope bound to the osteoblastic bone metastases having some effect on the nearby metastatic tumor cells. Another clinically useful bone-targeting system is DOTMP (the chemical structure of which is set forth in FIG. 1, now in Phase III clinical trials (termed STR, skeletal targeted radiation) as the radioactive $^{166}$Ho complex designed to deliver large doses of radiation selectively to the bone marrow for the treatment of multiple myeloma. It should be noted that the radioactive $^{166}$Ho-DOTMP complex localizes in the skeletal system and irradiates the nearby bone marrow which houses the malignant myeloma cells. Like the $^{153}$Sm-EDTMP system, the phosphonate that does not localize in the bone is cleared through the urine and out the body. In general, the skeletal uptake is about 20 to about 50% of the injected dose, and the localization in areas of the skeleton with tumor infiltration is illustrated in FIG. 7 of Bayouth et al., J. Nucl. Med., 36, 730 (1995).

Preferably, the bone targeting agent is a polyphosphonic acid. Polyphosphonic acid has been demonstrated to successfully target biologically-active molecules to bone tissue. For example, conjugation (via isothiocyanato chemistry) of polyaminophosphonic acids, such as ABDTMP (the chemical structure of which is set forth in FIG. 1, to growth factors (to stimulate bone formation) successfully resulted in the targeting of the growth factors to the bones of rats (see, for example, International Patent Application WO 94/00145). Similarly, bone targeting agents have been coupled to proteins. For example bisphosphonates that were conjugated to human serum albumin successfully delivered the protein to bone in vitro (Biotechnol. Prog., 16, 258 (2000)) and in vivo (Biotechnol. Prog., 16, 1116 (2000)). The utility of bone-seeking agents extends beyond delivery of proteins to bone and includes, for instance, small therapeutic molecules. A conjugate comprising a bone-seeking bisphosphonate and an alkylating agent, such as BAD (the chemical structure of which is set forth in FIG. 1, has been generated (see, for example, Wingen et al., J. Cancer Res. Clin. Oncol., 111, 209 (1986)). In this molecule, the alkylating agent is not specific in its interaction with its target (DNA), and, thus, there is no requirement for cleavage between the bisphosphonate (i.e., bone-seeking agent) and the alkylating moiety. The bisphosphonate-alkylating agent demonstrated efficacy in a rat osteosarcoma model using BAD. Another series of studies have been performed using the antifolate antineoplastic agent methotrexate that has been covalently attached to bisphosphonates, designated MTX-BP and shown in FIG. 1 (see, for example, Sturtz et al., Eur. J. Med. Chem., 27, 825 (1992); Sturtz et al., Eur. J. Med. Chem., 28, 899 (1993); and Hosain et al., J. Nucl. Med., 37, 105 (1996)). Using Tc-99m labeled MTX-BP, it was determined that around 15% of the injected dose was localized in the skeleton after 4 hours with about 61% of the dose being excreted (Hosain, supra). MTX-BP further demonstrated five times greater anticancer activity compared with methotrexate alone in animal models of transplanted osteosarcoma (Sturtz 1992, supra). Similar work has been described using the conjugate CF—BP, a carboxyfluorescein group with an appended bisphosphonate whose chemical structure is set forth in FIG. 1 (Fujisaki et al., Journal of Drug Targeting, 4, 117 (1994)). In this molecule, the CF group is a fluorescent marker to quantitate pharmacokinetics and biodistribution, and is connected to the bone targeting agent through an ester bond which is susceptible to hydrolysis in vivo. Studies in rats injected intravenously indicated that CF—BP localized in the bone and served as a slow release mechanism for CF generated via general hydrolysis of the ester linkage (Fujisaki, supra).

In another embodiment, the bone-seeking agent can be a peptide, such as $(Asp)_6$ and $(Glu)_6$. The acid-rich peptide sequence of the glycoprotein osteonectin, which is found in abundance in bone and dentin, has a strong affinity to hydroxyapatite (Fujisawa et al., Biochimica et Biophysica Acta, 53, 1292 (1996)). Thus, peptide ligands comprising acidic amino acids are ideal candidates for bone targeting agents. Indeed, $(Glu)_{10}$, when attached to biotin, successfully recruited labeled strepavidin to hydroxyapatite (described further in Chu and Orgel, Bioconjugate Chem., 8, 103 (1997), and International Patent Application WO 98/35703). In addition, the biological half-life of the fluorescein isothiocyanate conjugated to $(Asp)_6$ was 14 days in the femur (Kasugai et al., Journal of Bone and Mineral Research, 15(5), 936 (2000)), which is an acceptable half-life for the bone targeting agent of the invention. Likewise, delivery of estradiol-$(Asp)_6$ conjugates to bone has been demonstrated in ovariectomized animals with concomitant inhibition of osteoporectic-type bone loss (Kasugai et al., Journal of Bone and Mineral Research (Suppl 1), 14, S534 (1999)). It is believed that the $(Asp)_6$ tether to bone is metabolized during the bone resorption process mediated by osteoclasts. Therefore, the acidic peptide ligand provides not only a means of recruiting compounds to bone, but also provides a mechanism of slowly releasing compounds to bone cells and surrounding tissue.

Figure 2:
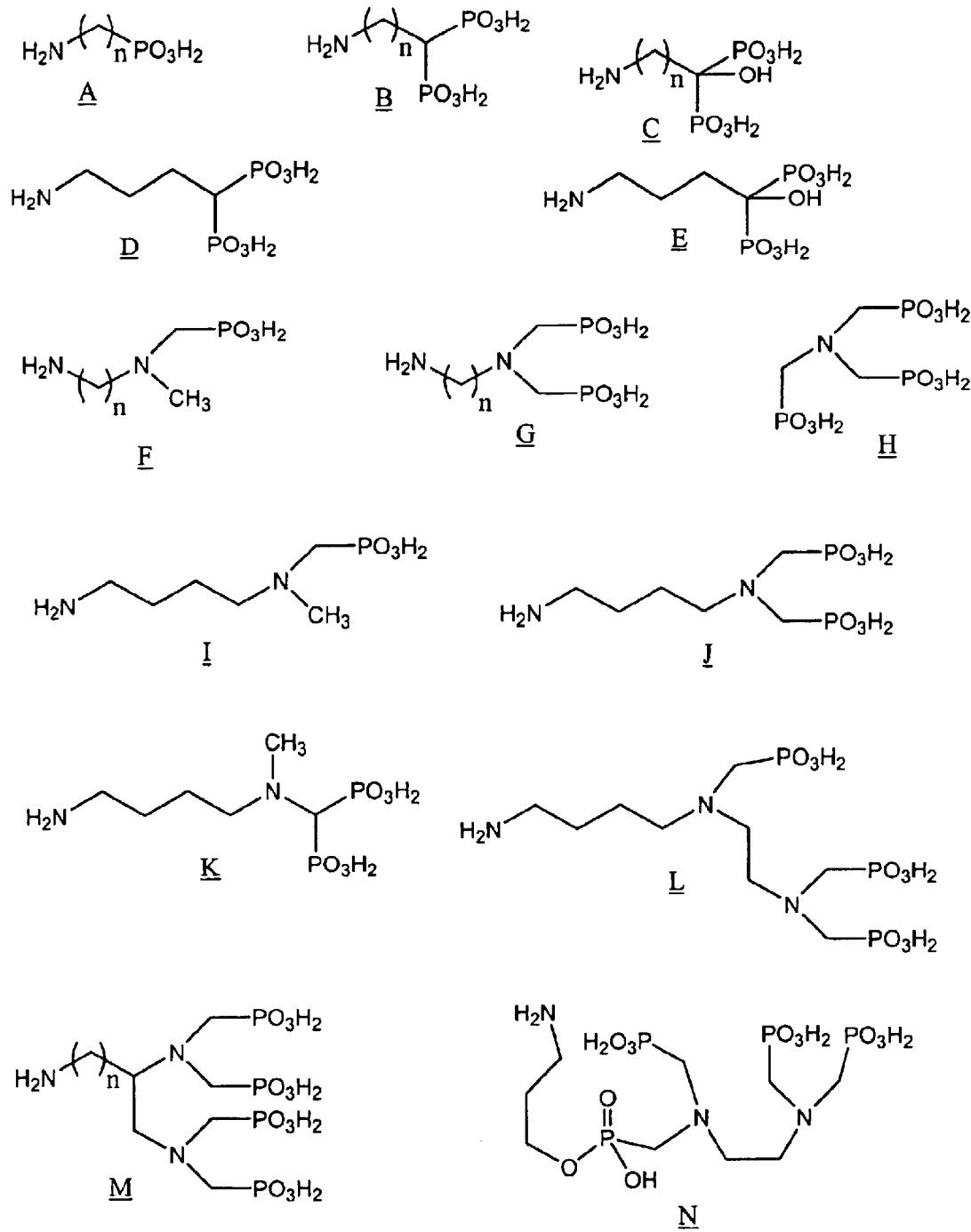
FIG. 2 shows the chemical structures of potential bone targeting agents.

Other examples of bone targeting agents include, but are not limited to amino- and hydroxy-alkyl phosphonic and diphosphonic acids; hydroxybisphosphonic acids including alendronate, pamidronate, 4-aminobutylphosphonic acid, 1-hydroxyethane-1,1-diphosphonic acid, and aminomethylenebisphosphonic acid; phosphates such as phytic acid; and aminomethylenephosphonic acids such as N,N-bis (methylphosphono)-4-amino-benzoic acid and nitrilotri (methylphosphonic acid). Nonlimiting examples of some bone targeting agents are shown in FIG. 2.

Preferably, the bone targeting agent is an aminomethylenephosphonic acid. By "aminomethylenephosphonic acid" is meant a compound that contains an —$NCH_2PO_3H$ moiety, where the amino group has one, two, or three methylenephosphonic acid groups attached, and may be further substituted with other chemical moieties. An aminomethylenephosphonic acid may include one or more phosphonic acid groups and one or more amino groups. Examples of these aminomethylenephosphonic acids include but are not limited to the compounds F through N set forth in FIG. 2.

Figure 3:
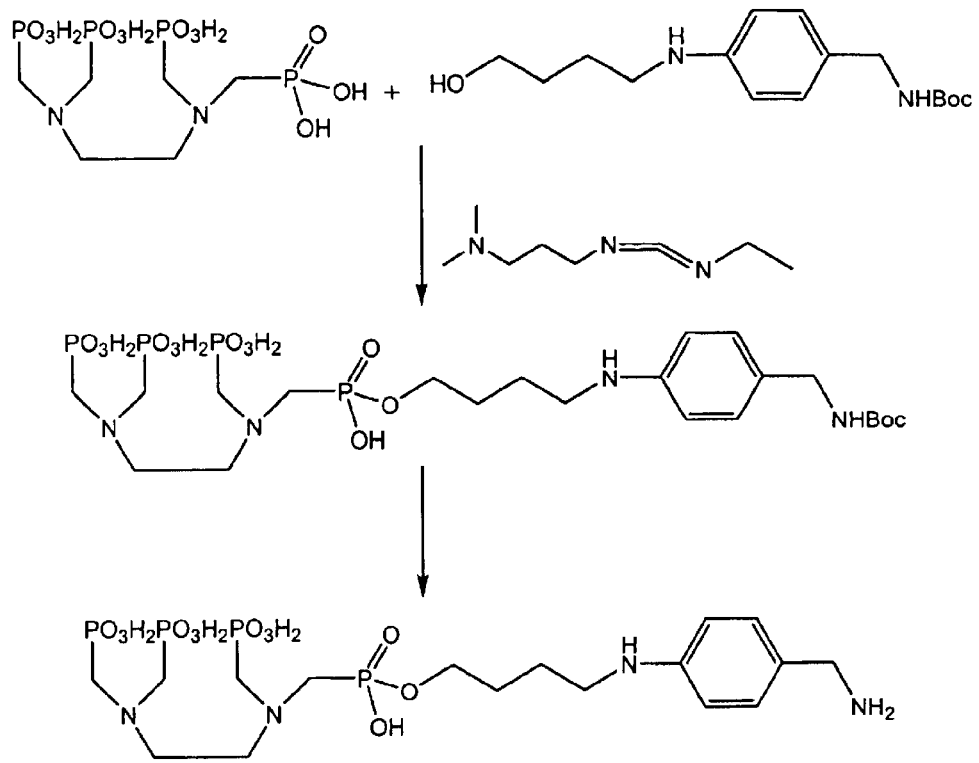
FIG. 3 shows the chemical reaction for modifying a phosphonate in a bone targeting agent.
Figure 4:
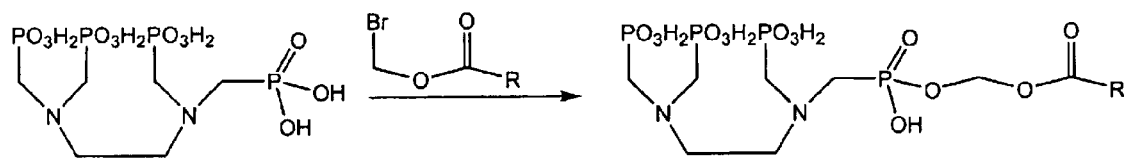
FIG. 4 shows the alkylation reaction to modify a phosphonate in a bone targeting agent.
Figure 5:
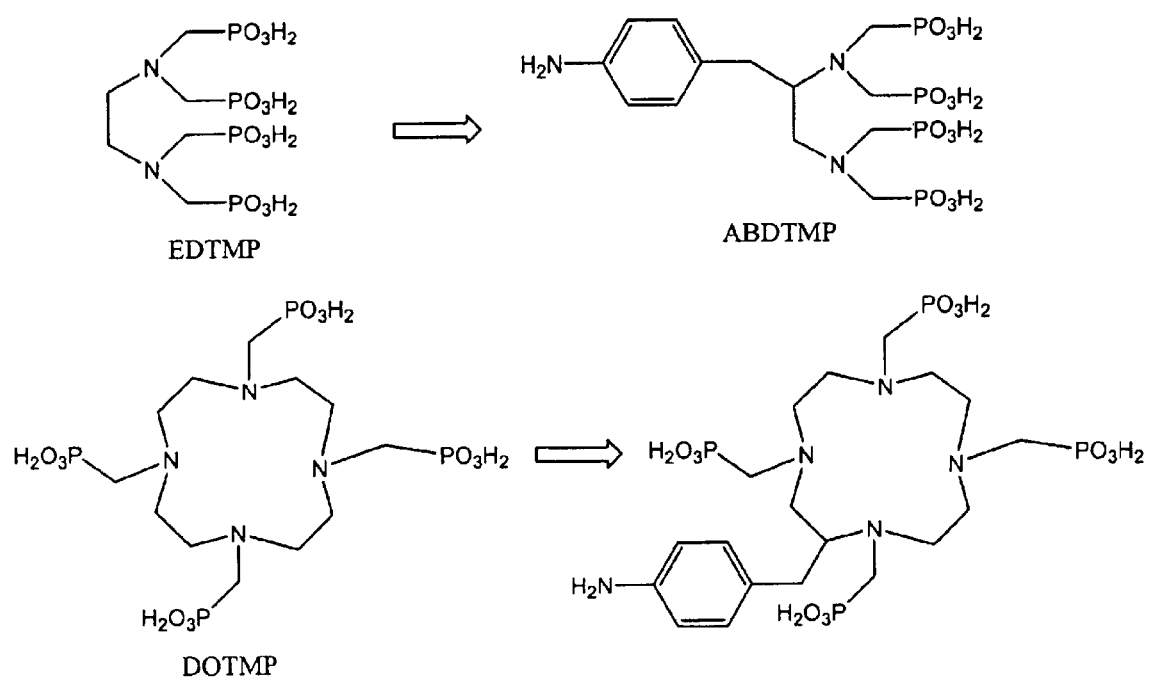
FIG. 5 shows a concept for chemically modifying EDTMP and DOTMP.
Figure 6:
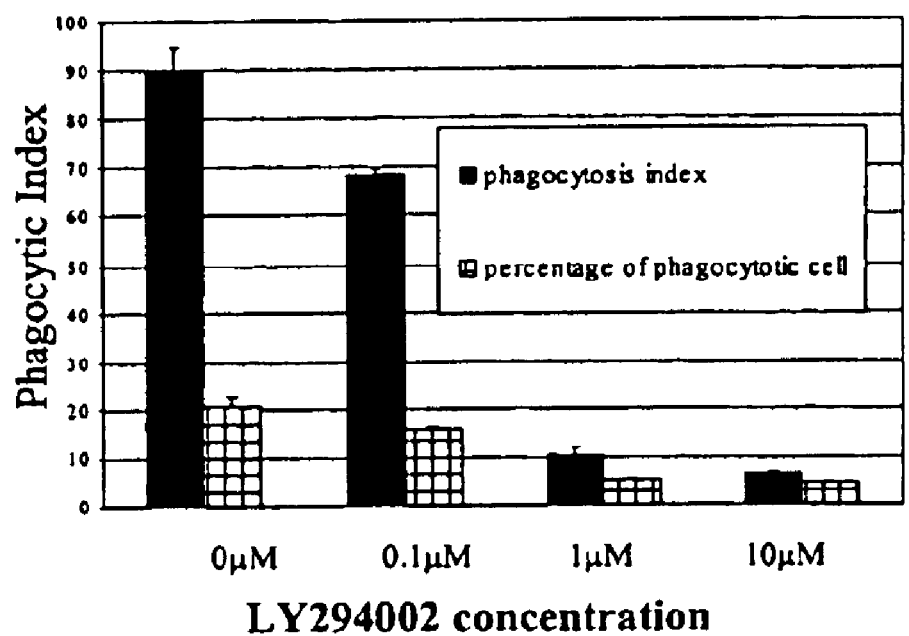
FIG. 6 shows the inhibition of phagocytosis by LY294002 in J774 cells. The columns indicate phagocytic index or percentage of cells positive for phagocytic response. The phagocytic index is the number of sRBC's (sheep red blood cells) found per 100 J774 cells and the % of phagocytic cells is the % of J774 cells that have phagocytized at least 1 sRBC. The error bars represent standard deviation of mean.

It is envisioned that these bone targeting agents and other bone targeting agents can be attached through one of the heteroatoms or by chemical modification that installs an additional attachment point. For example, EDTMP can be connected to a linker by one of the phosphorous oxygens to create a phosphonate linkage, as illustrated in FIG. 3 (see for example Vieira de Almedia et al., *Tetrahedron*, 55, 12997–13010 (1999).) The phosphorous oxygen can also be alkylated as shown in FIG. 4, where the R group can have, for example, a pendant amino group, to provide a secondary attachment point for ligation to, for example, an activated PEG. Other types of alkylation that could be utilized in the invention include but are not limited to examples similar to that involving DOTMP, as has been further described in Chavez et al., *Biomedical Imaging: Reporters, Dyes, & Instumentation*, Contag & Sevick-Muracia, Eds., Proc. SPIE, Vol. 3600, 99–106 (July, 1999), or as shown for other phosphonic acids further described in, for example, U.S. Pat. No. 5,177,064, U.S. Pat. No. 5,955,453, de Lombaert et al., *J. Med. Chem.*, 37, 498–511 (1994), and Iyer et al., *Tetrahedron Letters*, 30(51), 7141–7144 (1989). Alternatively, for chemical modification, EDTMP can be, for example, modified to generate ABDTMP by installation of an aniline group (as further described in, for example, FIG. 1 of International Patent Application WO 94/00145). The aniline amine is then available to form, for example, an amide bond. DOMTP could be similarly modified, as outlined in FIG. 5.

The terms "phosphonate, phosphate, and aminomethylenephosphonate" are meant to encompass the phosphonic acids, the phosphoric acids, and aminomethylenephosphonic acids, respectively, as well as any salts, hydrolyzable esters, and prodrugs of the phosphorous-based acids thereof. At the biological pH of 7.4 in the blood, or the more acidic pH around the bone, a certain portion of the phosphate or phosphonate of the bone targeting agent may be deprotonated and replaced with a counterion. Furthermore, the exchange of proton for calcium is an inherent event for the binding of the bone targeting agent to the hydroxyapatite in the invention. However, preparation and administration of the composition containing the bone targeting agent may or may not require complete protonation of the phosphorous acids therein. Therefore, the phosphonic acid, phosphoric acid, and aminomethylenephosphonic acid are drawn and utilized interchangeably with phosphate, phosphonate, and aminomethylenephosphonate. While not particularly preferred, biologically hydrolyzable esters of the phosphorus-based acids may also be utilized in the in vivo use of the bone targeting prodrugs. Similarly, prodrugs of the phosphorous-based acids may also be utilized in vivo to mask the acidity of the composition during, for example, formulation and administration.

The targeting agent may also be an agent that targets based upon properties of the particular tissue. Representative examples of such targeting agents include, but are not limited to, polymers that are selectively localized in tumor tissues due to the EPR effect (enhanced permeability and retention) as described in H. Maeda et al "Tumor vascular permeability and the EPR effect in macromolecular therapeutics: A Review"; Journal of Controlled Release, 2000 vol 63, pp 271–284, the contents of which are incorporated by reference. Other representative polymers are N-(2-hydroxypropyl)methacrylamide (HPMA) and (poly)L-glutamic acids.

The targeting agent may also comprise an RGD moiety. As discussed in Curnis et al., *Cancer Research*, 64(2): 565–571 (2004), RGD moieties target RGD fusion proteins to vasculature by interacting with interacts with cell adhesion receptors, including $\alpha_v\beta_3$ integrin.

3. Synthesis a. Main Ring System

The compounds of the present invention may be synthesized using LY294002 (Compound 1) as a starting product. LY294002 (Compound 1) may be obtained commercially or synthesized as described in Example 1 or as described in U.S. Pat. No. 5,703,075, the contents of which are incorporated herein by reference. One of ordinary skill in the art may also synthesize the compounds of the present invention using Compound 2 as a starting product.

b. Preparation of Derivatives of Main Ring System

The main ring system of Compounds 2 and 3 may be derivatives of the main ring system of LY294002 (Compound 1). Derivatives of the main ring system of Compound 3 may be prepared as disclosed in U.S. Pat. No. 5,703,075, the contents of which are incorporated herein by reference, for the preparation of main ring derivatives of LY294002 (Compound 1). Derivatives of the main ring system of Compound 3 may also be prepared by using commercially available compounds including, but not limited to, substituted 2-hydroxy-acetophenones.

c. Preparation of Derivatives of Morpholine Ring

The amine derivatives of Compound 3 may be prepared by the displacement of the thioalkyl group in Example 1 under conditions ranging from room temperature to forcing conditions (excess nucleophile and heating to 110° C.). Any primary or secondary nitrogen-containing nucleophile may react to give alternative amine substitutions to the morpholine ring structure (including different morpholine analogs). The synthesis of representative examples of such amine derivatives of Compound 3 are described in the Examples herein.

d. Preparation of Esters

As described above, esters may be used to form the quaternized compounds of the present invention. The quaternized compounds of the present invention are preferably formed using halo esters. In one preferred embodiment, the quaternized compounds of the present invention are formed using chloromethyl esters. Numerous chlorlomethyl esters useful in the preparation of the compounds of the present invention are available from commercial sources. In addition, chloromethyl esters may be synthesized as described in WO 02/42265, WO 94/23724, and U.S. Pat. Nos. 4,444,686, 4,264,765, and 4,342,768, the contents of which are incorporated herein.

e. Quaternization

The prodrugs of the present invention may be prepared by quaternizing the tertiary amine of Compound 1 or Compound 2 with a halomethyl ester, for example, as described in Example 4 and Example 6. Quaternized amine compounds are generally not reversible under mild conditions. However, the quaternary compounds of the present invention are readily hydrolyzable as discussed above. Halomethyl esters that may be used to quaternize the tertiary amine of Compound 1 or Compound 2 are commercially available or may be prepared as described in the Examples below.

f. Linkers

The prodrugs of the present invention may also be prepared by quaternizing the tertiary amine of Compound 1 or Compound 2 with a linker comprising at least two functional groups. The linker may be any natural or synthetic linker that is capable of quaternizing the tertiary amine and is also capable of being covalently attached to a targeting molecule or may already be attached to a targeting molecule.

Linkers are preferably comprised of an atom such as oxygen or sulfur, a unit such as —NH—, —CH$_2$—, —C(O)—, —C(O)NH—, or a chain of atoms. The molecular mass of a linker is typically in the range of about 14 to 200, preferably in the range of 14 to 96 with a length of up to about six atoms. Representative examples of linkers include but are not limited to a saturated or unsaturated aliphatic group which is optionally substituted, and wherein one or two saturated carbons of the chain are optionally replaced by —C(O)—, —C(O)C(O)—, —CONH—, —CONHNH—, —C(O)O—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The first functional group of the linker is used to quaternize the tertiary amine as discussed above. A preferred first functional group is a halomethyl ester including, but not limited to, chloromethylester and iodomethyl ester. The second functional group of the linker may be used to covalently attach a targeting agent.

The second functional group may be an electrophilic group or a nucleophilic group. Preferred second functional groups for covalently attaching targeting groups are isothiocyanate, haloacetamide maleimide, imidoester, thiophthalimide, N-hydroxysuccinimyl ester, pyridyl disulfide, phenyl azide, carboxyl (and acid chlorides thereof), amino, acyl hydrozide, semicarbazide, thiosemicarbazide, diazonium, hydrazine, azide, aminoalkylurea, aminoalkylthiourea, halotriazine, and meta (dihydroxyboryl)phenylthiourea. Other suitable reactive moieties which may be suitable for covalently attaching the prodrugs of the present invention to targeting agents include disulfides, nitrenes, sulfonamides, carbodiimides, sulfonyl chlorides, benzimidates, —COCH$_3$ and —SO$_3$H.

The appropriate second functional group will depend on the functional group of the targeting agent with which the covalent bond will be formed and by its susceptibility to loss of biological activity as a consequence of forming a given type of linkage. If the targeting agent is a protein, the second functional group may be reactive with side chain groups of amino acids making up the polypeptide backbone. Such side chain groups include the carboxyl groups of aspartic acid and glutamic acid residues, the amino groups of lysine residues, the aromatic groups of tyrosine and histidine, and the sulfhydryl groups of cysteine residues.

Carboxyl side groups presented by a targeting agent such as a polypeptide backbone may be reacted with amine second functional groups by means of a soluble carbodiimide reaction. Amino side groups presented by a targeting agent may be reacted with isothiocyanate, isocyanate or halotriazine second functional groups to effect linkage to the prodrugs of the present invention. Alternatively, amino side groups on the targeting agent may be linked to the prodrugs compounds of this invention bearing amine reactive groups by means of bifunctional agents such as dialdehydes and imidoesters. Aromatic groups presented by a targeting agent may be coupled to the prodrugs of this invention via diazonium derivatives. Sulfhydryl groups on targeting agent molecules may be reacted with maleimides or with haloalkyl targeting agent reactive groups such as iodoacetamide. Free sulhydryl groups suitable for such reactions may be generated from the disulfide bonds of protein immunoglobulin or may be introduced by chemical derivatization. Linkage to free sulfhydryl groups generated in the intra-heavy chain region of immunoglobulins does not interfere with the antigen binding site of the immunoglobulin but may render the antibody incapable of activating complement.

When the targeting agent is a glycosylated protein, an alternative to forming a linkage to the compounds of the present invention via the polypeptide backbone is to form a covalent linkage with the carbohydrate side chains of the glycoprotein according to the methods such as those of McKearn, et al., EPO 88,695. Thus, the carbohydrate side chains of antibodies may be selectively oxidized to generate aldehydes which may then be reacted either with amine reactive groups to form a Schiff base or with hydrazine, semicarbazide or thiosemicarbazide reactive groups, to give the corresponding hydrazone, semicarbazone or thiosemicarbazone linkages. These same methods may also be employed to link the prodrugs of this invention to non-proteinaceous targeting agents such as carbohydrates and polysaccharides.

An alternative targeting agent reactive moiety useful for linkage to carbohydrates and polysaccharides without the necessity for prior oxidation is the dihydroxyboryl groups, such as is present in meta (dihydroxyboryl)phenylthiourea derivatives. This group is reactive with targeting agents containing a 1,2-cis-diol, forming a 5-membered cyclic borate ester, and thus is of use with those carbohydrates, polysaccharides and glycoproteins which contain this group. The dihydroxyboryl derivatives may also be used to link the prodrugs of this invention to ribonucleosides, ribonucleotides and ribonucleic acids, since ribose contains a 1,2-cis-diol group at the 2',3' position, as disclosed by Rosenberg, et al., Biochemistry, 11, 3623–28 (1972). Deoxyribonucleotides and DNA targeting agents may not be linked to the present prodrugs in this fashion as the 3' hydroxyl group is absent. The latter targeting agents may, however, be conjugated to isothiocyanate derivatives of prodrugs by first forming an allylamine derivative of the deoxyribonucleotide as disclosed by Engelhardt, et al., EPO 97,373.

When the targeting agent to be linked with the prodrugs of this invention is an intact cell, either polypeptide reactive or carbohydrate reactive moieties may be employed. Hwang and Wase, Biochim. Biophys. Acta, 512, 54–71 (1978), disclose the use of the diazonium derivative of the bifunctional EDTA chelator of Sundberg, et al., J. Med. Chem., 17, 1304 (1974), to label erythrocytes and platelets with indium-11. The dihydroxyboryl group is reactive with a variety of bacteria, viruses and microorganisms, see Zittle, Advan. Enzym., 12 493 (1951) and Burnett, et al., Biochem. Biophys. Res. Comm., 96, 157–62 (1980).

Preferred linkers that may be used to covalently quaternize the tertiary amine of Compound 1 or Compound 2 and are of the formula:

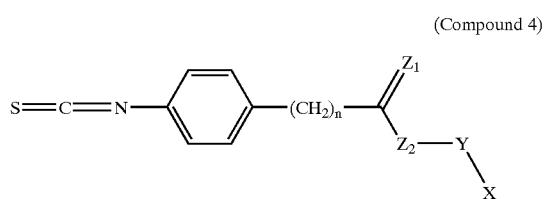

(Compound 4)

wherein,
X represents a halo group;
Y represents —CH$_2$—, —CH(CH$_3$)—, —CH(Ph)-, —C(CH3)(COOH)— or CH(CH(CH3)2)—
Z$_1$ and Z$_2$ independently are S or O; and
n=0 to 4.

In one embodiment, Compound 4 of the present invention are those compounds wherein,
X represents Cl or I;
Y represents —CH$_2$—, —CH(CH$_3$)—, —CH(Ph)-, —C(CH3)(COOH)— or CH(CH(CH3)2)—;
Z$_1$ and Z$_2$ independently are O; and
n=0.

In another embodiment, Compound 4 of the present invention are those compounds wherein,
X represents Cl or I;
Y represents —CH$_2$—, —CH(CH$_3$)—, —CH(Ph)-, —C(CH3)(COOH)— or CH(CH(CH3)$_2$)—;
Z$_1$ and Z$_2$ independently are 0; and
n=1.

Compound 4 provides linkers with both an alkyl and aryl carboxylic backbone which provides flexibility in the cleavage rate of the final quaternary nitrogen. The linkers of Compound 4 may be prepared using commercially available starting products as described in Example 5.

g. Purification

The compounds of the present invention may be isolated using standard purification methods. The hydrolyzable bond of the compounds of the present may be prone to hydrolysis during the purification of the compounds.

The present invention is also directed to methods of purifying the compounds of the present invention comprising adding the compounds to a solution comprising at least 0.1% acid (v/v) to solubilize the compound. The compound is then purified by performing chromatography, preferably HPLC.

h. Testing

The prodrugs of the present invention may be tested to determine the rate of hydrolysis of the hydrolyzable bond and the products of hydrolysis by performing HPLC analysis of the prodrug exposed to cleavage conditions as a function of time. The biological activity of the compounds of the present invention may be measured by methods including, but not limited to, blocking phagocytosis in macrophage cell line J774 cells as described in Example 17. The biological activity of the compounds of the present invention may also be measured by PI-3 kinase enzyme assays as described by U.S. Pat. No. 5,480,906; K. Fuchikami et al J. Biomol. Screen, 2002 Oct. pp441–450; V I Silveria et al J. Biomol. Screen, 2002, Dec. 7(6), 507–514; BE Drees Combinatorial Chemistry and Highthroughput Screening 2003, vol 6, 321–330, the contents of which are incorporated by reference.

i. Salts

The compounds of the present invention are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the compounds of the present invention which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties.

Preferred salts of the compounds of the present invention include hydrochloride salts, methanesulfonic acid salts and trifluoroacetic acid salts with methanesulfonic acid salts being more preferred. In addition, pharmaceutically acceptable salts of the compounds of the present invention may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

In general, the counterions of the salts of the compounds of the present invention are determined by the reactants used to synthesized the compounds. There may be a mixture of counterions of the salts, depending on the reactants. For example, where NaI is added to facilitate the reaction the counterion may be a mixture of Cl and I counter anions. Furthermore preparatory HPLC may cause the original counterion to be exchanged by acetate anions when acetic acid is present in the eluent. The counterions of the salts may be exchanged to a different counterion. The counterions are preferably exchanged for a pharmaceutically acceptable counterion to form the salts described above. Procedures for exchanging counterions are described in WO 2002/042265, WO 2002/042276 and S. D. Clas, "Quaternized Colestipol, an improved bile salt adsorbent: In Vitro studies." Journal of Pharmaceutical Sciences, 80(2): 128–131 (1991), the contents of which are incorporated herein by reference. For clarity reasons the counterions are not explicitly shown in the chemical structures herein and the characterization of the compounds is based on the identified quarternary cation.

4. Composition

The present invention also encompasses a composition comprising one or more compounds of the present invention. The compositions of the present invention may further comprise one or more pharmaceutically acceptable additional ingredient(s) such as alum, stabilizers, antimicrobial agents, buffers, coloring agents, flavoring agents, adjuvants, and the like.

a. Formulation

Compositions of the present invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of the present invention may also be formulated transdermal formulations comprising aqueous or nonaqueous vehicles including, but not limited to, creams, ointments, lotions, pastes, medicated plaster, patch, or membrane.

Compositions of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. The compositions of the invention intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

5. Treatment

The present invention also encompasses a method of treating a patient suffering from a condition associated with PI-3 kinase activity. The PI-3 kinase activity may be abnormal, excessive, or constitutively active. The present invention also encompasses a method for treating inflammatory disease comprising administering to a patient in need thereof a therapeutically effective amount of a compound of the present invention. Such diseases and adverse health effects attributable to inappropriate PI-3 kinase signaling activity have been disclosed in the art, for example U.S. 2002/0150954A1; U.S. Pat. No. 5,504,103; U.S. Pat. No. 6,518,277B1; U.S. Pat. No. 6,403,588; U.S. Pat. No. 6,482,623; U.S. Pat. No. 6,518,277; U.S. Pat. No. 6,667,300; U.S.20030216389; U.S.20030195211; U.S.20020037276 and U.S. Pat. No. 5,703,075 the contents of which are incorporated by reference.

The present invention also encompasses a method for enhancing p53 mediated programmed cell death comprising administering to a patient in need thereof a therapeutically effective amount of a compound of the present invention.

The present invention also encompasses a method for enhancing the chemosensitivity of tumor cells comprising administering to a patient in need thereof a therapeutically effective amount of a compound of the present invention.

The present invention also encompasses a method for enhancing the radiosensitivity of tumor cells comprising administering to a patient in need thereof a therapeutically effective amount of a compound of the present invention.

The present invention also encompasses a method for inhibiting tumor induced angiogenesis comprising administering to a patient in need thereof a therapeutically effective amount of a compound of the present invention.

The present invention also encompasses a method for inhibiting angiogenic processes associated with non-cancer diseases comprising administering to a patient in need thereof a therapeutically effective amount of a compound of the present invention.

The present invention also encompasses a method for treatment of cancer comprising administering to a patient in need thereof a therapeutically effective amount of a compound of the present invention.

The compound may be administered simultaneously or metronomically with other anti-cancer treatments such as chemotherapy and radiation therapy. The term "simultaneous" or "simultaneously" as used herein, means that the other anti-cancer treatment and the compound of the present invention administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at certain frequency relative to repeat administration and/or the chemotherapy regiment.

The chemotherapy treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxycoformycin, mitomycin-c, 1-asparaginase, interferons (preferably IFN-α), etoposide, and teniposide.

Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560–10564; Muhlradt (1997) Cancer Res. 57:3344–3346; Nicolaou (1997) Nature 387:268–272; Vasquez (1997) Mol. Biol. Cell. 8:973–985; and Panda (1996) J. Biol. Chem 271:29807–29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17.alpha.-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

A variety of cancers may be treated according to the present invention including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

Most preferably, the invention is used to treat accelerated or metastatic cancers of the bladder, pancreatic cancer, prostate cancer, non-small cell lung cancer, colorectal cancer, and breast cancer.

The present invention also encompasses a method for treating pancreatitis comprising administering to a patient in need thereof a therapeutically effective amount of a compound of the present invention. As discussed in Gukovsky et al., Gastroenterology, 126(2):554–66 (2004), inhibition of PI-3 kinase may prevent pancreatitis.

The present invention also encompasses a method for treating ulcers comprising administering to a patient in need thereof a therapeutically effective amount of a compound of the present invention. The present invention also encompasses a method for treating gastric cancer, such as stomach cancer, comprising administering to a patient in need thereof a therapeutically effective amount of a compound of the present invention. As discussed in Bacon et al., Digestive Disease Week Abstracts and Itinerary Planner, Vol. 2003, Abstract No. M921 (2003) and Rokutan et al., Digestive Disease Week Abstracts and Itinerary Planner, Vol. 2003, Abstract No. 354 (2003), PI-3 kinase is involved in the adhesion of Helicobacterpylori to gastric cells. Furthermore, Osaki et al., Journal of Cancer Research and Clinical Oncology, 130(1): 8–14 (2004) indicates that a PI-3 kinase inhibitor, such as LY294002, may be useful as an anti-tumor agent for gastric carcinoma.

The present invention also encompasses a method of improving the performance of a stent comprising administering a therapeutically effective amount of a compound of the present invention to a patient with a stent, such as a cardiovascular stent. As discussed in Zhou et al., Arteriosclerosis Thrombosis and Vascular Biology, 23(11): 2015–2020 (2003), inhibition of PI-3 kinase may prevent the "stretch" damage that accompanies stent placement in vessels. The compounds of the present invention in the stent or polymer matrix thereof may improve solubility in the stent coating matrix, improve aqueous/serum solubility, or improve perfusion into the cells immediately adjacent to the stent placement.

The present invention also encompasses a method for treating age-related macular degeneration (AMD) comprising administering to a patient in need thereof a therapeutically effective amount of a compound of the present invention. As discussed in Retina, Feb. 18, 2004, inhibition of VEGF inhibits blood vessel overgrowth associated with AMD. The compounds of the present invention may treat AMD by inhibiting angiogenesis.

The present invention also encompasses a method for treating hypertension comprising administering to a patient in need thereof a therapeutically effective amount of a compound of the present invention. As discussed in Northcott and Watts, Hypertension, 43(1): 125–130 (2004), inhibition of PI-3 kinase may prevent the low extracellular concentrations of $Mg^{2+}$ that are associated with hypertension.

The present invention also encompasses a method for suppressing differentiation of progenitor cells, such as myeloid progenitor cells, comprising adding an effective amount of a compound of the present invention to progenitor cells. As discussed in Lewis et al., Experimental Hematology, 32(1): 36–44 (2004), inhibition of the PI-3 kinase pathway suppresses myeloid progenitor cell.

The present invention also encompasses a method for treating liver cancer comprising administering to a patient in need thereof a therapeutically effective amount of a compound of the present invention. As discussed in Leng et al., Hepatology 38(4) Suppl 1: 401A (2003), LY294002 inhibits phosphorylation of Akt (serine/threonine protein kinase B), which is an indicator in human liver tissues.

The present invention also encompasses a method for treating conditions associated with a mutant PTEN comprising administering to a patient in need thereof a therapeutically effective amount of a compound of the present invention. PTEN is a tumor suppressor gene located on chromosome 10q23 that has been identified in patients with Cowden disease. As discussed in Vega et al., Journal of Investigative Dermatology, 121(6): 1356–1359 (2003), mutant PTEN has reduced ability to inhibit the activation of the proto-oncogene Akt. Inhibitors of PI-3 kinase may inhibit phosphorylation of Akt, thereby reducing the effect of the mutant PTEN.

a. Administration

Compositions of the present invention may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. The compositions of the present invention may also be administered in the form of an implant, which allows slow release of the compositions as well as a slow controlled i.v. infusion.

b. Dosage

A therapeutically effective amount of the compound required for use in therapy varies with the nature of the condition being treated, the length of time that activity is desired, and the age and the condition of the patient, and is ultimately determined by the attendant physician. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more subdoses per day. Multiple doses often are desired, or required.

A number of factors may lead to the compounds of the present invention being administered at a wide range of dosages. When given in combination with other therapeutics, the dosage of the compounds of the present invention may be given at relatively lower dosages. In addition, the use of targeting agents may allow the necessary dosage to be relatively low. Certain compounds of the present invention may be administered at relatively high dosages due to factors including, but not limited to, low toxicity, high clearance, low rates of cleavage of the tertiary amine. As a result, the dosage of a compound of the present invention may be from about 1 ng/kg to about 100 mg/kg. The dosage of a compound of the present invention may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

The present invention has multiple aspects, illustrated by the following non-limiting examples.

EXAMPLE 1

Preparation of LY294002

A 10 g sample of LY294002 was prepared according to Scheme 2 based on the procedure described in Vlahos et al., J. Biol. Chem. 269(7): 5241 (1994), the contents of which are incorporated by reference. The displacement of the thiomethyl group of thoichromones such as 12 by amines has been described previously (Bantick et al., J. Heterocyclic Chem, 18:679 (1981), the contents of which are incorporated by reference) as has the cyclization of methyl phenyl ketones such as 11 with carbon disulfide with concomitant alkylation of the thiol anion (Vlahos et al. and Bantick et al.). Preparation of methyl ketones (e.g., 11) in a one-step reaction from the carboxylic acid (10) was performed using the procedure described in Rubottom et al., J. Org. Chem., 48:1550 (1983), the contents of which are incorporated by reference.

SCHEME 2

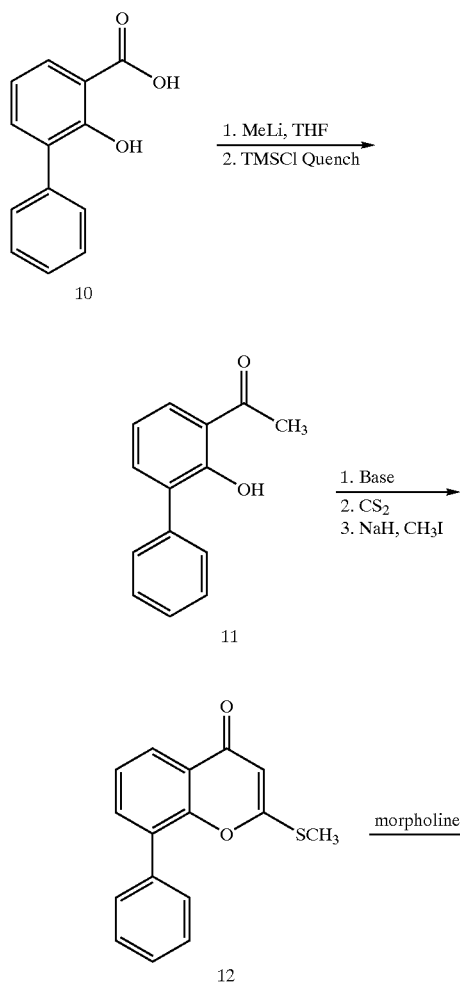

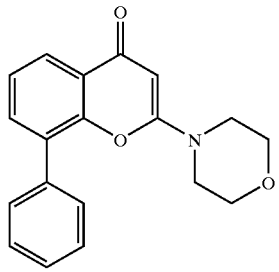

LY294002
(Compound 1)

EXAMPLE 2

Preparation of Quaternary Analogs of LY294002

Following the procedure of Scheme 3 the tertiary amine of LY294002 was quaternized using iodomethane or benzyl chlorides under forcing conditions to yield compounds A052-10 and Compound 13B. Example 56 describes the synthesis of methyl quaternary prodrug A052-10. Example 57 describes the synthesis of a phthalimido quaternary prodrug A052-08. Example 58 describes the synthesis of a paracarboxy benzyl quaternary A044-78. [0199][0215] describes the synthesis of a para-scn-benzyl quaternary prodrug A044-80.

SCHEME 3

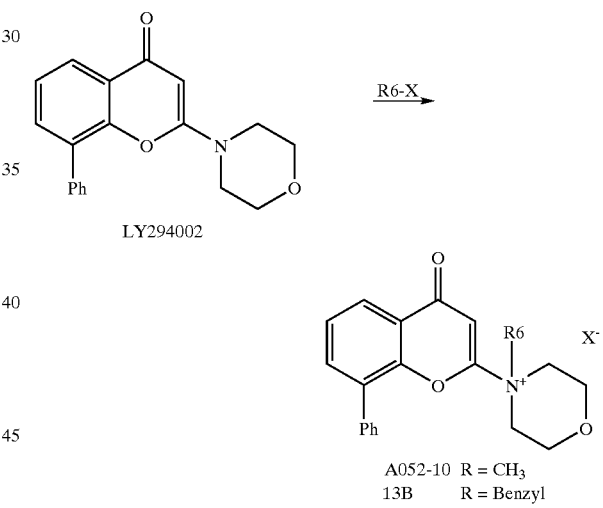

A052-10 R = CH$_3$
13B R = Benzyl

EXAMPLE 3

Preparation of Chloromethyl Esters

Chloromethyl intermediates were prepared following the procedure described in Tsujihara, Synth Commun, 24, 767, 1994. Briefly, the appropriate carboxylic acid was diluted in a 50/50 mixture of dichloromethane/water. The mixture was cooled in an ice-water bath and sodium bicarbonate (4 equiv) and n-tetrabutyl ammonium hydrogen sulfate (0.05 equiv) was added. After stirring for 5 min, chloromethyl chlorosulfate (1.1 equiv) was added. The solution was stirred vigorously overnight. The mixture was transferred to a separatory funnel with more dichloromethane and washed with saturated sodium chloride solution. The organics were dried over sodium sulfate and the solvent removed to provide the product. The material was characterized by LC-MS and in some cases by 1H NMR spectroscopy. By this general procedure the following representative chloromethyl esters were prepared from the corresponding carboxylic acids:

TABLE 1
| STRUCTURE | REF. NO. | RET TIME* | SM RET TIME** |
|---|---|---|---|
| 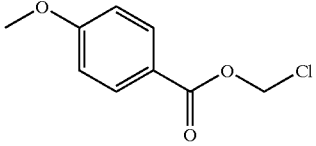 | A029-42 | 3.612 | 2.329 |
| 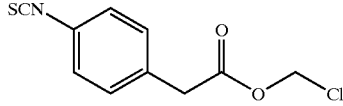 | A029-44 | 4.273 | 3.327 |
| 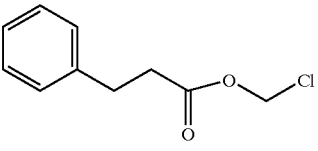 | A029-58 | 3.820 | 2.833 |
| 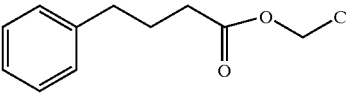 | A029-60 | 4.077 | 2.956 |
| 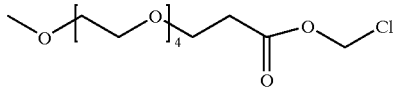 | A029-62 | UD | UD |
| 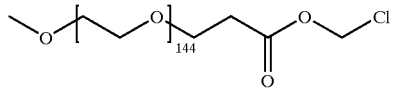 | A029-72 | UD | UD |
| 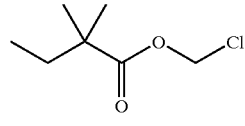 | A029-80 | UD | UD |
| 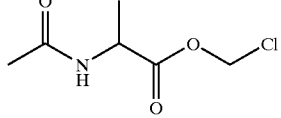 | A029-82 | UD | UD |
| 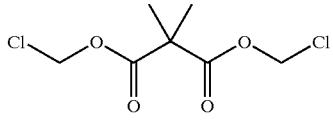 | A029-86 | UD | UD |
| 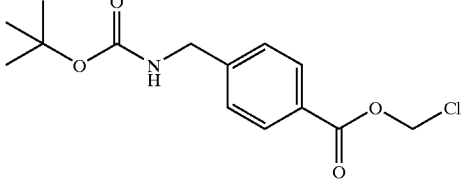 | A040-46 | 3.906 | 2.901 |

TABLE 1-continued

| STRUCTURE | REF. NO. | RET TIME* | SM RET TIME** |
|---|---|---|---|
| 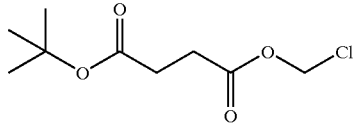 | A040-58 | UD | UD |

*HPLC-MS retention time using UV detection;
**HPLC-MS retention time of the starting carboxylic acid using UV detection;
UD = undetectable due to lack of UV absorbance and no ionization by MS

EXAMPLE 4

Conversion of LY294002 to Quaternary Prodrug

LY294002 (Compound 1) was dissolved in acetonitrile and then each of the chloromethyl esters (1–1.5 equiv) from Example 3 was added along with 1–2 equivalents of sodium iodide. At room temperature, the reaction proceeded only slowly with the chloromethylesters to give very small amounts of the quaternized amine product along with the precipitation of sodium chloride. At 65° C., the reaction proceeded to completion usually in in 4 hours. The reaction when complete (as judged by analysis by LC-MS) was filtered; concentrated and then purified on reverse phase HPLC. The fractions were collected and lyophilized to give the desired products as fluffy powders. Examples prepared and purified in this manner are shown in the table below (the counter anions are not displayed but included chloride, iodide, acetate or mixtures thereof).

TABLE 2

| STRUCTURE | MW | ELS RET | MS | REF NO | YIELD (mg) | PURITY |
|---|---|---|---|---|---|---|
| 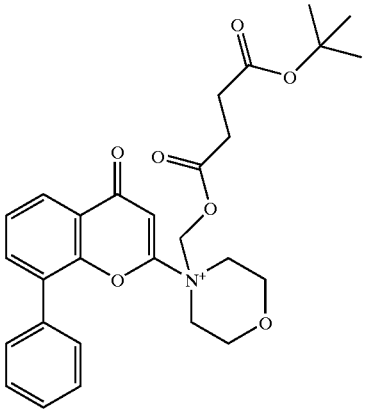 | 494.6 | 2.718 | M+ = 494 | A041-49 | 400.6 | 93% |
| 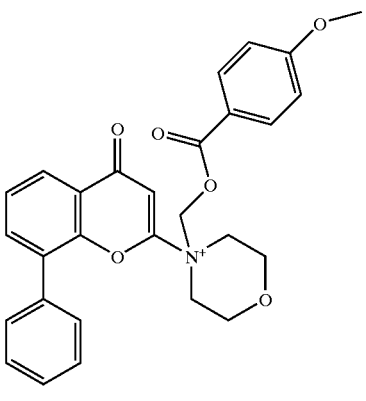 | 472.5 | 2.661 | M+ = 472 | A023-23 | 145 | 90% |

TABLE 2-continued

| STRUCTURE | MW | ELS RET | MS | REF NO | YIELD (mg) | PURITY |
|---|---|---|---|---|---|---|
| (structure with NCS group) | 5134.6 | 3.019 | M+ = 513 | A036-48B | 194.1 | 97% |
| (structure with phenylpropanoate) | 470.6 | 2.724 | M+ = 470 | A031-11 | 190.4 | 98.6% |
| (structure with phenylbutanoate) | 484.6 | 2.926 | M+ = 484 | A031-14 | 204.8 | 98.5% |
| (structure with dimethylbutanoate) | 436.5 | 2.800 | M+ 436 | A028-81 | 31 | 90% |

TABLE 2-continued

| STRUCTURE | MW | ELS RET | MS | REF NO | YIELD (mg) | PURITY |
|---|---|---|---|---|---|---|
| 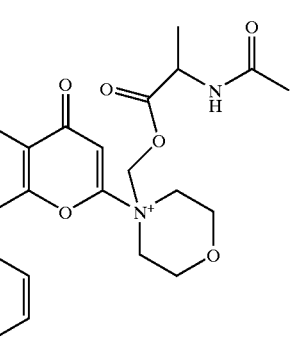 | 451.5 | 2.082 | M+ = 451 | A029-92 | | |
| 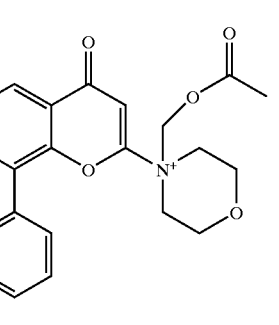 | 380.4 | 2.204 | M+ = 380 | A040-70 | 264.0 | 97% |
| 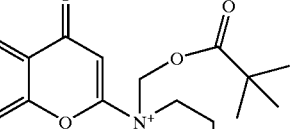 | 422 | 2.735 | M+ = 422 | A045-09 | 102.3 | 93.7% |

EXAMPLE 5

Halomethyl Ester Linkers

Based on the results of Example 3 and Example 4, halomethyl ester linkers were prepared (Scheme 4 and chart). Compound B was prepared from Compound A (commercially available) as described in Example 3. This compound was converted into the more reactive iodomethyl ester (Compound C) by a Finklestein reaction by dissolving in acetone or 2-butanone and then dissolving 2–5 equivalentss of sodium iodide whereupon the sodium chloride precipitated and the iodomethyl ester (Compound C) was produced in solution. Compound C was isolated by stripping off the solvent and dissolving in a water immiscible solvent such as methylene chloride and extracting with water to remove the residual sodium iodide.

Compound E was prepared from Compound D (commercially available) Compounds F and G were prepared in a manner similar to the production of Compounds B and C, respectively.

SCHEME 4

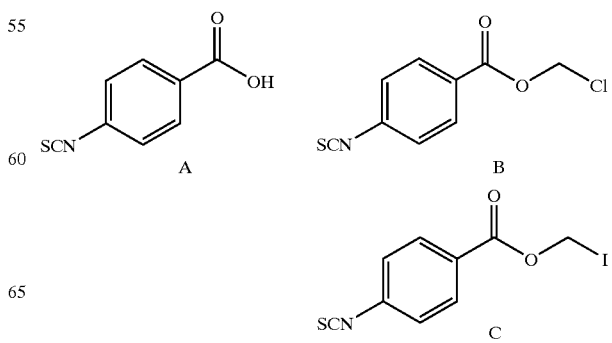

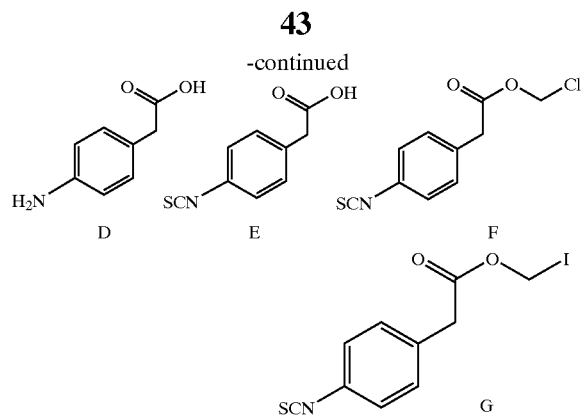

EXAMPLE 6

Quaternization of LY294402 with Halomethyl Linkers

Halomethyl esters, including those of Example 5, were use to quaternize LY294002 using conditions similar to the methodology in Example 4. Representative prodrugs comprising a linker with a free functional group include the following:

Compound 1104

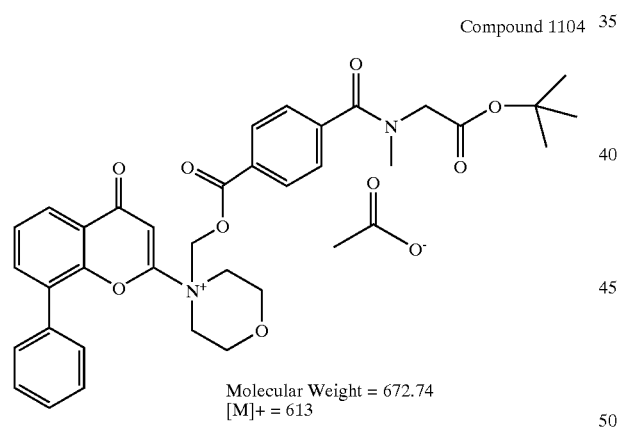

Molecular Weight = 672.74
[M]+ = 613

Compound 1105

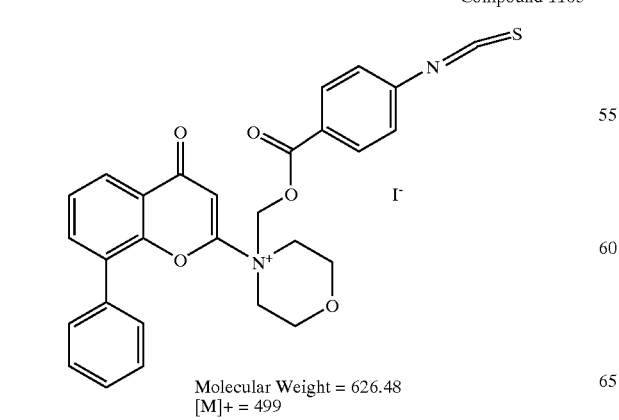

Molecular Weight = 626.48
[M]+ = 499

Compound 1106

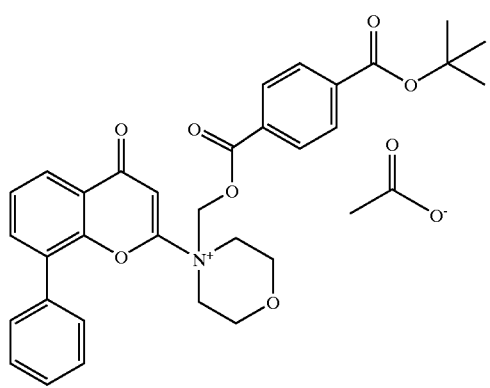

Molecular Weight = 601.66
[M]+ = 542

Compound 1107

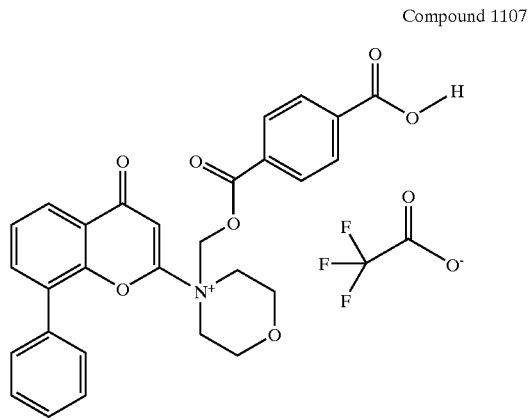

Molecular Weight = 599.53
[M]+ = 486

Compound 1108

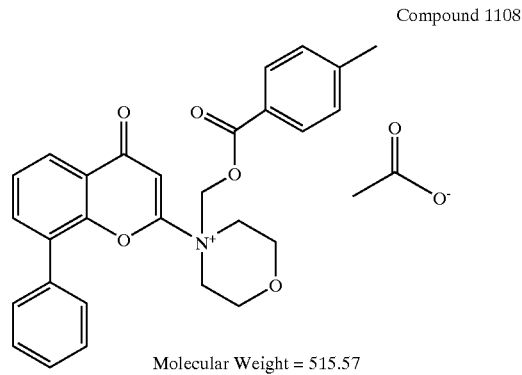

Molecular Weight = 515.57
[M]+ = 456

Compound 1109

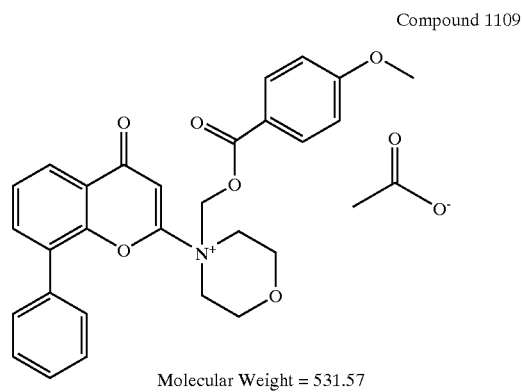

Molecular Weight = 531.57
[M]+ = 472

Compound 1110

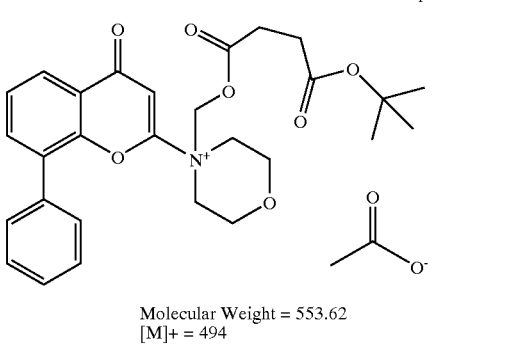

Molecular Weight = 553.62
[M]+ = 494

Compound 1105 was prepared by mixing Compound 1101 with compound C in acetonitrile where both are soluble and the product Compound 1105 precipitates out over a three day period and is washed with a small amount of acetonitrile to give substantially pure Compound 11105 (confirmed by LCMS).

EXAMPLE 7

Preparation of Prodrugs Using Compound 1111

Compound 111111 was produced by the method shown in Scheme 5. Compound 11110 was treated with neat trifluoroacetic acid for 1–3 hours and the TFA was blown off with argon and dried under vacuum to give a glassy solid comprised of Compound 1113. Compound 1113 was then dissolved in 1–3 ml of thionyl chloride and heated at 65° C. for 3–8 hours. The thionyl chloride was blown off with argon and then dried under high vacuum to give Compound 1111 in good yields as a glassy yellow solid. Compound 1111 can be reacted as a typical acid chloride with various nitrogen-containing and hydroxyl-containing nucleophiles for example by simply dissolving in methanol to give the corresponding methyl ester Compound 1112.

SCHEME 5

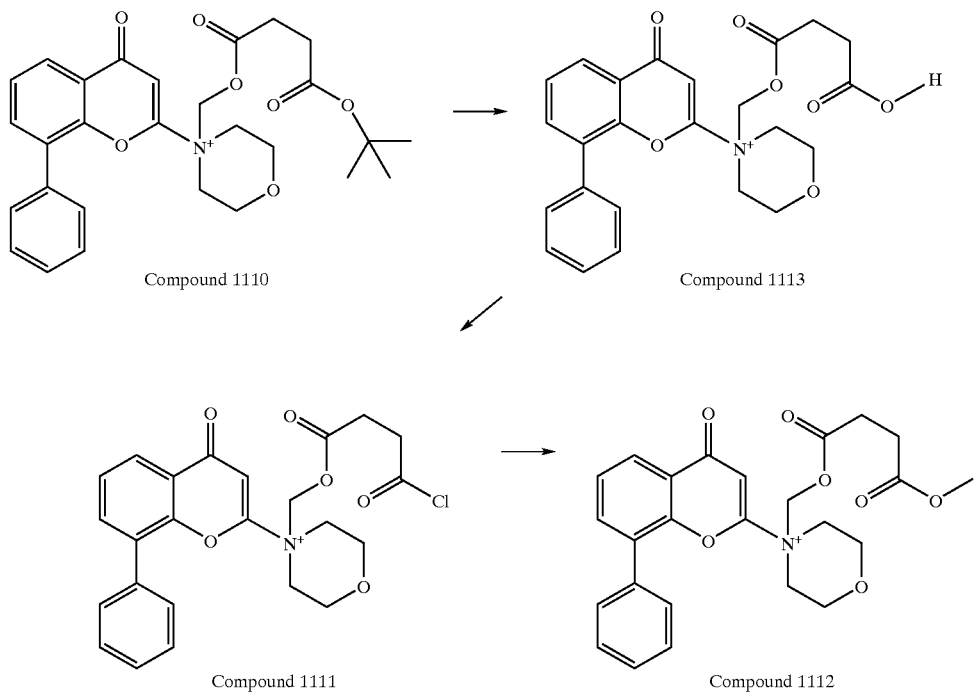

Compound 1110

Compound 1113

Compound 1111

Compound 1112

A sample of Compound 1111 was dissolved in acetonitrile and treated with at least 5 equivalents of different alcohols in separate vials. After 1 hour the samples were analyzed by HPLC-MS and showed good conversion >90% of Compound 1111 to the corresponding ester as shown and characterized in Table 3.

TABLE 3

| Structure of Ester Formed | Ref No | MW | Retention Time (minutes)* | MS+ Found |
|---|---|---|---|---|
| 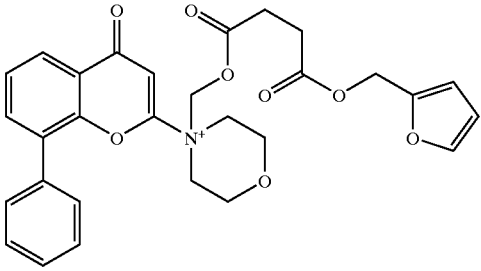 | A046-92-1 | 518.55 | 2.849 | 518 |
| 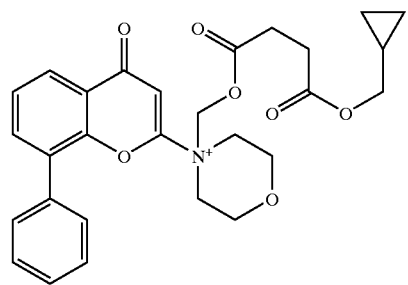 | A046-92-2 | 492.55 | 2.788 | 492 |
| 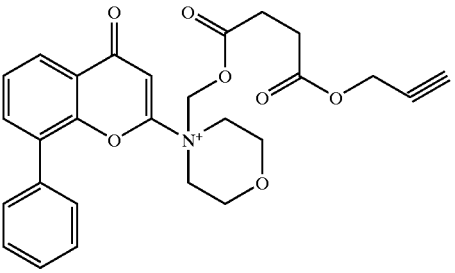 | A046-92-3 | 476.51 | 2.640 | 476 |
| 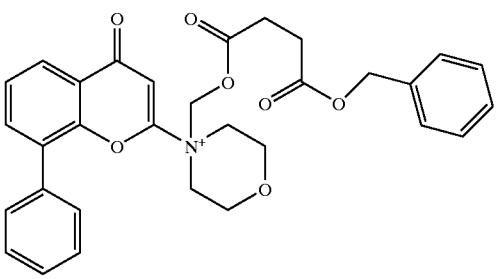 | A046-92-4 | 528.59 | 2.970 | 528 |
| 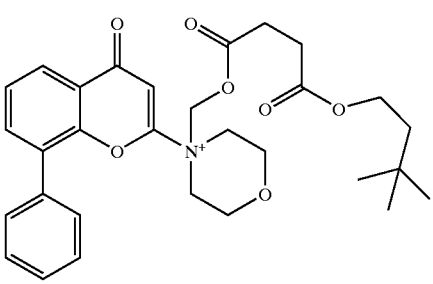 | A046-92-5 | 522.62 | 3.197 | 522 |

TABLE 3-continued

| Structure of Ester Formed | Ref No | MW | Retention Time (minutes)* | MS+ Found |
|---|---|---|---|---|
| 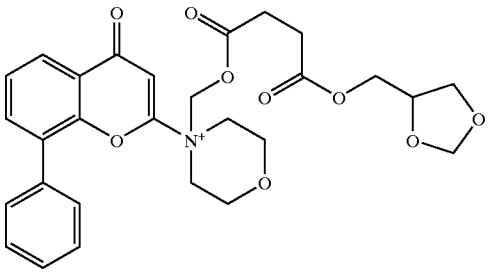 | A046-92-6 | 524.55 | 2.490 | 524 |
| 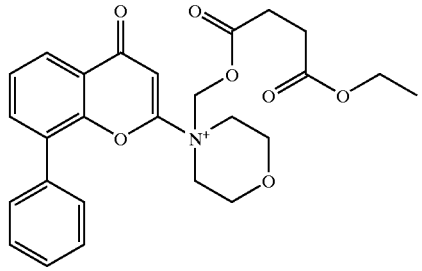 | A046-92-7 | 466.52 | 2.632 | 466 |
| 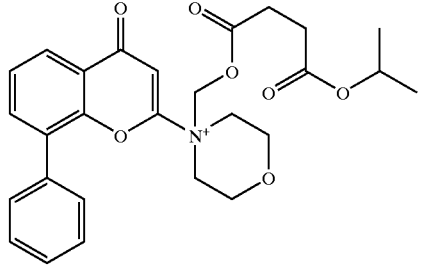 | A046-92-8 | 480.54 | 2.787 | 480 |

*UV 214 nm

EXAMPLE 8

Preparation of Protein Conjugate Prodrugs Using Compound 1111

Proteins are conjugated in largely aqueous solution (pH 7–9) (phosphate buffer to carbonate buffer) using an excess a 2–10 fold excess of Compound 1111 relative to the amino groups or hydroxyl groups to be modified. The acid chloride Compound 1111 can be introduced in a mixed organic-aqueous solution (such at 50/50 water/acetonitrile or 50/50 water/THF) or stirred in methylene chloride in a two-phase reaction system at room temperature for 1–24 hours. Protein-conjugates can be purified by dialysis or ultrafiltration and used directly.

A 500 μl aliquot of 5 mg/ml transferrin protein (Sigma) in 50 mM sodium bicarbonate buffer was mixed with 100 up of 30 mM A024-79 (100 molar equivalents), which was prepared according to Example 12, in DMSO. After 1 hour and 20 minutes of reacting at room temperature a 50 up sample was removed and passed through a Sephadex G-10 (700 molecular weight cutoff) column to separate protein from small molecules. An aliquot of the purified conjugated protein eluent was then extracted with acetonitrile and no detectable Compound 1 was observed by LC-MS. The purified conjugated protein eluent was allowed to stand at room temperature 39 hours at which time the protein mix was again extracted with acetonitrile and this time 15% of the maximum theoretical amount of Compound 1 was detected. These results indicate a molar ratio of 15 moles of prodrug were attached per mole of transferrin. These results demonstrated the attachment of an electrophilic linker-bearing prodrug to a representative protein and demonstrated that over time a substantial amount of a PI3 kinase inhibitor (compound 1) was released from the protein under aqueous conditions.

EXAMPLE 9

Preparation of Resin-Bound Prodrugs Using Compound 1111

The peptide arg-gly-asp-ser (RGDS) was prepared on wang resin using standard FMOC/HOBT coupling peptide chemistry using all natural amino acids. The resin-bound peptide was reacted with Compound 1111 in DMF from 1–24 hours, filtered and the resin washed with DMF and then methylene chloride and then treated with trifluoroacetic acid to cleave the conjugate Compound 1126 from the resin (Scheme 6). Example 55 describes a scaled up preparation of Compound 1111.

SCHEME 6

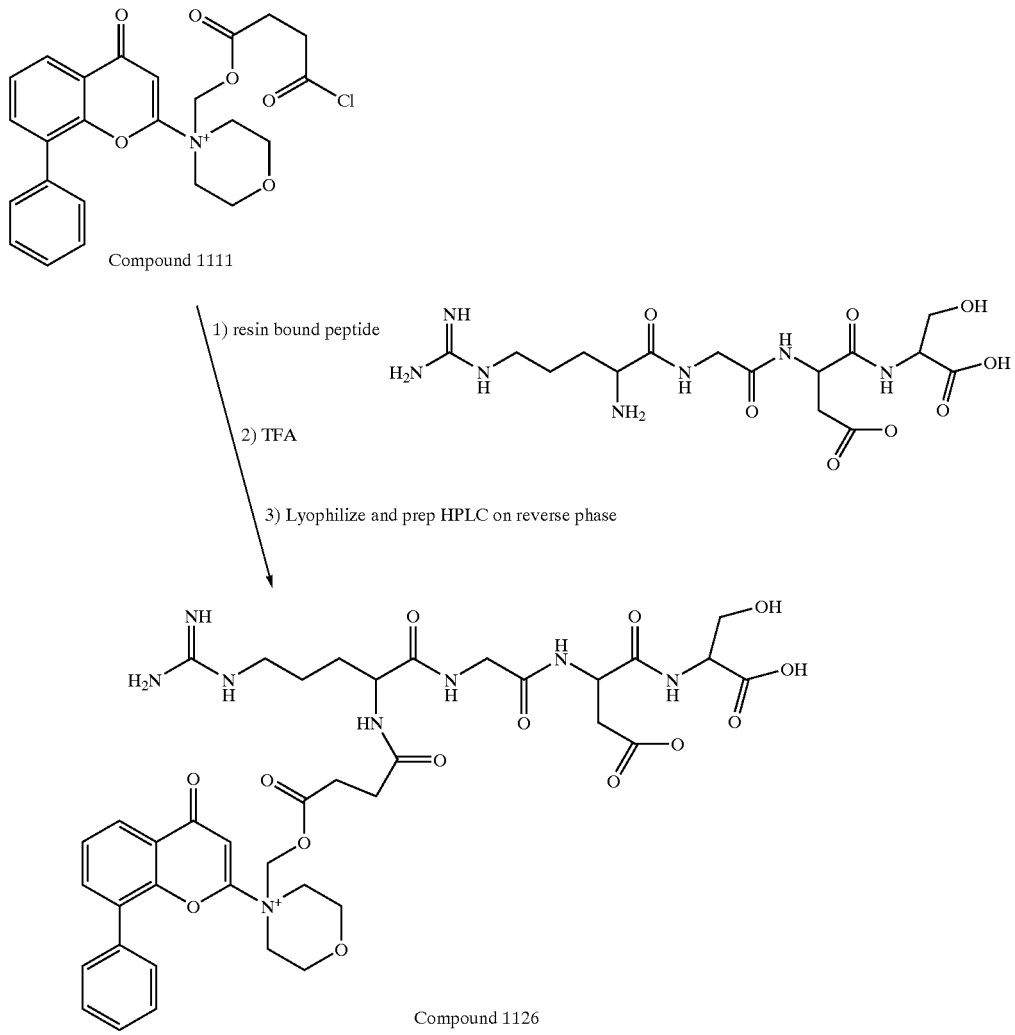

Compound 1111

Compound 1126

EXAMPLE 10

Preparation of Prodrugs with Folate Targeting Agents Using Compound 1111

Compound 1111 has an electrophilic group that may be reacted with nucleophilic amino groups under mildly basic organic or aqueous conditions (i.e. sodium bicarbonate buffer from 20 mM to 500 mM) to form a nonreversible thiourea link. Suitable nucleophilic amino groups are present on the targeting biomolecule folate. Folate molecules A and C were conjugated to Compound 1111 via an amino group in DMF by mixing in roughly equal proportions in the presence of the base triethylamine or diisopropyl ethyl amine to yield compounds B and D (Scheme 7).

SCHEME 7

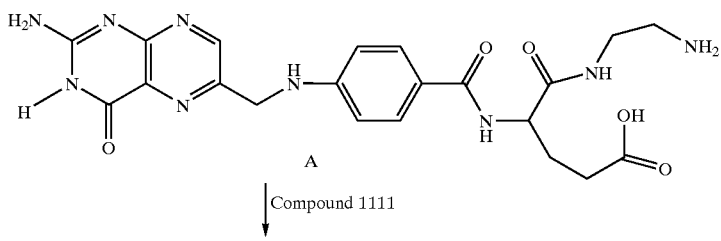

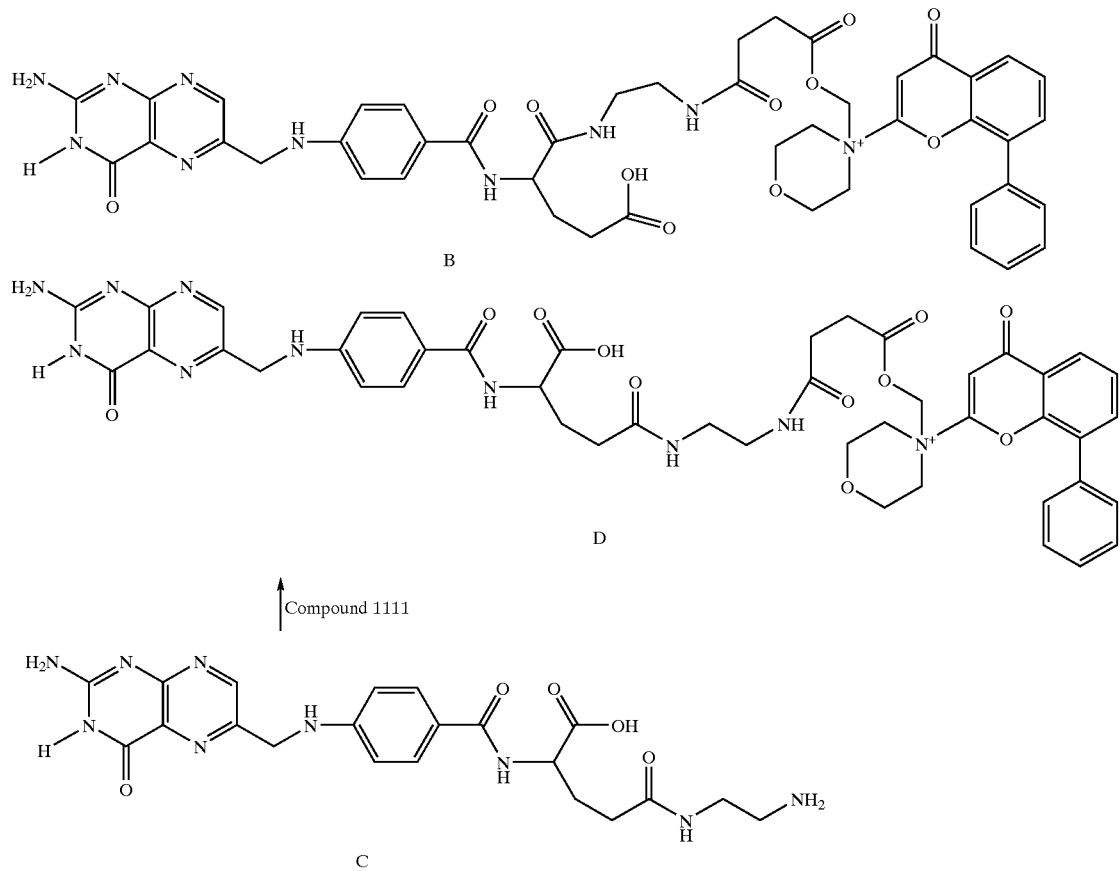

EXAMPLE 11

Preparation of Prodrugs with Antibody Targeting Agents Using Compound 1111

Compound 1111 is conjugated to monoclonal antibodies in aqueous pH 7 to 9 and then separated by ultrafiltration or other standard methods of separating protein conjugates from small molecules. The conjugated performed can be prepared according to Example 8.

EXAMPLE 12

Preparation of Prodrugs Using N-hydroxysuccinimide Esters

An ester less reactive than Compound 1111 was prepared by producing the N-hydroxysuccinimide active ester of Compound 1113 (Scheme 8). A 100 mg sample of Compound 1113 (A024-67) was dissolved in 1 ml of dry THF along with 53 mg of N-hydroxysuccinimide (2 equivalents). With stirring a 45 up aliquot of 1 M dicyclohexycarbodi-imide in methylene chloride (2 equivalents) was added all at once. Within 3 minutes a heavy white precipitate formed indicating the coupling reaction was occurring. After allowing the reaction to stir for 23 hours the reaction mix was filtered and the solvent removed from the filtrate to yield 172 mg of crude active ester product as a thick yellow oil, assigned Compound A024-79 and showing a retention time of 2.334 minutes with the expected mass of M+=535 found for this peak.

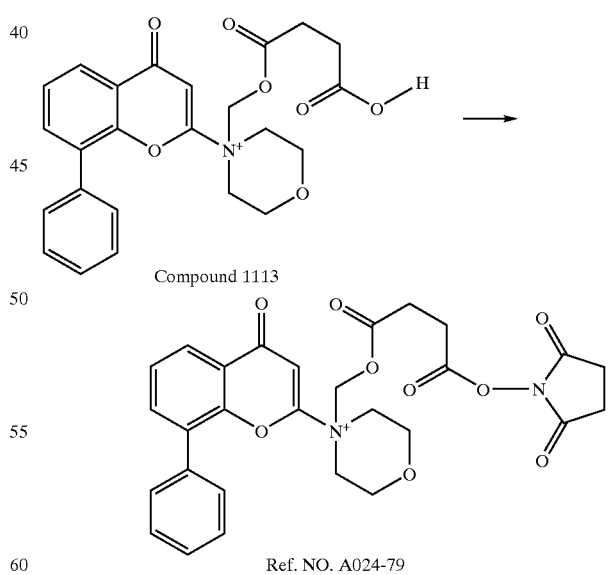

SCHEME 8

Using the same chemistry as described above for Compound 1111, A024-79 was used to conjugate targeting proteins as described in Example 8 and used to conjugate to a polymer is described in Example 74.

EXAMPLE 13

Preparation of Prodrugs Using Compound 1105

Compound 1105 has an electrophilic group that may be reacted with nucleophilic amino groups under mildly basic organic or aqueous conditions (i.e. sodium bicarbonate buffer from 20 mM to 500 mM) to form a nonreversible thiourea link. Suitable nucleophilic amino groups are present on targeting biomolecules such as peptides, proteins and small molecules bearing amine groups such as vitamin derivatives (A and C of Scheme 7). Representative examples of such products include Compounds B and D.

SCHEME 9

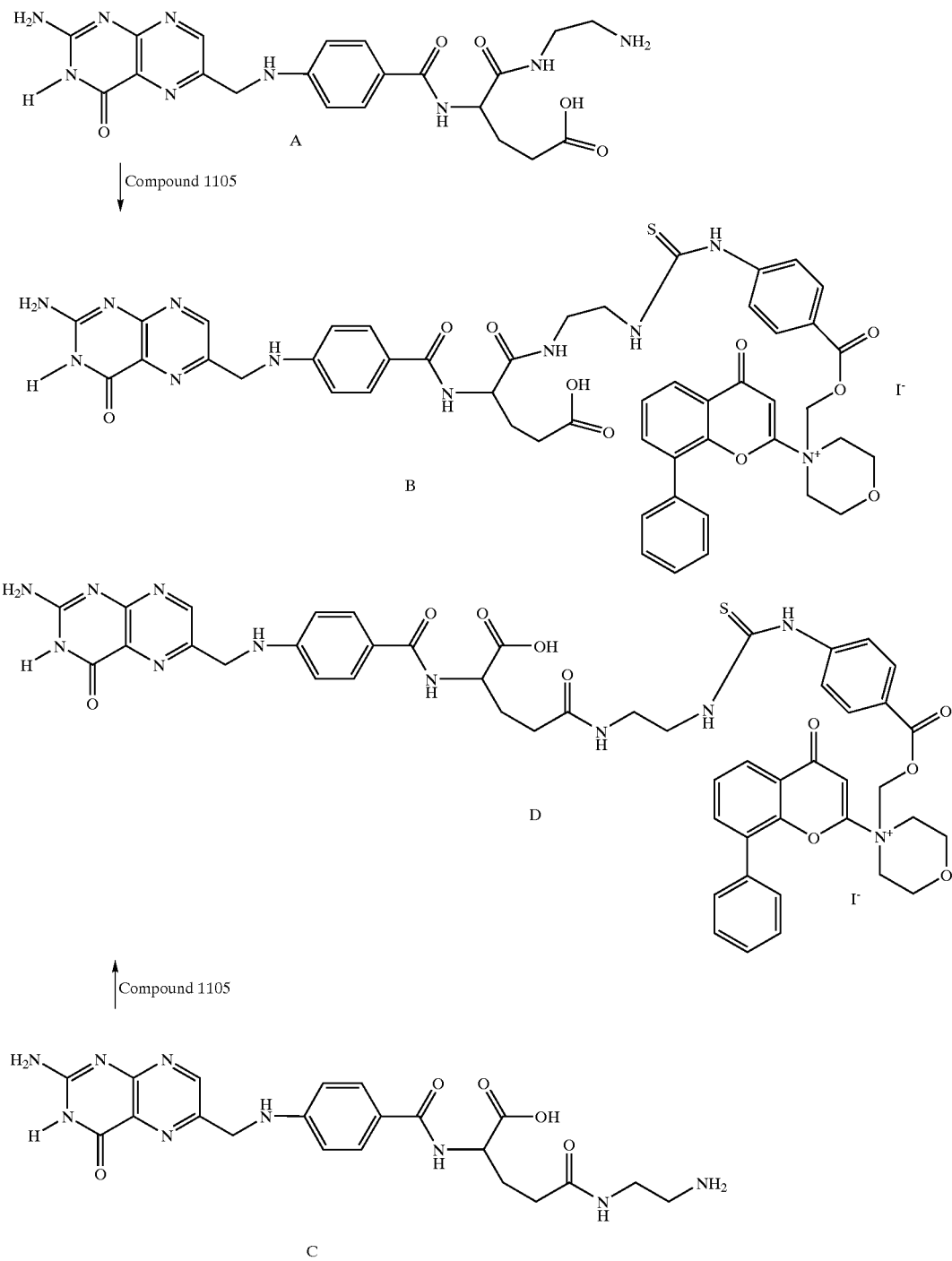

EXAMPLE 14

Preparation of Derivatives of Morpholine Ring

The thiomethyl compound of Scheme 1 was prepared as described in Example 1. This compound was heated in an appropriate solvent with or without a catalytic amount of acetic acid and with an excess of the nucleophilic amine compound until most of the thiomethyl compound was consumed. The mix was then subjected to preparative reverse phase LC-MS to isolate the desired morpholine analog. Compounds prepared in this manner are shown in Table 4 along with their conditions of preparation, characterization and isolation shown in Table 5. The NMR data for the compounds is shown in Table 6.

TABLE 4

| Structure | Compound # | Mol Wt | Yield (mg) | Yield (%) |
|---|---|---|---|---|
| 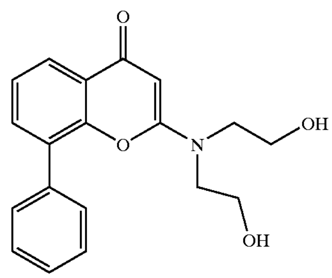 | 1153 | 352.42 | 32.6 | 24.8 |
| 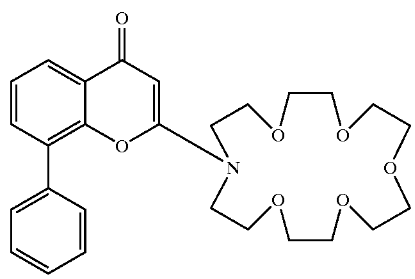 | 1154 | 483.5 | 54.6 | 30.3 |
| 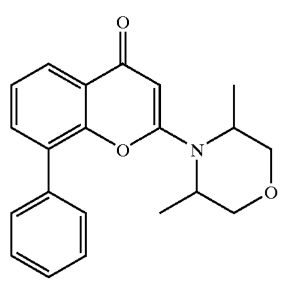 | 1155 | 335.4 | 24.7 | 19.8 |
| 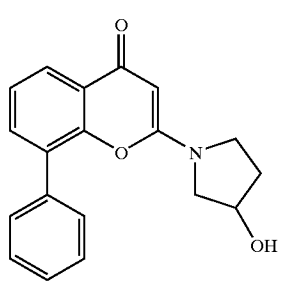 | 1156 | 307.3 | 5.0<br>61.2 | 4.4<br>53.4 |

TABLE 4-continued

| Structure | Compound # | Mol Wt | Yield (mg) | Yield (%) |
|---|---|---|---|---|
| 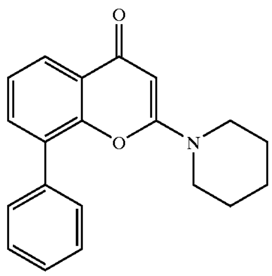 | 1157 | 305.4 | 100 (est) | 87.7 (est)) |
| 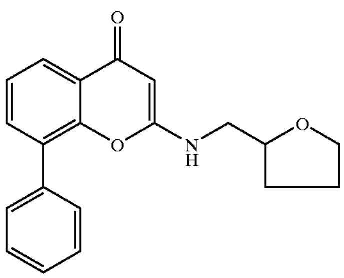 | 1158 | 321.4 | 30 | 25.0 |
| 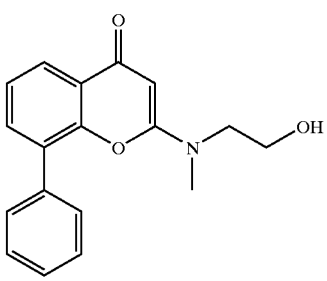 | 1159 | 295 | 62 | 56.4 |
| 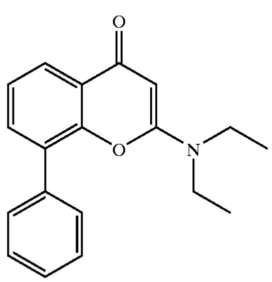 | 1160 | 293.4 | 24.4 | 22.3 |
| 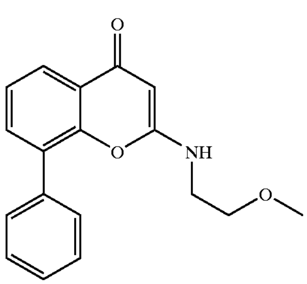 | 1161 | 295.3 | 71 | 64.5 |

TABLE 4-continued

| Structure | Compound # | Mol Wt | Yield (mg) | Yield (%) |
|---|---|---|---|---|
| 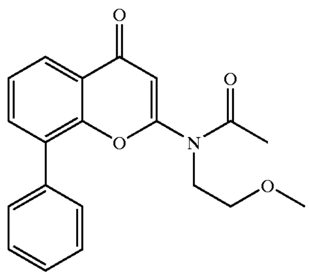 | 1162 | 337.4 | 6.7 | 23.5 |
| 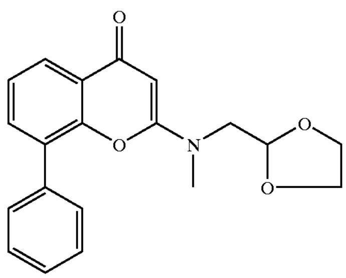 | 1163 | 337.4 | 57.7 | 45.9 |
| 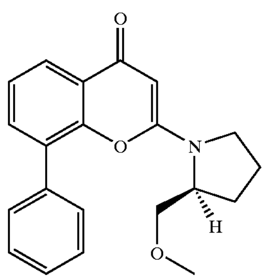 | 1164 | 335.4 | 41.0 | 32.8 |
| 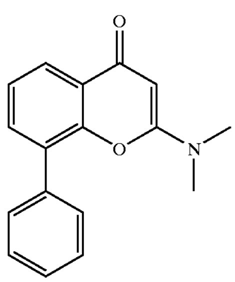 | 1165 | 265.31 | 17.2 | 17.2 |
| 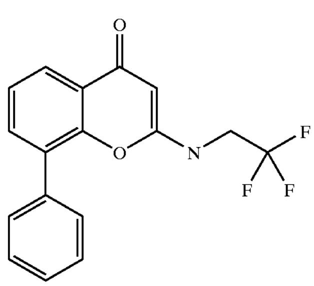 | 1166 | 319.29 | 2.4 | 3.0 |

TABLE 5

| Compound No. | Lot No. (Prep Material) | Solvent | Heat (° C.)/Time (min) | Cat | Retention Time (min) | Yield (mg) | Yield (%) |
|---|---|---|---|---|---|---|---|
| 1153 | A037-36 | n-BuOH | 115/350 | no | 3.407 | 32.6 | 24.8 |
| 1154 | A036-08 | n-BuOH | 110/192 | no | 3.156 | 54.6 | 30.3 |
| 1155 | A037-19-3 | n-BuOH | 110/24 | no | 3.649 | 24.7 | 19.9 |
| 1156 | A037-18-1 | n-BuOH | 110/48 | no | 2.764 | 61.2 | 53.4 |
| 1157 | A037-15 | n-BuOH | 110/24 | no | 3.837 | 100 | 87 |
| 1158 | A037-29 | n-BuOH | 110/4 | no | 2.753 | 30 | 25 |
| 1159 | A037-31 | n-BuOH | 110/20 | no | 2.753 | 62 | 56.4 |
| 1160 | A037-48 | EtOH | 65/220 | yes | 3.666 | 24.4 | 22.3 |
| 1161 | A037-40 | EtOH | 65/48 | yes | 3.012 | 71 | 64.5 |
| 1162 | A037-69 | toluene | 65/24 | — | 3.410 | 28.5 | 23.5 |
| 1163 | A037-99A | n-BuOH | 110/180 | no | 3.278 | 57.7 | 45.9 |
| 1164 | A037-99B | n-BuOH | 110/180 | no | 3.587 | 41 | 32.8 |
| 1165 | A041-32 | n-BuOH/DMF | 110/24 | yes | 3.247 | 17.2 | 17.2 |
| 1166 | A041-25 | n-BuOH | 110/240 | yes | 3.427 | 11.1 | 9.3 |

TABLE 6

1153 $^1$H NMR(CDCl$_3$): δ 1.60–1.65 (b s, 2H), 3.772–3.399 (t, 4H), 3.506–3.533 (t, 4H), 5.474 (s, 1H), 7.367–7.550 (m, 7H), 8.178–8.202 (d, 1H, J=7.9Hz)

1154 $^1$H NMR(CDCl$_3$): δ 3.533–3.644 (m, 4H) 5.491 (s, 1H), 7.370–7.541 (m, 7H) 8.173–8.197 (d, 1H, J=7.76Hz)

1155 $^1$H NMR(CDCl$_3$): δ 1.165–1.187 (d, 6H), 2.567–2.627 (t, 2H), 3.580–3.640 (m, 4H) 5.496 (s, 1H), 7.389–7.591 (m, 7H), 8.164–8.187 (d, 1H, J=7.75Hz)

1157 $^1$H NMR(CDCl$_3$): δ 1.573–1.698 (m, 6H), 3.344–3.370 (t, 4H), 5.543 (s, 1H), 7.37–7.562 (m, 7H), 8.163–8.186 (d, 1H, J=7.8Hz)

1158 $^1$H NMR(CDCl$_3$): δ 1.498–1.547 (m, 7H), 1.873–1.997 (m, 3H), 2.600–3.200 (b, 1H), 3.140–3.160 (m, 1H), 3.316–3.323 (m, 1H), 3.737–3.831 (m, 2H), 4.011–4.037 (m, 1H), 5.624 (s, 1H), 7.387–7.582 (m, 7H), 8.163–8.187 (d, 1H, J=7.8Hz)

1159 $^1$H NMR(CDCl$_3$): δ 1.5–2.3 (b s, 2H), 3.015 (s, 3H), 3.400–3.426 (t, 2H), 3.674–3.741 (t, 2H), 5.412 (s, 1H), 7.287–7.325 (t, 1H), 7.404–7.489 (m, 6H), 8.066–8.090 (d, 1H, J=7.75Hz)

1160 $^1$H NMR(CDCl$_3$): δ 1.077–1.178 (t, 6H), 3.255–3.308 (q, 4H), 5.447 (s, 1H), 7.367–7.546 (m, 7H), 8.180–8.204 (d, 1H, J=8.01Hz)

1161 $^1$H NMR(CDCl$_3$): δ 3.326–3.358 (t, 2H), g 3.358 (s, 3H), g 3.517–3.542 (t, 2H), g 5.099 (b s, 1H), g 5.427 (s, 1H), g 7.373–7.565 (m, 7H), g 8.172–8.195 (d, 1H, J=7.74Hz)

1163 $^1$H NMR(CDCl$_3$): δ 3.035 (s, 3H), g 3.479–3.488 (d, 2H), g 3.806–3.888 (m, 4H), g 4.961–4.980 (t, 1H), g 5.566 (s, 1H), g 7.385–7.489 (m, 4H), g 7.555–7.586 (m, 3H), g 8.180–8.204 (d, 1H, J=8.05Hz)

1164 $^1$H NMR(CDCl$_3$): δ 1.931–2.103 (m, 4H), g 3.133–3.248 (b s, 5H), g 3.273–3.296 (m, 1H), g 3.368–3.394 (m, 1H), g 3.990–3.999 (b s, 1H), g 5.403 (s, 1H), g 7.374–7.556 (m, 7H), g 8.191–8.215 (d, 1H, J=7.81Hz)

EXAMPLE 15

HPLC Analysis

HPLC analysis was performed on a Shimadzu LCMS-2010 and employed a flow rate of 3 ml/min and a starting B concentration of 5%. The B solvent was linearly ramped to 95% concentration at 5.0 minutes, held at 95% until 6.0 minutes, then linearly ramped back down to 5% at 6.5 minutes, where it remains until the end of the run at 7.5 minutes. Unless otherwise noted this is the method used in the examples. Method B is a slow gradient method for polar compounds that employs a flow rate of 3 ml/min and a starting B concentration of 0%, where it is held for the first minute. The B solvent is linearly ramped to 10% concentration at 3.0 minutes, then linearly ramped to 95% at 5.0 minutes, where it is held until 6.0 minutes, and then linearly ramped to 5% at 6.5 minutes, where it remains until the end of the run at 7.5 minutes. In addition to mass detection the LC detection consisted of 3 channels; UV absorbance at 254 nm, bance at 214 nm, and evaporative light scattering (Alltech ELSD 2000). The evaporative light scattering detector was run at 50° C. with a nitrogen flow of 1.5 liters per minute. The CDL (chemical desolvation line) and block temperatures of the Shimadzu LCMS-2010 were both 300° C., and the nitrogen nebulizer gas flow was 4.5 L/min. Positive and negative mass spectra were detected from 50 to 2000 m/z. The column was a YMC CombiScreen ODS-AQ, S-5µ particle size, 50 mm long with a 4.6 mm I.D. Mobile phase A was made using HPLC grade B&J water with 0.1% (v/v) HOAc added and mobile phase B was HPLC grade B&J acetonitrile with 0.1% (v/v) HOAc added. This system gives a retention time of 1.50 to 1.60 minutes ($t_R$=1.50–1.60) for a standard commercially available material (4-hydroxyphenylacetic acid; Aldrich Catalog H5000-4; m.p. 149–151° C.) used as a reference standard.

EXAMPLE 16

Preparative HPLC

Gradient Preparative HPLC was performed on a Shimadzu system composed of two LC-8A pumps connected to a SIL-10A autosampler and eluting over a reverse phase column (YMC, cat CCAQSOSO52OWT; ODS-AQ CombiPrep, 20 mm×50 mm) and then passing through an MRA variable volume splitter; the smaller stream was then made up to 3 ml/minute using a LC-10 ADVP make-up pump (MeOH) and the eluent passed through a variable two channel wavelength UV detector and then split roughly 6:1 to an evaporative light scattering detector (run at 50 C with a nitrogen flow of 1.5 liters per minute) and a Shimadzu 2010 Mass detector; the larger stream from the MRA splitter then flowed to a Gilson 215 liquid handler serving as a fraction collector triggered by mass, UV absorbance, or ELS peak size.

Different gradients were run always starting with the more aqueous solvent A and ramping up to various concentrations of B. Mobile phase A was made using HPLC grade B&J water with 0.1% (v/v) HOAc added and mobile phase B was HPLC grade B&J acetonitrile with 0.1% (v/v) HOAc added.

EXAMPLE 17

Bioactivity of Hydrolyzed Prodrugs

The bioactivity of LY294002 (Compound 1) was determined by assaying phagocytosis in J774 macrophages, which is a class I PI-3 kinase-dependent pathway. Briefly, J774 cells are treated with LY294002 at concentrations of 10, 1 and 0.1 μM along with an appropriate DMSO control for 1 h in DMEM with 10% FCS and then sensitized sRBCs (sheep red blood cells) was added at a target to effector ratio equal to 100:1 for 30 minutes at 37° C. Cells were exposed to hypotonic shock to remove red blood cells and phagocytosis was determined by measurement of hemoglobin concentration in the cell lysates. As shown in FIG. 1, LY294002 significantly blocked phagocytosis at all concentrations in a dose dependent manner. These results indicate that the J774 cell system can be used to rapidly and easily assay the ability of the compounds of the present invention to inhibit PI-3 kinase activity. Using this method of assaying PI-3 kinase activity targeted prodrug compound 1126 was tested at 5 μM concentration with variable preincubation time to allow for in situ conversion of prodrug to active drug (compound 1). The control sample (time zero with no preincubation of compound 1126) showed a phagocytic index (PGI; a measure of the degree of phagocytosis occurring as a result of not inhibiting PI-3 kinase) of 140 whereas compound 1126 with an aqueous pH=7 incubation time of 2, 5, and 10 hours showed PGI of 88, 78, and 37 respectively. This example demonstrates that initially prodrug 1126 has little to no PI-3 kinase inhibition activity and over time is converted to bioactive drug that does show significant PI-3 kinase inhibition. Another experiment showed that a 20 uM concentration of compound 1126 in an exposure-limited setting (20 minute exposure to test solution then removal of test solution) had a PGI of 50 versus 163 for solvent blank, 190 for compound 1, and 170 for RGDS (tetrapeptide that is the targeting moiety of compound 1126). This example showed the advantages of a targeted PI-3 kinase inhibitor in an exposure-time-limited setting. This effect was further evaluated by repeating the experiment using decreasing doses of compound 1126 which showed that 10 uM, 3 uM, 1 uM, and 0 uM for a 20 minute incubation time followed by removal of the compound and then 2 hours incubation for phagocytosis to occur gave PGIs of 33, 143, 206, and 213 respectively. This example demonstrates the compound 1126 in a dose-exposure-limited setting inhibited PI-3 kinase in a dose dependent manner.

EXAMPLE 18

Preparation Of Bone Targeting Group A030-84

A solution of 500 mg 4-[(N-BOC)aminoethyl]aniline (Aldrich) in 10 ml dioxane was treated with paraformaldehyde (400 mol %, 270 mg) and trimethylphosphite (400 mol %, 1.12 g). The mixture was heated to 95° C. overnight. Then more paraformaldehyde (270 mg) and trimethylphosphite (1.12 g) were added and it was heated at 95° C. overnight again. The solution was cooled, taken up in chloroform (20 mL) and washed with saturated sodium chloride (20 mL) and water (20 mL). The organics were dried over sodium sulfate and the solvent and excess trimethylphosphite removed via rotary evaporation at 80° C. to provide 1.723 g of a clear oil. The presence of the title compound assigned lot number A030-74 was confirmed by electrospray HPLC-MS showing a retention time of $t_R$=2.9 minutes and a mass of 467 m/z [M+H]+ and 489 m/z [M+Na]+ found for the desired mass [M=$C_{18}H_{32}N_2O_8P_2$].

A solution of 870 mg of A030-74 as prepared above in 10 mL dichloromethane was treated with bromotrimethylsilane (690 mol %, 1.97 g). The solution was stirred overnight. Methanol (10 mL) was added and the solution was stirred 15 min and then concentrated to provide 1.12 g of an orange oil. The presence of the title compound was confirmed by electrospray LC-MS. The retention time using this gradient was found to be $t_R$=0.85 minutes and the mass spec for the desired product [M=$C_9H_{16}N_2O_6P2$] found at the expected m/z 309 [M−H]⁻ operating in the negative mode. This product was assigned reference number A030-84.

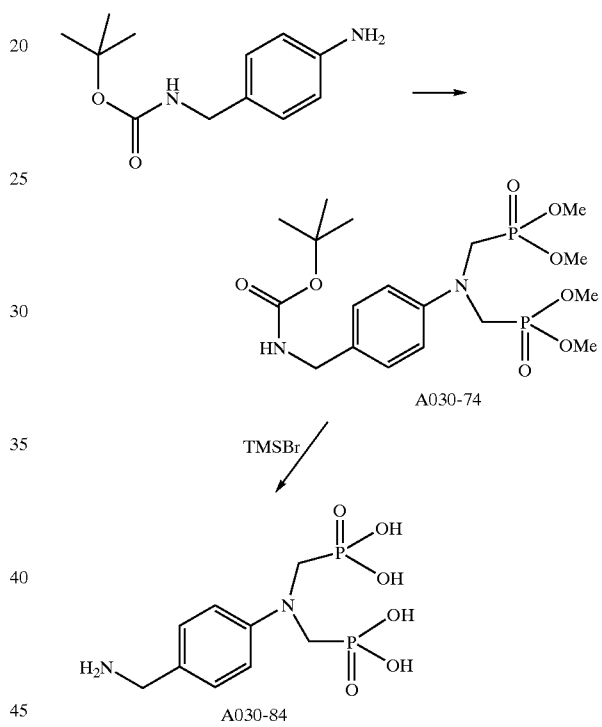

EXAMPLE 19

Synthesis of Compound A014-52

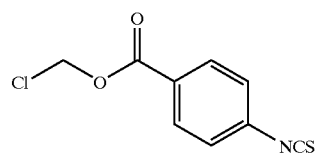

To 1.0 g of 4-carboxyphenyl isothiocyanate was added dichloromethane (15 mL) and distilled water (15 mL). The flask was cooled in an ice-water bath and sodium bicarbonate (4.0 equiv) and n-tetrabutylammonium hydrogen sulfate (0.05 equiv) were added. After 10 min, chloromethyl chlorosulfate (1.2 equiv) was added. The solution was stirred vigorously overnight and transferred to a separatory funnel with the aid of dichloromethane (10 mL). The layers were separated and the organic were washed with saturated sodium chloride (20 mL). The organics were dried over sodium sulfate and the solvent removed to provide 1.10 g of a tan solid. The presence of the title compound was indicated by a shift in retention time in of the product (4.2 min) versus starting carboxylic acid (3.2 min). The compound was also confirmed by proton NMR spectroscopy: $^1$H (CDCl$_3$) δ: 8.08 (d, 2H, J 8.8 Hz), 7.30 (d, 2H, J 8.8 Hz), 5.95 (s, 2H).

EXAMPLE 20

Synthesis of Compound A014-48

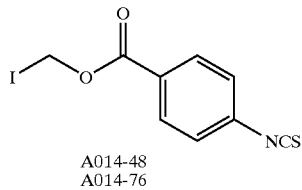

A014-48
A014-76

A solution of 250 mg of the chloromethyl ester (prepared via the procedure described in A014-52) in 2 mL acetone was treated with sodium iodide (1.2 equiv) and the solution was stirred overnight. The solution was filtered, the solvent removed, and the residue was taken up in dichloromethane (10 mL). The solution was washed with 10% (w/v) sodium sulfite (10 mL), 5% (w/v) sodium bicarbonate (10 mL), and water (10 mL). The organics were dried over sodium sulfate and the solvent was removed to provide 137 mg of a light green solid. The presence of the title compound was indicated by a shift in retention time in of the iodomethyl ester product (4.4 min) versus starting chloromethyl ester (4.2 min). The compound was also confirmed by proton NMR spectroscopy: $^1$H (CDCl$_3$) δ: 8.04 (d, 2H, J 8.8 Hz), 7.29 (d, 2H, J 8.1 Hz), 6.15 (s, 2H).

EXAMPLE 21

Synthesis of Compound A014-76

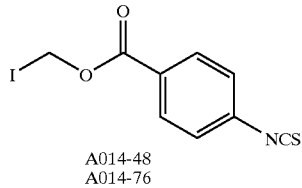

A014-48
A014-76

A solution of 387 mg of the chloromethyl ester (prepared via the procedure described in A014-52) in 6 mL 2-butanone was treated with sodium iodide (1.2 equiv) and the solution was heated 10 hr. The solution was filtered, the solvent removed, and the residue was taken up in dichloromethane (10 mL). The solution was washed with 10% (w/v) sodium sulfite (10 mL), 5% (w/v) sodium bicarbonate (10 mL), and water (5 mL). The organics were dried over sodium sulfate and the solvent was removed to provide 310 mg of a tan solid. The presence of the title compound was indicated by a shift in retention the iodomethyl ester product (4.4 min) versus starting chloromethyl ester (4.2 min).

EXAMPLE 22

Synthesis of Compound A018-24

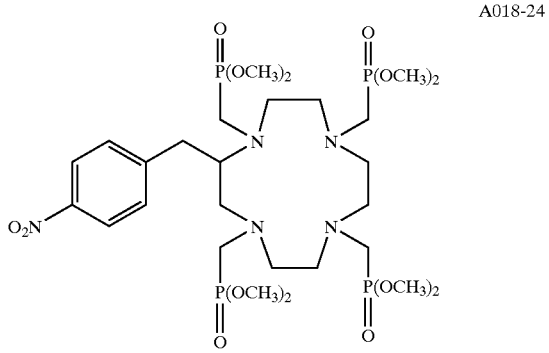

A018-24

A solution of 64 mg of 2-p-nitrobenzyl-1,4,7,10-tetraazacyclododecane (Macrocyclics) in 500 μL dioxane was treated with paraformaldehyde (50 mg) and trimethylphosphite (207 mg). The mixture was heated to 85° C. and then the solvent was removed via rotary evaporation at 75° C. Chloroform (10 mL) was added and the solution was washed with saturated sodium chloride (2×10 mL) and water (2×10 mL). The organics were dried over sodium sulfate and the solvent removed to provide a brown oil. This was purified via LC to provide the desired material. The presence of the title compound was confirmed by electrospray LC-MS A; $t_R$=1.8 min. MS [M=C$_{27}$H$_{53}$N$_5$O$_{14}$P$_4$] m/z 796 (MH$^+$), 818 (MNa$^+$).

EXAMPLE 23

Synthesis of Compound A022-32

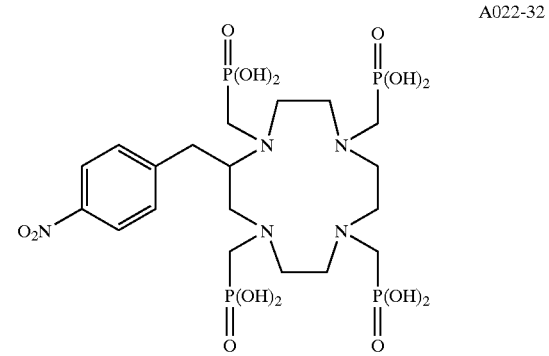

A022-32

A solution of the 33 mg of the phosphonated macrocycle (prepared in A018-24) in 700 μL dichloromethane was treated with bromotrimethylsilane (72 mg). The mixture was stirred overnight and then more bromotrimethylsilane (36 mg) was added and it was stirred an additional 3 days. Methanol (500 mL) was added and the solution stirred 1 hr, and then the volatiles were removed to give a brown oil. Addition of methanol precipitated a brown solid, which was filtered and dried. This was purified via LC to provide 2.7 mg of the desired material. The presence of the title compound was confirmed by electrospray LC-MS A; $t_R$=1.5 min. MS [M=C$_{19}$H$_{37}$N$_5$O$_{14}$P$_4$] m/z 682 (M−H$^-$), 340 [(M−2H)/2)$^{2-}$].

The nitro group is reduced using standard methods of reduction for example stirring with 5% palladium on carbon catalyst in methanol under an atmosphere of pure hydrogen. The mixture is then filtered (taking care to prevent air exposure to the catalyst) and the solvent evaporated give the amine.

EXAMPLE 24

Synthesis of Compound A022-56

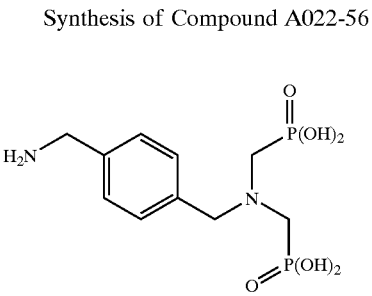

A022-56

A mixture of phosphorus acid (1.26 g), 6 M hydrochloric acid (19.5 mL), and p-xylenediamine (1.0 g) was heated to 100° C. To this was added 37% (wt/wt) aqueous formaldehyde (1.15 mL) and the mixture was stirred at 100° C. overnight. The mixture was filtered and the water removed by rotary evaporation at 80° C. to provide 2.11 g of a white solid. The presence of the title compound was confirmed by electrospray LC-MS using method B; $t_R$=1.8 min. MS [M=$C_{10}H_{18}N_2O_6P_2$] m/z 325 (MH$^+$).

EXAMPLE 25

Synthesis of Compound A018-12

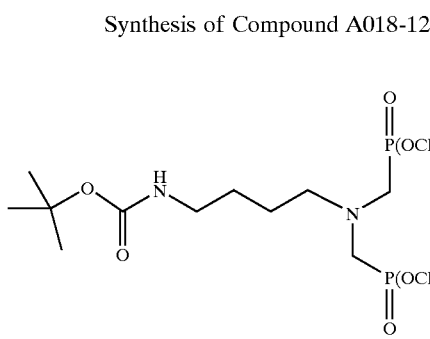

A018-12

A solution of 928 mg N-BOC-1,4-diaminobutane in 10 mL dioxane was treated with paraformaldehyde (592 mg) and trimethylphosphite (2.44 g). The mixture was stirred at 108° C. overnight and the solvent removed by rotary evaporation at 75° C. Chloroform (10 mL) was added and the solution was washed with saturated sodium chloride (2×10 mL) and water (2×10 mL). The organics were dried over sodium sulfate and the solvent removed to provide 1.55 g of an oil. The presence of the title compound was confirmed by electrospray LC-MS; $t_R$=2.4 min. MS [M=$C_{15}H_{34}N_2O_8P_2$] m/z 455(MNa$^+$).

EXAMPLE 26

Synthesis of Compound A026-92

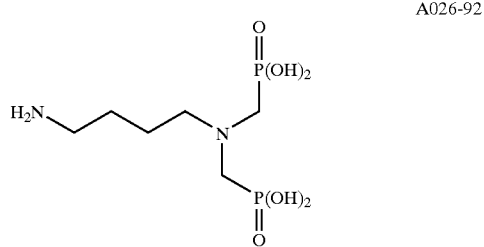

A026-92

A solution of 783 mg of the phosphonate (prepared in A018-12) in 18 mL dichloromethane was treated with bromotrimethylsilane (2.2 g). The solution was stirred overnight and methanol (10 mL) was added and the mixture stirred for 2 hr. The volatiles were removed to provide 1.22 g of a yellow oil. The presence of the title compound was confirmed by electrospray LC-MS using method B; $t_R$=0.4 min. MS [M=$C_6H_{18}N_2O_6P_2$] m/z 275(M−H$^-$).

EXAMPLE 27

Synthesis of Compound A030-74

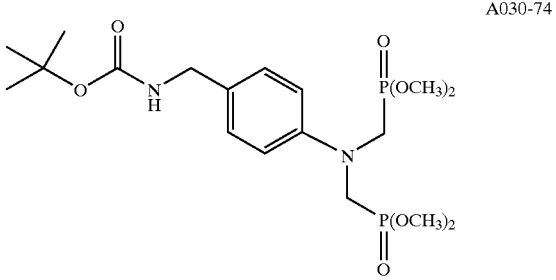

A030-74

A solution of 500 mg 4-[(N-BOC)aminoethyl]aniline in 10 mL dioxane was treated with paraformaldehyde (270 mg) and trimethylphosphite (1.12 g). The mixture was heated to 95° C. overnight. Then more paraformaldehyde (270 mg) and trimethylphosphite (1.12 g) were added and it was heated at 95° C. overnight again. The solution was cooled, taken up in chloroform (20 mL) and washed with saturated sodium chloride (20 mL) and water (20 mL). The organics were dried over sodium sulfate and the solvent and excess trimethylphosphite removed via rotary evaporation at 80° C. to provide 1.72 g of a clear oil. The presence of the title compound was confirmed by electrospray LC-MS; $t_R$=2.9 min. MS [M=$C_{18}H_{32}N_2O_8P_2$] m/z 467 (MH$^+$); 489 (MNa$^+$).

EXAMPLE 28

Synthesis of Compound A030-84

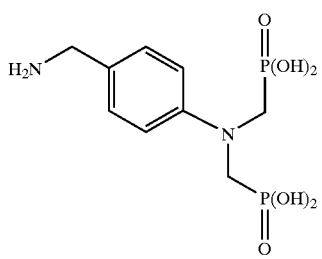

A030-84

A solution of 870 mg of the A030-74 in 10 mL dichloromethane was treated with bromotrimethylsilane (1.97 g). The solution was stirred overnight. Methanol (10 mL) was added and the solution was stirred 15 min and then concentrated to provide 1.12 g of an orange oil. The presence of the title compound was confirmed by electrospray LC-MS using method B; $t_R$=0.85 min. MS [M=$C_9H_{16}N_2O_6P_2$] m/z found for 309 [M–H]$^-$.

EXAMPLE 29

Synthesis of Compound A035-66

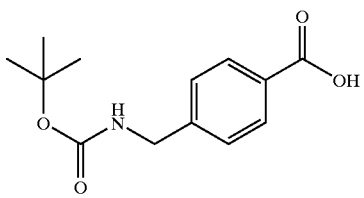

A035-66

A 2.0 g portion of 4-aminomethyl benzoic acid (Aldrich) was dissolved in 20 mL of water containing 0.64 g of solid NaOH. A 3.18 g portion of Boc anhydride (Aldrich) was added and the mix allowed stir overnight. The mix was adjusted to pH=2 by the careful addition of 15 mL of 2N HCl. The resulting white solid was filtered and dried to give 2.9997 g of product. The product was characterized by LCMS (retention time 2.901 minutes and desired M–H mass ion observed at 250 m/z).

EXAMPLE 30

Synthesis of Compound A035-6

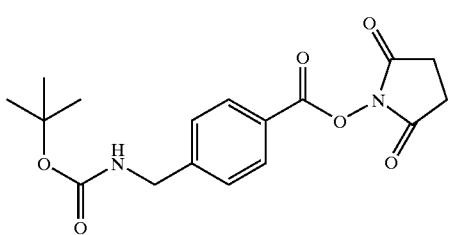

A035-6

A 1.5 portion of A35-66 was dissolved in 17 mL of dry THF along with 0.69 g of N-hydroxysuccinimide (Aldrich) and then treated all at once with 6 mL of 1M dicyclohexylcarbodiimide (Aldrich) in dichloromethane with stirring. After two days the white precipitate (dicyclohexylurea) was filtered off and the filtrate rotoevaporated under vacuum to yield 2.8146 g of white solid characterized by LCMS (retention time 3.299 minutes and desired M+H observed at 349 m/z).

EXAMPLE 31

Synthesis of Compound A035-14

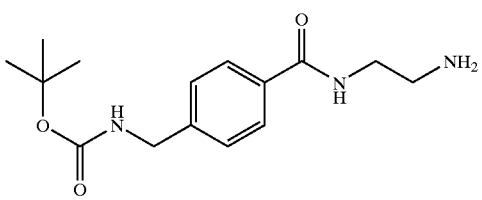

A035-14

A 500 mg portion of A035-6 was dissolved in 5 mL of dry THF and treated with 1.002 mL (10 equivalents) of ethylenediamine (EDA) and allowed to stir for 2 hours. The solution was then decanted from the formed solid. The solvent and excess EDA was then removed from the decanted solution by rotoevaporation under vacuum to give 0.8728 g of white solid; the product was characterized by LCMS (retention time 1.608 minutes and desired M+H observed at 294 m/z).

EXAMPLE 32

Synthesis of Compound A032-24

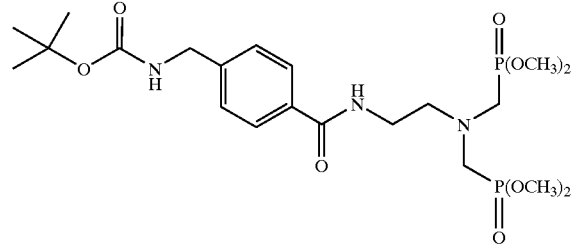

A032-24

A solution of 872 mg of the amine (prepared in A035-14) in 10 mL dioxane was treated with paraformaldehyde (535 mg) and trimethylphosphite (2.21 g). The mixture was heated at 100° C. overnight and then the solvent removed by rotary evaporation at 80° C. to give a brown solid. Chloroform (25 mL) was added and the solution was washed with water (15 mL). The organics were dried over sodium sulfate and the solvent removed to provide 241 mg of a yellow semi-solid. This was purified via LC to provide 58.8 mg of desired material. The presence of the title compound was confirmed by electrospray LC-MS; $t_R$=2.6 min. MS [M=$C_{21}H_{37}N_3O_9P_2$] m/z 538 (MH$^+$), 560 (MNa$^+$).

EXAMPLE 33

Synthesis of Compound A032-40

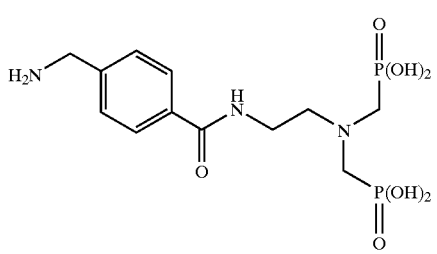

A solution of 54.6 mg of phosphonate (prepared in A032-24) in 1 mL dichloromethane was treated with bromotrimethylsilane (156 mg). The mixture was stirred overnight. Ethanol (0.5 mL) and water (3 drops) were added and it was stirred 1 hr and then the volatiles were removed and the material dried under vacuum. This was taken up in water (1 mL) and lyophilized to provide 59 mg of a tan solid. The presence of the title compound was confirmed by electrospray LC-MS using method B; $t_R$=0.4 min. MS [M=$C_{12}H_{21}N_3O_7P_2$] m/z 380 (M–H$^-$), 382 (MH$^+$), 404 (MNa$^+$).

EXAMPLE 34

Synthesis of Compound A026-60

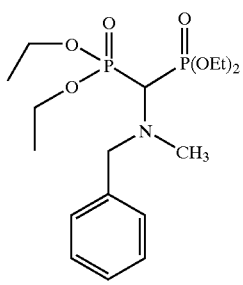

A026-60 prepared via the procedure of Kantoci, D., Kenike, J. K., Wechter, W. J. *Syn. Commun.*, 1996, 26(10), 2037.: A mixture of N-benzyl-N-methylamine (20.0 g), diethylphosphite (70.7 g) and triethylorthoformate (29.3 g) was stirred under argon at reflux (150° C.) for 5 hr. Ethanol was removed via rotary evaporation at 70° C., and the mixture was again heated at reflux overnight. The solution was diluted with 600 mL chloroform and washed with 1 M sodium hydroxide (3×100 mL) and saturated sodium chloride (3×150 mL). The organics were dried over sodium sulfate and the solvent removed to provide 74.0 g of a light yellow oil. 10.0 g of this material was subjected to silica gel column chromatography using 14:4:1 ethyl acetate:hexane:methanol as eluent. This provided 6.08 g of a clear oil. The presence of the title compound was confirmed by electrospray LC-MS; $t_R$=3.4 min. MS [M=$C_{17}H_{31}NO_6P_2$] m/z 408(MH$^+$), 430 (MNa$^+$), 471 (MNa–CH$_3$CN$^+$).

EXAMPLE 35

Synthesis of Compound A030-54

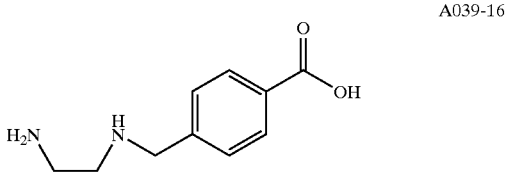

A030-54 (compound is known, CAS # 80475-00-9), prepared via the procedure of Kantoci, D., Kenike, J. K., Wechter, W. J. *Syn. Commun.*, 1996, 26(10), 2037.: A solution of 4.52 g of the phosphonated benzylamine (prepared via A026-60) in methanol (45 mL) was treated with 10% palladium on carbon (200 mg) and subjected to an atmosphere of hydrogen overnight. The palladium/carbon was filtered to provide 2.98 g of a light yellow oil. The presence of the title compound was confirmed by electrospray LC-MS using method A; $t_R$=1.9 min. MS [M=$C_{10}H_{25}NO_6P_2$] m/z 318(MH$^+$).

EXAMPLE 36

Synthesis of Compound A039-16

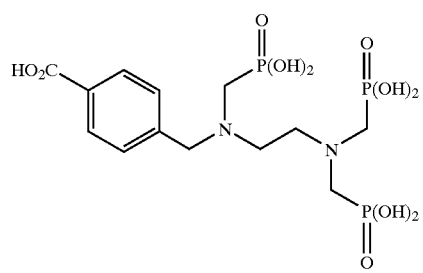

A039-16: A 500 mg sample of 4-chloromethylbenzoic acid (Aldrich) was dissolved in 8 mL of THF and treated all at once with 5 equivalents of ethylenediamine (Aldrich) (983 uL). After 24 hours the solvent was stripped under high vacuum and the white solid (93%) was characterized by LCMS (retention time 0.4 minutes and desired M+H observed at 195 m/z).

EXAMPLE 37

Synthesis of Compound A038-24

A mixture of 679 mg of the amino acid (prepared via A039-16), 37% (wt/wt) aqueous formaldehyde (1.04 mL), phosphorus acid (1.15 g), and concentrated (12.1 M) hydrochloric acid (2.3 mL) in dioxane (10 mL) was stirred at 100° C. overnight. The solvent was removed via rotary evaporation at 75° C. and the mixture was centrifuged and the solid discarded. To the liquid was added more formaldehyde solution (1.04 mL), phosphorus acid (1.15 g), concentrated hydrochloric acid (2 mL) and dioxane (10 mL) and it was again was stirred overnight at 100° C. The solvent was removed via rotary evaporation at 75° C. to provide a thick oil. This was purified via LC to provide 276 mg of a brown solid. The presence of the title compound was confirmed by electrospray LC-MS using method A; $t_R$=0.6 min. MS [M=$C_{13}H_{23}N_2O_{11}P_3$] m/z 475 (M−H$^-$), 477 (MH$^+$).

EXAMPLE 38

Synthesis of Compound A038-50

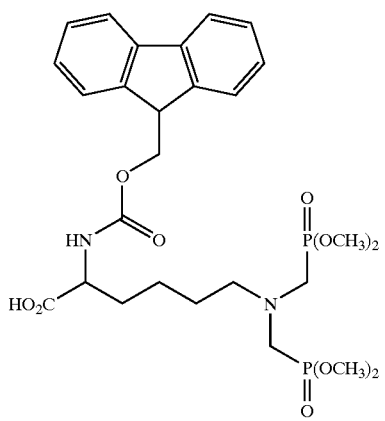

A038-50

A mixture of 6.0 g Fmoc-Lys-OH (Advanced ChemTech) in methanol (25 mL) and water (25 mL) was treated with 37% (wt/wt) aqueous formaldehyde (6.06 mL) and dimethylphosphite (8.96 g). The mixture was stirred at 80° C. for 2 hr, cooled, and extracted with dichloromethane (1×100 mL, 2×50 mL). The organics were washed with saturated sodium chloride (50 mL), dried over magnesium sulfate for 30 min, and the solvent removed to provide 10.17 g of a light green oil. The presence of the title compound was confirmed by electrospray LC-MS using method A; $t_R$=3.3 min. MS [M=$C_{27}H_{38}N_2O_{10}P_2$] m/z 613 (MH$^+$), 636 (MNa$^+$).

EXAMPLE 39

Synthesis of Compound A038-66

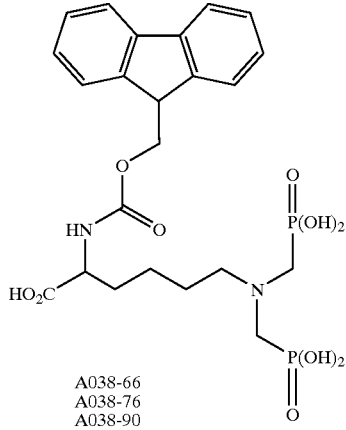

A038-66
A038-76
A038-90

A solution of 23.9 mg phosphonated Fmoc-Lys-OH (prepared via A038-50) in dichloromethane (1 mL) was treated with bromotrimethylsilane (60 mg). The mixture was stirred overnight. The presence of the title compound was confirmed by electrospray LC-MS using method A; $t_R$=3.4 min. MS [M=$C_{23}H_{30}N_2O_{10}P_2$] m/z 555 (M−H).

EXAMPLE 40

Synthesis of Compound A038-76

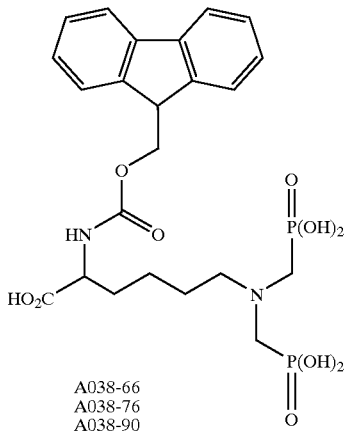

A038-66
A038-76
A038-90

A solution of 112.9 mg phosphonated Fmoc-Lys-OH (prepared via A038-50) in 6 M hydrochloric acid (3 mL) was stirred at 80° C. for 2 days. Water (9 mL) was added and after 2 more days the mixture was centrifuged and the liquid decanted. The solid was dried under vacuum to provide 86.8 mg of an off-white solid. The presence of the title compound was confirmed by electrospray LC-MS using method A; $t_R$=3.1 min. MS [M=$C_{23}H_{30}N_2O_{10}P_2$] m/z 555 (M−H$^-$).

EXAMPLE 41

Synthesis of Compound A038-90

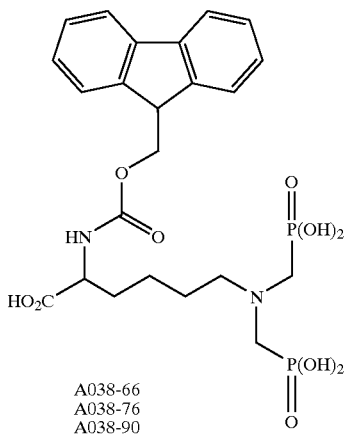

A038-66
A038-76
A038-90

A solution of 500 mg Fmoc-Lys-OH (Advanced ChemTech) in dioxane (5 mL) was treated with 37% (wt/wt) aqueous formaldehyde (303 μL), phosphorus acid (333 mg), and concentrated (12.1 M) hydrochloric acid (674 μL). The mixture was stirred at 90° C. overnight, the solvent was removed via rotary evaporation at 75° C. The presence of the title compound was confirmed by electrospray LC-MS using method B; $t_R$=5.4 min. MS [M=$C_{23}H_{30}N_2O_{10}P_2$] m/z 555 (M−H$^-$).

EXAMPLE 42

Synthesis of Compound A042-18

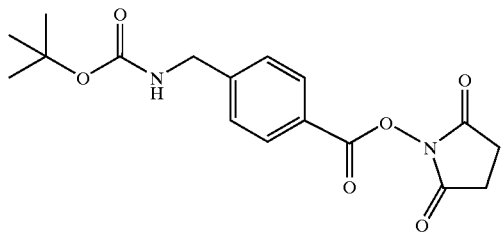

A042-18

A solution of 1.29 g of the Boc-protected amino acid (prepared above as lot A035-66) in 15 mL tetrahydrofuran was treated with N-hydroxysuccinimde (623 mg) and 1.0 M 1,3-dicyclohexylcarbodiimide in dichloromethane (5.4 mL). The mixture was stirred overnight and a white precipitate was filtered and the supernatant concentrated to provide 1.89 g of a white solidThe presence of the title compound was indicated by presence of a UV signal at 3.3 min.

EXAMPLE 43

Synthesis of Compound A042-26

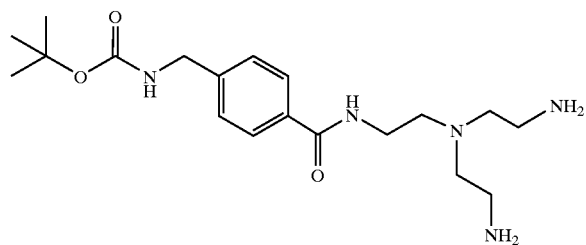

A042-26

To a solution of 2.1 g tris-(2-aminoethyl)amine in 20 mL tetrahydrofuran was added drop wise a solution of 1.0 g of the activated ester (prepared via A042-18) in 20 mL tetrahydrofuran over a period of 40 minutes. The mixture was stirred overnight resulting in a precipitate that was filtered and concentrated via rotary evaporation to provide 2.10 g of a yellow oil. The presence of the title compound was confirmed by electrospray LC-MS using method A; $t_R$=1.4 min. MS [M=$C_{19}H_{33}N_5O_3$] m/z 380 (MH$^+$), 402 (MNa$^+$).

EXAMPLE 44

Synthesis of Compound A042-32

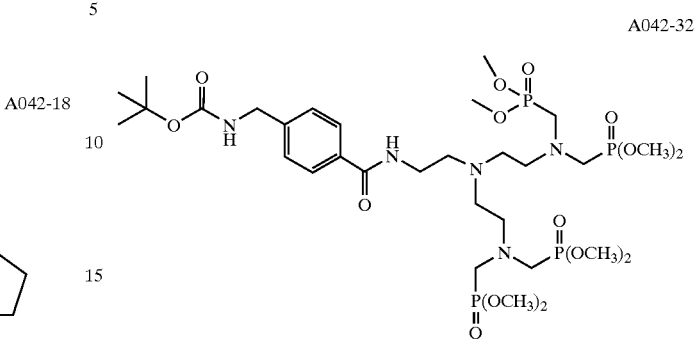

A042-32

A solution of 2.08 g amine (prepared via A042-26) in dioxane (20 mL) was treated with paraformaldehyde (1.50 g) and dimethylphosphite (6.85 g). The mixture was stirred at 90° C. overnight and the solvent removed via rotary evaporation at 70° C. Dichloromethane (50 mL) was added and it was washed with saturated sodium chloride (25 mL) and water (25 mL). The organics were dried over sodium sulfate and the solvent removed. The residue was purified via LC to provide 123.8 mg of a yellow oil. The presence of the title compound was confirmed by electrospray LC-MS using method D; $t_R$=2.2 min. MS [M=$C_{31}H_{61}N_5O_{15}P_4$] m/z 868 (MH$^+$).

EXAMPLE 45

Synthesis of Compound A042-70

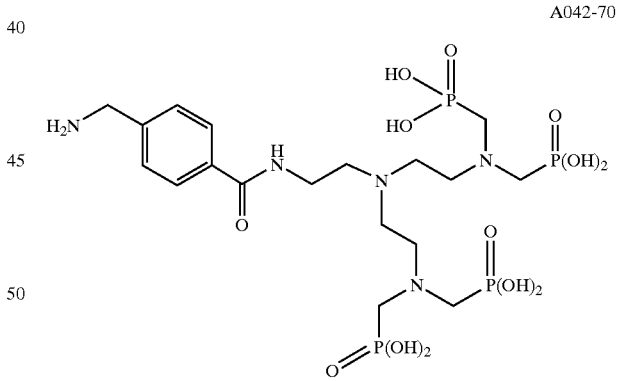

A042-70

A solution of 111.1 mg of the phosphonated diamine (prepared via A042-32) in 1 mL dichloromethane was treated with 194 mg of bromotrimethylsilane. After 5 hr, methanol (1 mL) was added, the mixture was stirred for 1 hr, and the solvent was removed to provide 113.9 mg of a tan solid. The presence of the title compound was confirmed by electrospray LC-MS using method B; $t_R$=1.0 min. MS [M=$C_{18}H_{37}N_5O_3P_4$] m/z 328 [(M+2H/2)$^{2+}$)], 656 (MH$^+$). The compound was also analyzed by proton NMR spectroscopy: $^1$H (CDCl$_3$) δ: 7.77 (d, 2H, J 8.1 Hz), 7.43 (d, 2H, J 8.2 Hz), 4.1–3.3 (m, 33H).

EXAMPLE 46

Synthesis of Compound A026-94

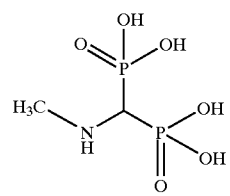

A solution of 750 mg of the phosphonate (prepared via A030-54) in 24 mL dichloromethane was treated with bromotrimethylsilane (2.89 g). The solution was stirred overnight. Methanol (10 mL) was added and the solution stirred for 2 hr and the solvent removed to provide a yellow oil which was lyophilized, resulting in 364 mg of a white solid. The presence of the title compound was confirmed by electrospray LC-MS using method B; $t_R$=0.6 min. MS [M=$C_2H_9NO_6P_2$] m/z 204 (M−H⁻).

EXAMPLE 47

Synthesis of Compound A042-96

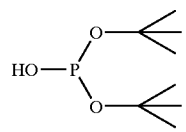

A042-96 (tert-butylphosphite): A solution of 4.10 g phosphorus acid in 100 mL tetrahydrofuran was treated with 2-methyl-2-propanol (7.41 g). A 1.0 M solution of 1,3-dicyclohexylcarbodiimide in dichloromethane (100.0 mL) was added, resulting in formation of a white solid. The mixture was stirred overnight and the solid filtered and the solvent removed to provide 6.82 g of a yellow oil. The presence of the title compound was confirmed by GC-MS. The following fragments were found: 57 [(CH$_3$)$_3$C⁺], 83 [HP(OH)$_3$⁺], 123 [(HO)$_2$PC(CH$_3$)$_2$⁺].

EXAMPLE 48

Synthesis of Compound A042-98

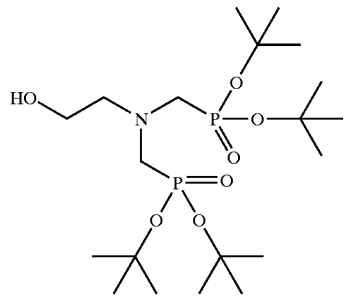

A mixture of ethanolamine (858 mg), paraformaldehyde (1.05 g), tert-butylphosphite (prepared via A042-96, 6.82 g) in benzene (100 mL) was heated at 90° C. overnight, resulting in a liquid atop a thick oil. The liquid was decanted and concentrated via rotary evaporation, resulting in an oil that was subjected to silica gel column chromatography using 10% methanol in dichloromethane as eluant. A clear oil (436 mg) was obtained. The presence of the title compound was confirmed by electrospray LC-MS using method A; $t_R$=3.6 min. MS [M=$C_{20}H_{45}NO_7P_2$] m/z 496 (MNa⁺).

EXAMPLE 49

Synthesis of Compound A029-34

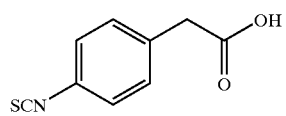

A029-34

In order to prepare 4-isothiocyanatophenyl acetic acid, 1.3 ml (13.5 mmoles, 2 equivalents) thiophosgene was added to 1.0 g of 4-aminophenyl acetic acid (6.61 mmoles) [Aldrich] and 3.73 g of anhydrous potassium carbonate (4 equivalents) suspended in 20 ml. dry THF. The suspension was stirred for 15 minutes at room temperature followed by a 4 hours heating in an silicon oil bath at 85° C. The solution was cooled and passed though a one inch celite bed in a filter syringe. The solution was collected in a round bottom flask and the solvent removed under reduced pressure.

The sample was stored in a vacuum dessicator for two hours then dissolved in acetone-water mixture, frozen and lypholized to give 1.65 g of a blackish solid. The compound was identified by a shift in retention time in the LCMS chromatogram to 3.32 minutes.

EXAMPLE 50

Synthesis of Compound A040-22

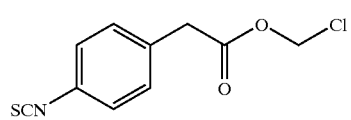

A040-22

In order to prepare 4-Isothiocyanatophenyl acetic acid chloromethyl ester, 0.530 g of 4-Isocyanatophenyl acetic acid (2.7 mmoles) was dissolved in 5.0 ml methylene chloride in a glass vial, to which was added 0.044 g of tetra-n-butyl ammonium hydrogen sulfate (phase transfer catalyst—0.05 equivalents) and 0.866 g sodium bicarbonate (4 equivalents) dissolved in 5.0 ml of water. The solution was stirred in an ice bath for ten minutes. To the cold mixture was added 0.520 g of chloromethyl chloro sulfate (ACROS Chemical—1.2 equivalents) and stirred for 4 hours with the temperature gradually coming to room temperature. The organic layer was separated in a separatory funnel, washed with 10 ml saturated brine and dried over anhydrous sodium sulfate. The solvent was removed under vacuum to give 0.703 g of a crude oil. The product was identified by the formation of new peak in the LCMS with a retention time of 4.268 minutes and the disappearance of the peak corresponding to starting material.

EXAMPLE 51

Synthesis of Compound A040-26

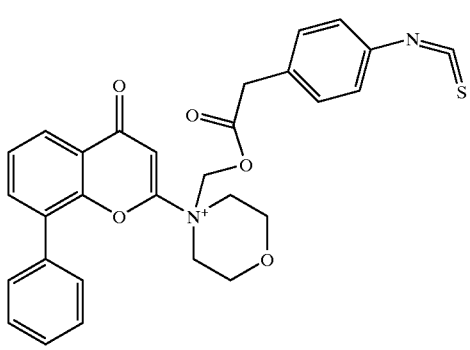

A040-26

In order to prepare the 4-isothiocyanato phenyl acetic acid quartemary salt derivative of Compound 1101, Compound 1101 (0.300 g, 1.0 mmole) and 0.582 g godium iodide (4 equivalents) were dissolved in 4.0 ml dry acetonitrile in a one dram vial. The 4-isothiocyanatophenyl acetic acid chloromethyl ester (compound A040-22) in 2.0 ml dry acetonitrile was added with stirring. The mixture was heated on a silicone oil bath at 65° C. for five hours, monitoring the progress of the reaction by LCMS. When most of the Compound 1101 starting material was consumed the reaction mixture was purified using preparative LCMS retention time of 3.019 minutes, m$^+$=513. A yield of 194.1 mg of 94% pure product was obtained and identified by LCMS. Compound A040-26 is then reacted with nucleophile-bearing targeting agents as described by the methods disclosed in the examples utilizing compound 1105 to prepare useful targeted prodrugs.

EXAMPLE 52

Synthesis of Compound A044-52

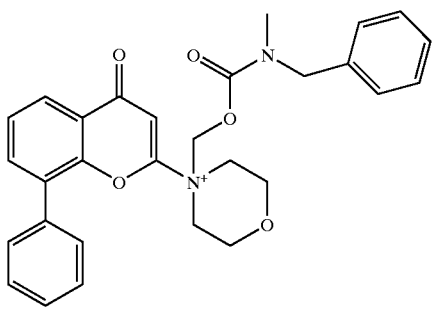

A044-52

In order to prepare N-benzyl-N-methyl carbamoyl chloromethyl ester, 0.300 mg (324 uL, d=0.942) benzylmethylamine and 640 uL diisopropyl ethyl amine (1.5 equivalents) were dissolved in 2.0 ml dry methylene chloride and cooled in an ice bath. When the solution was cooled, 330 uL chloromethyl chloroformate (1.5 equivalents) in 2.0 ml dry methylene chloride was added and stirred for 2 hours, gradually allowing the solution to come to room temperature. The yellow solution was placed in a separatory funnel and washed with 2×10 ml 1N HCl, 1×10 ml water and 2×10 ml 1 N sodium bicarbonate. The organic layer was dried over sodium sulfate and concentrated under reduced pressure. The chloromethyl carbamate was obtained as 0.95 g of a yellow oil and identified in the LCMS as a uv active component with a retention time Of 3.520 minutes In order to prepare the N-benzyl, N-methyl carbamoylmethyl quarternary salt of Compound 1101, 0.5 g of Compound 1101 and 0.5 g sodium iodide (20 equivalents) were dissolved in 5.0 ml dry acetonitrile in a glasss vial. The N-benzyl, N-methyl carbamoyl chloromethyl ester was added to the solution then placed on an oil bath at 65° C. overnight. The product was identified by LCMS and purified by preparative LCMS to give 169.5 mg (21.5% theoretical yield) of a solid assigned A044-52 with a retention time of 2.731 minutes,, M+=485 and 90% purity.

EXAMPLE 53

Synthesis of Compound A044-62

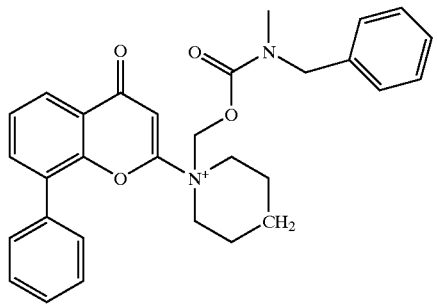

A044-62

In order to prepare N-benzyl,N-methyl carbamoyl methyl quarternary salt of Compound 1157, 22 mg Compound 1157, 20 mg sodium iodide (2.0 equivalents) and 30.7 mg N-benzyl-N-methyl carbonmoyl chloromethyl ester (2.0 equivalents) were mixed in 500 uL dry acetonitrile in a glass vial, and heated in an oil bath at 65° C. overnight. The product was identified via LCMS and purified by preparative LCMS. 5.4 mg was obtained (15.5% theoretical yield) of a compound with a retention time of 2.810 minutes, M+=483 and 98% purity.

EXAMPLE 54

Synthesis of Compound A044-28

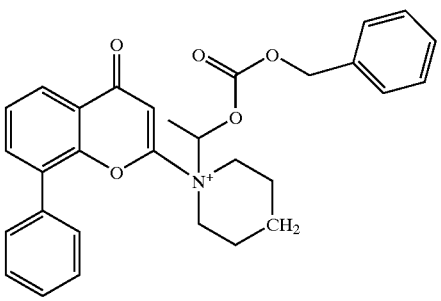

A044-28

In order to prepare the benzyl formoyl-1-ethyl quarternary salt of Compound 1101, 200 uL 1-chloroethyl chloroformate was added to 100 uL benzyl alcohol in 2.0 ml dry methylene chloride in a glass vial incubated at 0° C. in an ice bath. To the cooled solution was added 200 uL pyridine which caused formation of a white precipitate within a few minutes. Stirring was continued at room temperature overnight. Ten ml of methylene chloride was added to the mixture that was then washed with 1×10 ml 0.5 M HCl, 1×10 ml water and 1×10 ml 0.5 N sodium bicarbonate solution. The organic layer was dried over sodium sulfate and the solvent removed under reduced pressure. The benzyl-1-chloroethyl formate was identified as a uv active component with a retention time of 3.933 minutes.

To 100 mg Compound 1101 and 100 mg NaI (20 equivalents) dissolved in 1.0 ml dry acetonitrile was added 107 mg (1.5 equivalents) of the benzyl-1-chloroethyl formate. The mixture was heated at 65° C. overnight. The LCMS indicated the presence of starting material so an additional 107 mg (1.5 equivalents) of benzyl-1-chloroether formate was added and the heating continued another 24 hours. The LCMS identified a product which could be separated from starting material with slow gradient chromatography. The desired compound was isolated using preparative LCMS to give 13.7 mg (8.7% theoretical yield) of a compound with a retention time of 4.690 minutes, M=+488 in 98.6% purity.

EXAMPLE 55

Synthesis of Compound 1126

In order to prepare chloromethyl-t-butylsuccinate, mono t-butyl succinate (Aldrich), 2.0 g, that was dissolved in 8.0 ml methylene chloride was added to a glass vial containing 4.0 g potassium carbonate and 0.24 g tetra n-butyl ammonium hydrogen sulfate in 8.0 ml water with stirring in an ice bath. After 15 minutes, 1.3 mL chloromethyl chlorosulfate (Acros) was added to the methylene chloride layer and the reaction mixture was stirred with the temperature slowly coming to room temperature. The organic layer was separated and washed with 1×10 ml water and 1×10 ml saturated brine solution. The solution was dried over anhydrous sodium sulfate and the solvent removed under reduced pressure. 3 g of a pale yellow oil was obtained and assigned lot number A047-71.

The 3 g of A047-71 from above were dissolved in 36 mL of acetonitrile and treated with 1.8 g of Compound 1101 and 1.8 g of NaI and put on a heater with stirring for 16 hours. The reaction mix (including precipitate) was partitioned between water and methylene chloride and the methylene chloride layer was separated, washed with brine, dried over sodium sulfate and evaporated to give a dark oil. This oil was dissolved in 5 mL of acetonitrile and stored in the freezer for two days. The yellow precipitate that formed was then filtered and washed with 3 mL of acetonitrile and dried to give 2.8435 g of >95% purity product assigned lot A046-67A, retention time 2.719 minutes, [M+] of 494 m/z. All of this product was dissolved in 10 mL of thionyl chloride and heated to 65° C. for 4 hours. The excess thionyl chloride was removed under vacuum and the yellow oil dried under high vacuum to yield 1.9906 g of the acid chloride (Compound 1111) as a yellow crunchy solid. This solid was used directly in subsequent reactions.

Figure 8:
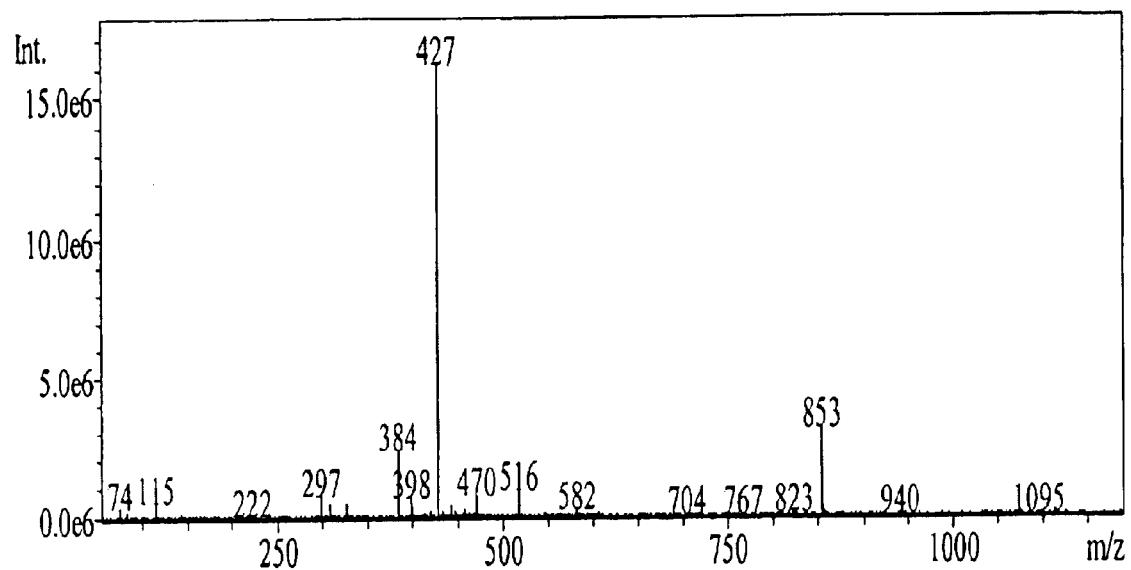
FIG. 8 shows the Positive Mass Spectrum of Compound 1126 (A036-33).
Figure 9:
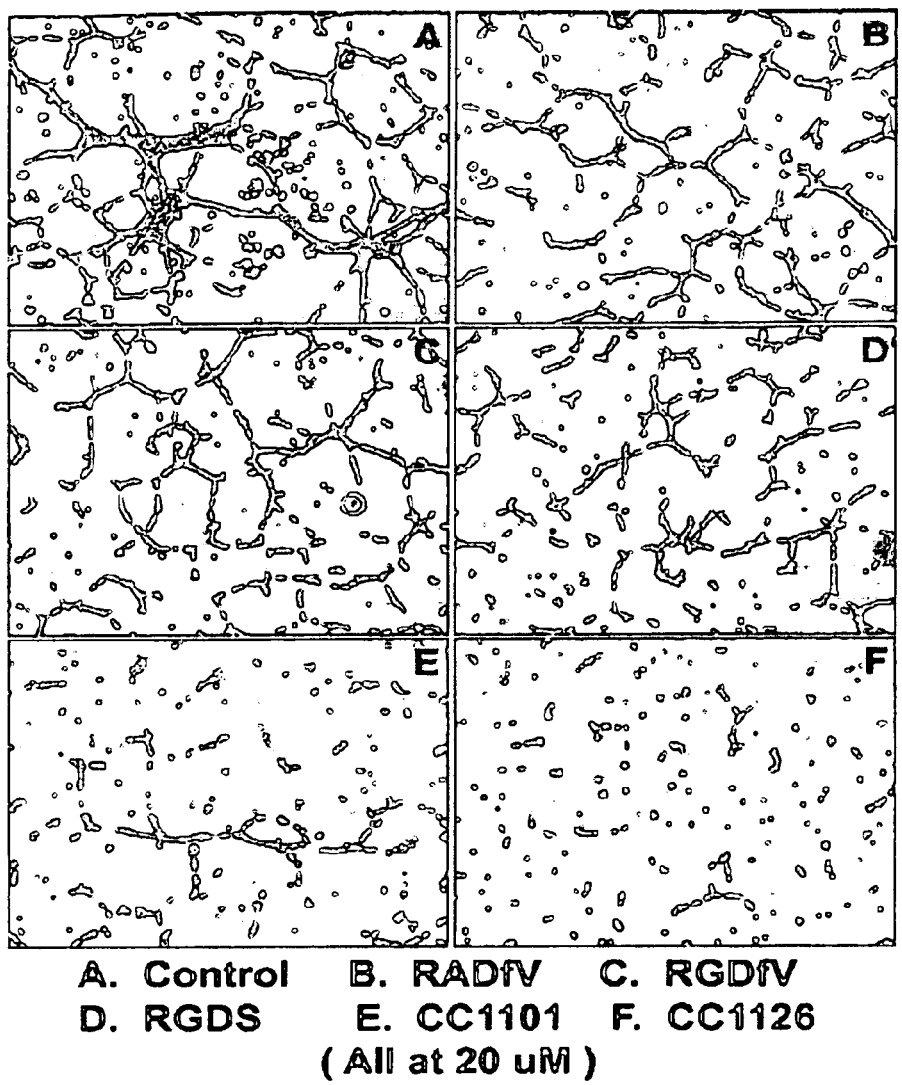
FIG. 9 shows that Avβ3 targeted PI 3 kinase inhibitors abrogated the tube formation of EDC-CBF1 endothelial cells on Matrigel.

In order to couple the Compound 1101 acid chloride and de-FMOCed RGDS peptide, 1.26 g acid chloride of Compound 1111 and 5.6 g de-FMOC removed RGDS peptide (both dried in vacuum dessicator over Phosphorous pentoxide) were mixed in a 50 ml round bottom flask under Argon gas. To the solids was added 270 uL dry pyridine in 28 ml methylene chloride and the mixture shaken to dissolve the acid chloride. The mixture was placed on an orbital shaker for one hour. The solution was drained through a fritted plastic syringe and washed with 2×10 ml methylene chloride and the solvent drained. To the resin was added 500 uL anisole followed by 20 ml of a 50/50 TFA/methylene chloride solution. The resin was allowed to stand in the TFA solution for three hours with occasional shaking. The TFA solution was drained away from the resin. The resin was washed with 10 ml methylene chloride which was combined with the TFA solution. The TFA solution was placed into four vials that were blown dry with Argon gas. Each vial was treated with multiple ether washes and again blown dry with Argon gas. The product was identified by LCMS and was purified in seventeen runs using preparative reverse phase LCMS. The combined runs yielded 163.7 mg of 96% pure product (assigned lot A036-33) with a retention time of 1.768 minutes, M+=853 and [M+H]/2 at 427 m/z. The LC-MS chromatogram and mass spectum for this compound are shown in FIG. 7 and FIG. 8. In FIG. 7 the x-axis is time in minutes and the y-axis for the top chromatogram is milli-absorbance units for the UV detector at 254 nm and for the bottom chromatogram is millivolts detected by the evaporative light scattering detector. In FIG. 8 the x-axis is the mass-to-charge ratio (m/z) and the y-axis is the intensity of the mass ion count.

SCHEME 10

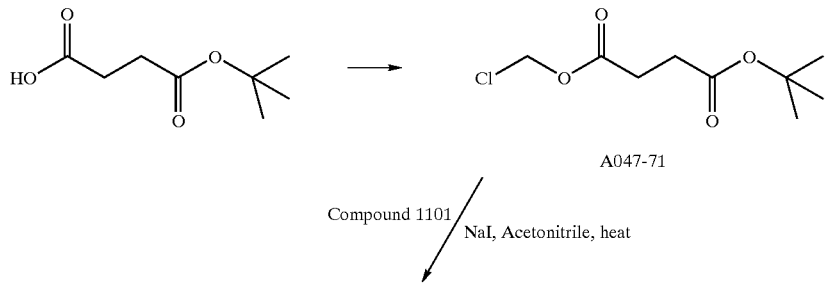

-continued

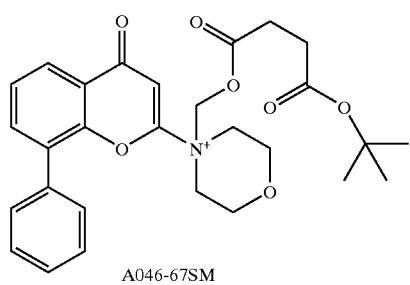

A046-67SM

TFA →

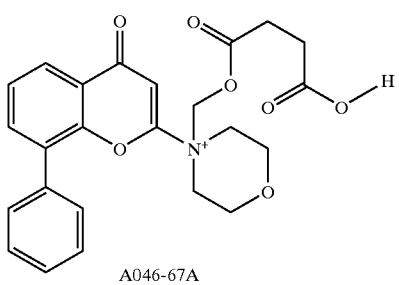

A046-67A

Thionyl Chloride, Heat

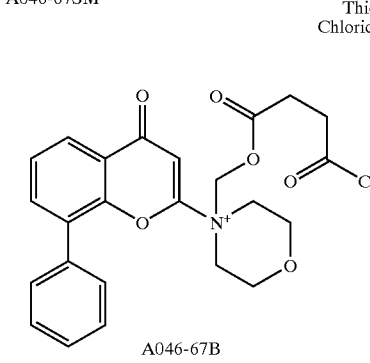

A046-67B

RGDS-Polymer → TFA (resin cleavage) → Prep HPLC

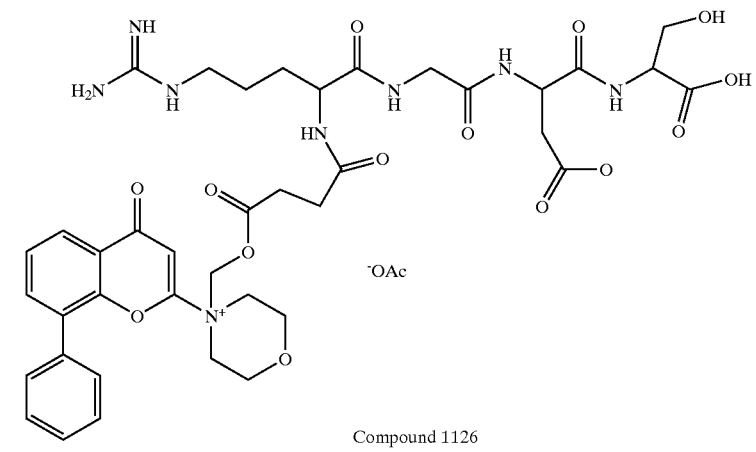

Compound 1126

EXAMPLE 56

Synthesis of Compound A052-10

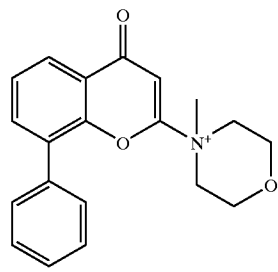

A052-10

In order to preparation the phthalimidomethyl quartemary salt of Compound 1101, a mixture of 100 mg Compound 1101 and 100 mg sodium iodide (2.0 equivalents) were dissolved in 3.0 ml dry acetonitrile. To the mixture was added 128 mg of chloromethylphthalimide (Aldrich) and the vial was heated in an oil bath at 55° C. for four days. The product was identified by LCMS as a new peak with a retention time of 3.984 minutes, M+=467.

EXAMPLE 57

Synthesis of Compound A052-08

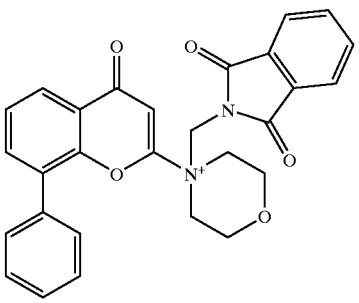

A052-08

In order to preparation the phthalimidomethyl quartemary salt of Compound 1101, a mixture of 100 mg Compound 1101 and 100 mg sodium iodide (2.0 equivalents) were dissolved in 3.0 ml dry acetonitrile. To the mixture was added 128 mg of chloromethylphthalimide and the vial was heated in an oil bath at 55° C. for four days. The product was identified by LCMS as a new peak with Rf=3.984, M+=467.

EXAMPLE 58

Synthesis of Compound A044-78

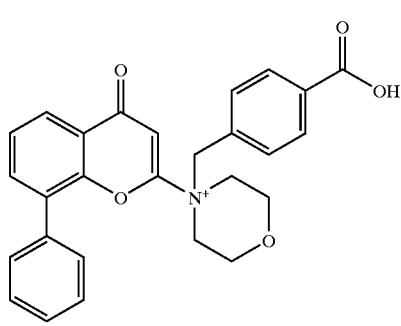

A044-78

In order to prepare the 4-Carboxybenzyl quartemary salt of Compound 1101, 300 mg Compound 1101, 400 mg sodium iodide and 500 mg of chloromethyl benzoic acid were mixed in a glass vial and suspended in 4.0 ml dry acetonitrile. The reaction was heated on an oil bath at 65° C. and monitored for two weeks by LCMS. The solution was filtered through a fritted plastic syringe that had been fitted with an additional 2 micron filter. The desired compound was isolated using preparative LCMC and had a retention time of 3.717 minutes, M+=442. A yield of 27.7 mg of 96% purity was obtained. The carboxlic acid group of compound A044-78 is converted to a reactive group by a) reaction with N-hydroxysuccinimide as described by the method in Example 31 to prepare the NHS active ester or b) conversion to the acid chloride as described by the method in Example 56. Either of these reactive groups are then reacted with the nucleophilic amine or alcohol groups of targeting agents using methods described in the previous Examples to give targeted prodrug conjugates.

EXAMPLE 59

Synthesis of Compound A044-80

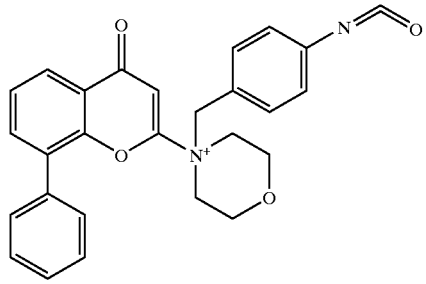

A044-80

In order to prepare the 4-Isocyanatobenzyl quartemary salt of Compound 1101, a mixture of 300 mg Compound 1101, 450 mg sodiun iodide (3.0 equivalents) and 490 mg (3.0 equivalents) of 4-chloromethyl benzeneisocyanate was dissolved in 4.0 ml dry acetonitrile and heated oil in an oil bath at 65° C. for 2 days. The LCMS indicated the reaction had gone to completion because of the absence of starting material (Compound 1101). The product was identified as a new peak with a retention time of 4.577 minutes, M+=439. Compound A044-80 is reacted with nucleophilic groups of various targeting agents to produce carbamate or urea linkages to the targeting agents by the methods of Examples utilizing compound 1105 and A040-26.

EXAMPLE 60

Synthesis of Compound A044-4

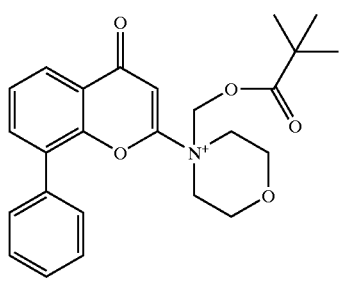

A044-4

In order to prepare the pivaloylmethyl quartemary salt of Compound 1101, 100 mg pivaloyl chloride (2.0 equivalents) was added dropwise to a mixture of 100 mg Compound 1101 and 100 mg sodium iodide (2.0 equivalents) in 2.0 ml dry acetonitrile. The mixture was heated on an oil bath at 65° C. for 2 hours. The solids were filtered using a fritted plastic syringe fitted with a 2 micron filter. The compound was identified and isolated using preparative LCMS. A yellow solid with a retention time of 2.735 minutes, M+=422 was obtained with a yield of 102.3 mg of 93.7% purity.

EXAMPLE 61

Synthesis of Compound A040-70

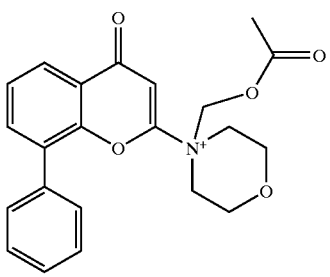

A040-70

In order to prepare the acetoxymethyl quarternary salt of Compound 1101, 1.0 g Compound 1101 was dissolved in 10 ml dry acetonitrile in a glass vial, and 1.0 g bromomethyl acetate (2.0 equivalents) was added and allowed to stir at room temperature overnight. LCMS indicated presence of starting material, so the reaction was heated at 65° C. in an oil bath for 8 hours. The mother liquors were decanted from the solid and the solids washed with a small amount of cold acetonitrile. The solid was dried in a vacuum dessicator overnight. The product was identified as 264 mg of a white solid with a retention time of 2.204 minutes, M+=380 which was 97% pure. This compound was found to have very high water solubility; a 32.5 millimolar solution of this compound in phosphate buffered saline was prepared by dissolving 27 mg in 1.865 mL of phosphate buffered saline with a resulting pH of around 4. A 50 uL aliquot of this solution (which contains 1.625 uMoles of Compound 1101 as a prodrug) was injected in the tail vein of a nude mouse with no observable untoward effects illustrating the lack of toxicity for the prodrug form whereas injection of 1.04 uMoles of Compound 1101 caused immediate death in three out of three mice. Additionally, 250 uL of this 32.5 mM solution of compound A040-70 was administered to a nude mouse by oral gavage. After 5, 15, and 30 minutes 40 uL of mouse blood was obtained and analyzed by LC-MS (after extraction using acetonitrile) to demonstrate that combined blood levels of prodrug A040-70 and compound 1 were 1.8, 4.97, and 4.80 micromolar at the respective time points. This result demonstrates oral bioavailability of the active drug from the prodrug in vivo. The chloride salt is obtained by dissolving this compound A040-70 in a minimum amount of water and passing through an anion exchange resin bed such as Dowex 22 (chloride form) available from Aldrich and then washing with water and freeze-dry the combined eluant to give a solid possessing a chloride ion exchanged for the bromide ion.

EXAMPLE 62
Preparation of a Polyoxyethylene-bearing Prodrug for Nonionic Water Solubility

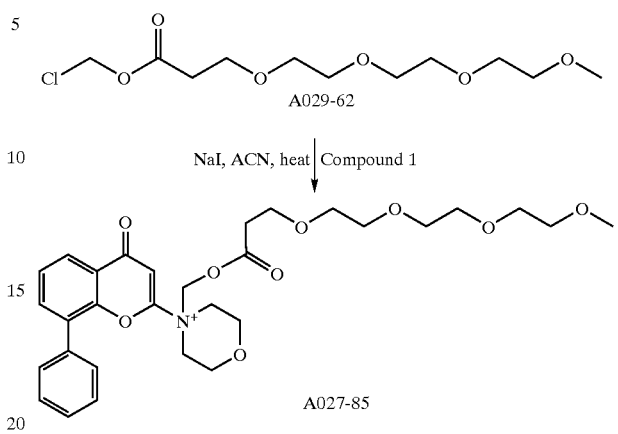

A 78 mg portion of compound 1 was dissolved in 2 mL of acetonitrile along with 76 mg of NaI and treated all at once with 144 mg of chloromethylester A029-62 and stirred at 65° C. for 5 hours. The reaction was purified by reverse phase LC-MS to give 72 mg (51% yield) of yellow solid A027-85 with a retention time of 2.30 minutes and characterized by having a mass spectrum showing M+=556 as expected for $C_{30}H_{38}NO9$. A small sample was introduced into phosphate buffer at pH=7.4 followed by LC-MS over time whereupon a substantial portion of the prodrug converted back to compound 1 with an estimated half-life of conversion of about 3 hours.

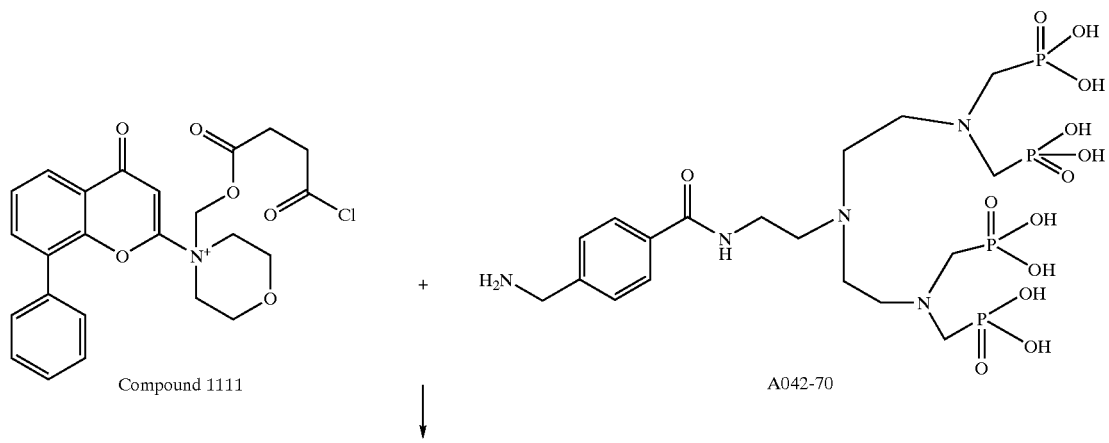

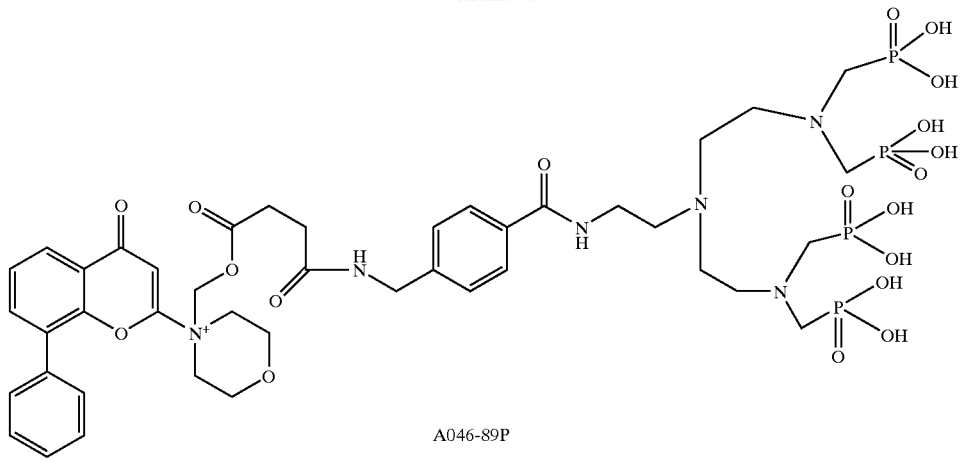

A046-89P

EXAMPLE 63

Preparation of a Bone Targeted Prodrug of Compound 1

A 20 uL portion of 75 mMolar A042-70 (1.5 uMoles) in water was added to a vial containing 500 mMolar phosphate buffer (11 vials at 11 different pHs ranging from 3.0 to 8.0 in 0.5 unit increments). After mixing each vial was then treated with 50 uL of 60 uMolar Compound 1111 in acetonitrile (3.0 uMoles=2 equivalents relative to amino group of bone targeting agent) and mixed by shaking. After one hour a 3 uL aliquot of each vial was injected on HPLC and the UV peak area determined for starting material and desired product and by product of aqueous hydrolysis, Compound 1101. Only the samples at pH of 6, 6.5, 7, 7.5 and 8 were found to have significant amounts of desired bone targeted prodrug A046-89P (retention time 2.50 minutes; [M+] found for 1075 m/z C42H59N6O19P4) [M+2]/2=538 m/z also found). This example demonstrates that the optimum pH for synthesis of bone targeted prodrug under these condition is pH=7.0 which gave about 42% of theoretical yield of the desired bone targeted prodrug of compound 1 possessing 4 phosphonic acid groups. After 24 hours analysis of this same solution standing for that time at pH=7.0 indicated that the targeted prodrug had converted completely back to compound 1 demonstratrating reversibility under physiologically relevant conditions.

EXAMPLE 64

In Vivo Efficacy of Compound 1126 Against Non-Small Cell Lung Cancer

Male nude mice of 4–6 weeks in age weighing around 30 grams were inoculated subcutaneously in the right flank with 5 million tumor cells (human non-small cell lung cancer cells: H1299) on day 0. After 14 days of allowing the tumors to grow the animals were divided into 3 groups of 5 animals each. One group received vehicle control alone. One group received twice-per-day tail vein injections (i.v) of 50 uL volume of 24.4 millimolar solution of Compound 1126 in phosphate buffered saline corresponding to 25 mg/kg/day dosing level of the active component of the prodrug (i.e. compound 1). The last group received twice-per-day tail vein injections (i.v) of 50 uL volume of 4.9 millimolar solution of Compound 1126 in phosphate buffered saline corresponding to 5 mg/kg/day dosing level of the active component of the prodrug (compound 1). The tumors were measured every three days using calipers to determine the tumor volume and the animals weights were recorded when the animals were sacrificed on day 27. The results are shown in Table 7 and indicate strong tumor volume reduction versus control for both dose levels at the first datapoint only 3 days after treatment (Day 17) and continuing through to the end of the study:

TABLE 7

|  | % Tumor Volume Reduction* Using Compound 1126 at 25 mg/kg/day | % Tumor Volume Reduction* Using Compound 1126 at 5 mg/kg/day |
| --- | --- | --- |
| Day 0 | — | — |
| Day 17 | 35% | 29% |
| Day 20 | 66% | 50% |
| Day 24 | 68% | 44% |
| Day 27 | 68% | 35% |

*Compared to the vehicle only control animals

The twice per day doses were well tolerated over the two week administration period. The efficacy results above were also accompanied by a lack of statistically significant difference in the animal body weights between the control group and the two treatment groups which as a general measure of gross toxicity indicated the targeted prodrug has a desirable lack of toxicity.

EXAMPLE 65

In Vivo Efficacy of Compound 1126 Against Brain Cancer

An animal study was run as described in Example above except using a human brain cancer cell line (U87MG) and with treatment starting on day 7 such that the first tumor volume measurement occurred on day 10. The results of Compound 1126 against this cancer cell line are shown in Table 8 and indicated effectiveness and a desirable lack of toxicity:

TABLE 8

| | % Tumor Volume Reduction*<br>Using Compound 1126 at<br>25 mg/kg/day<br>In U87MG xenograft model |
|---|---|
| Day 0 | — |
| Day 10 | 20.2% |
| Day 14 | 52.6% |
| Day 17 | 38.5% |
| Day 21 | 35.2% |

*Compared to the vehicle only control animals

EXAMPLE 66

Alpha v Targeted PI 3 Kinase Inhibitors Abrogated the Tube Formation of EDC-CBF1 Endothelial Cells on Matrigel Tube formation represents to some extent the formation of angiogenesis in vivo. In this example it was determined to what degree PI 3 kinase inhibitors (including targeted P13 kinase inhibitor prodrugs) could inhibit tube formation. Matrigel was plated into 12-well plate wells and solidified in 37° C. for 2 hours. 1×10$^5$ EDC-CBF1 endothelial cells were then put on the top of the Matrigel layer in the presence of PBS, RADfV (cyclic negative control peptide), RGDfv (cyclic positive control peptide), RADS (linear negative control peptide), compound 1, or Compound 1126 at 20° M concentration overnight. Pictures were then taken using a microscope. Well formed tubes can be visualized in the PBS control wells (top left panel of Figure). There was not much difference in the RGDfV-, RADFV-, or RGDS-containing wells compared with PBS control. Tube formation was significantly less in Compound 1101- and Compound 1126- containing wells.

EXAMPLE 67

Targeted PI 3 Kinase Inhibitors Induced p53 Transcriptional Activity in HBECs

This experiment tested the effect of PI 3 kinase inhibitors (Compound 1 and the targeted prodrug version of Compound 1; Compound 1126) on the induction of p53 luciferase activity. The transfection procedure was similar to that described in the literature to monitor p53 transcription. Compound 1 (6 hour exposure) induced more than two fold higher luciferase activity than the control and the targeted version of compound 1 (Compound 1126) had even better ability of inducing the p53 luciferase activity (to almost 3 fold). This induction of p53 function was demonstrated to be abrogated by the p53 inhibitor, pifithrin alpha at 20 uM concentration. Co-transfection of catalytic active Akt also inhibited the p53 function induced by these compounds. This result shows that the p53 transcription induced by P13 kinase inhibitors is downstream of Akt in the whole signaling cascade and the targeted prodrug Compound 1126 gave an enhanced induction of p53 versus the untargeted drug, Compound 1.

EXAMPLE 68

Purification of Compound 1126

Reaction mixture A044-84 (2.33 g) was weighed out into separate 0.33 g samples and dissolved immediately before preparative chromatography in 800 μl of a solution containing 1 part by volume acetonitrile, 1 part by volume water, and 1% by volume acetic acid. 400 μl of this solution was injected for each preparative chromatography run. The pump A eluant was B&J water (365-4) with 0.1% acetic acid added, and the pump B eluant was B&J acetonitrile (015-4) with 0.1% acetic acid added. Initially, the eluant was 10% B, then linearly ramped to 34% B over a 4 minute period, then linearly ramped to 95% B at 4.25 minutes and held there until 5.25 minutes, then linearly ramped back to the starting concentration of 10% B at 5.50 minutes. The total pump flow was 20 mL/minute. Re-equilibration of the system was accomplished while the autosampler was sampling for the next run. Using this gradient, the product with positive mass spectral peaks at 853 (m/z=1) and 427 (m/z=2) eluted at 3.37 minutes. Fractions were collected during the preparative chromatography runs when the signal detected at the ELSD exceeded 10 mv. Fractions containing product were diluted with a two-fold excess of water (by volume) and frozen in a lyophilization vessel using a dry ice-acetone bath immediately after collection. After lyophilization over a 24–48 hour period a total of 180 mg of Compound 1126 as a white fluffy solid with a purity of 95% was obtained. This example demonstrates that with careful pH control the labile prodrug Compound 1126 can be isolated in high purity using aqueous based reverse phase separation methods.

EXAMPLE 69

Preparation of SCN-reactive Prodrug

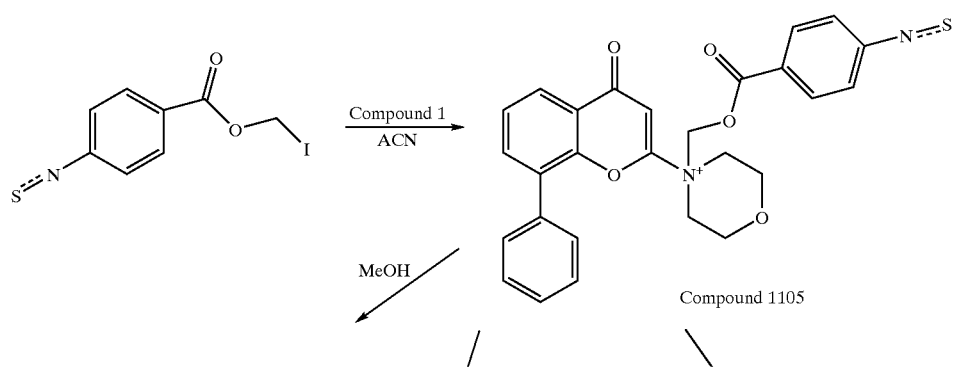

-continued

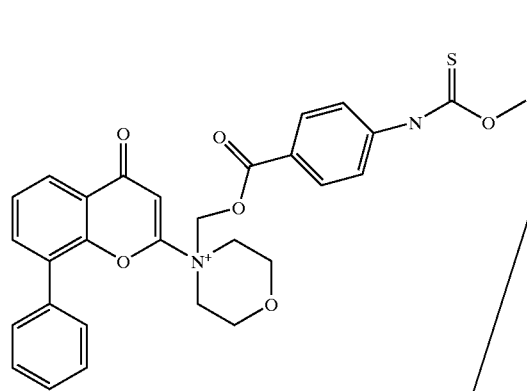

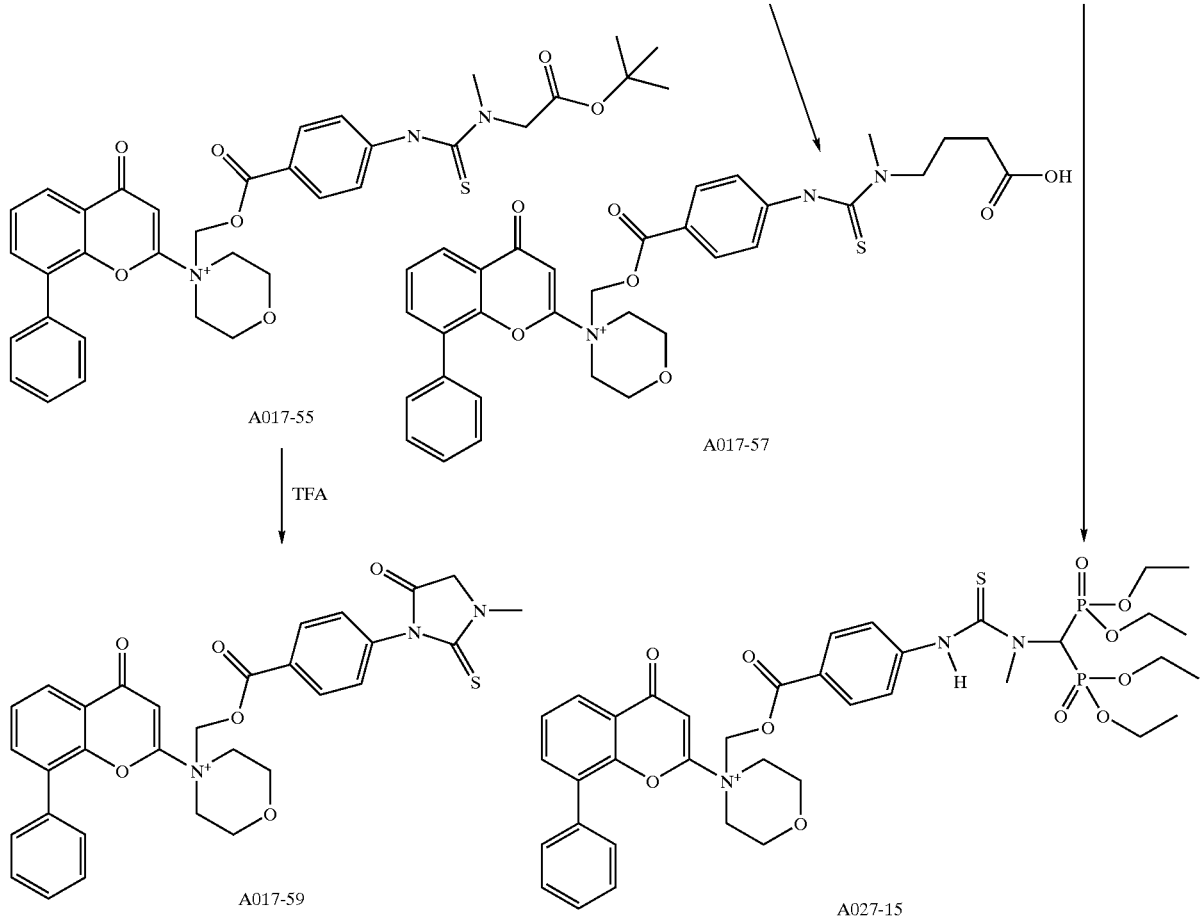

A 184 mg portion of A014-48 prepared by the method of Example 20 was dissolved with 154 mg of Compound 1 in 12 mL of acetonitrile and stirred at room temperature. After 16 hours LC-MS indicated about 65% conversion to the desired quat compound so an addition 45 mg of the iodo compound was added and after an additional 22 hours the reaction had gone to 80% completion so an additional 40 mg of iodo compound was added and allowed to stir and additional 24 hours. The solids were then centrifuged and wash with acetonitrile to give 282.6 mg (45% yield) of the desired product in high purity characterized by a retention time of 2.89 minutes and showing the desired M+ of 499 for C28H23N2O5S as compound COMPOUND 1105.

Upon standing in methanol compound 1105, reacts cleanly with methanol to give compound A013-94 with a retention time of 2.78 minutes and the expected M+ of 531 for C29H27N2O6S. This illustrates the reaction of the isothiocyanato prodrug with an alcohol to give a carbamate conjugation to the linker.

The isothiocyanate intermediate prodrug was also reacted with various amines in methylene chloride (optionally in the presence of triethylamine) including secondary amines to give urea products such as A017-55 (retention time 2.84 minutes showing the desired M+of 644 m/z for C35H38N3O7S); A017-57 (retention time 2.46 minutes showing the desired M+ of 616 m/z for C33H34N3O7S); and A027-15 ((retention time 2.82 minutes showing the desired M+ of. 816 m/z for C38H48N3O11P2S. These examples demonstrate reaction in good yield of the isothiocyanate prodrug with a diverse group of nucleophiles to give the desired linked products. The A017-55 compound was further reacted with trifluoroacetic acid which surprisingly gave the cyclic compound A017-59 during the course of cleaving the t-butyl group (retention time 2.47 minutes showing the desired M+ of 570 m/z for C31H28N3O6S). This example demonstrated additional chemistry can be performed on the linker group of the prodrug compounds. In phosphate buffer at pH=7.4 significant amounts of this compound converted back to compound 1 over a 17 hour period, followed by LC-MS.

EXAMPLE 70

Acute Toxicity of Compound 1 versus Targeted Prodrug

Intravenously administered Compound 1 was determined to have a 100% mortality within 5 minutes of administration in three nude mice at a dose level of 16 mg/kg. Compound 1126, prepared by the method of Example 56, when injected intravenously at 37% higher dose level (22 mg/kg) in three nude mice showed 0% mortality even after 1 hour of observation. This example demonstrates the improved formulation ability of the prodrugs and the diminished toxicity of the prodrugs of Compound 1.

EXAMPLE 71

Analog of Compound 1

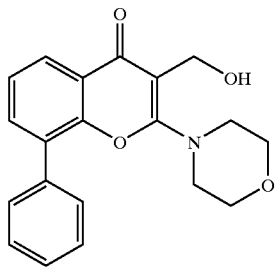

A037-94

During the preparation of the intermediate A046-67SM such as described for Compound 1126 in Example 56 a side product was observed. This material was purified by LC-MS to give a single compound, A037-94, consistent by proton NMR with the proposed structure and giving a retention time of 3.00 minutes and a mass spectrum showing the expected [M+H]+ of 338 m/z (very low abundance) and more prominent mass [M+H+41(ACN)] at 379 m/z. This example demonstrates the isolation of a novel analog of compound 1 suitable for additional prodrug modification.

EXAMPLE 72

Use of Prodrug to Deliver Compound 1 in Mice

Mice were injected with a million non-small cell lung cancer cells (H1299) subcutaneously and allowed to grow about 7 days until the tumor mass was approximately 10 to 15 mm by 7 to 9 mm in dimensions. Animals were injected with the targeted prodrug, Compound 1126, either i.v. (50 uL) or i.p. (50 uL) with 32.6 mMolar solutions of Compound 1126 in phosphate buffered saline. After 60 minutes the mice were sacrificed and the tumors removed. Three small pieces of the tumors were retrieved and minced. After aging for 24 hours to allow all of the prodrug to convert to compound 1 the tumor samples were extracted with acetonitrile. Quantitation by LC-MS indicated that the concentration of extractable compound 1 (as the sum of free compound 1 and derived from Compound 1126) was 157±7 nanomolar in the tumor pieces for the I.P. injection and 271±17 nanomolar in the tumor pieces for the I.V. injection. This example demonstrates the delivery of Compound 1 to tumor tissue using a targeted prodrug.

EXAMPLE 73

Reversibility of Prodrugs to form Compound 1

Prodrug Compounds were dissolved in water or in DMSO (if not freely soluble in water) and then diluted at least 10-fold into 50 mM phosphate buffer at pH=7.4 or pH=4.8 and allowed to stand at room temperature. The final concentration of the compounds in aqueous environment ranged from 50 to 500 uMolar. Aliquots over time were taken and analyzed by LC-MS to determine both disappearance of prodrug and confirm appearance of drug (compound 1). Compound 1126 was found to have a half-life of about 1 hour at pH=7.5 and a half-life of about 64 hours at pH=4.8. Compound 1110 was found to have a half-life of about 10 hours at pH=7.4 and greater than 120 hours at pH=4.8. Compound A040-70 was found to have a half-life of about 10 hours at pH=7.4. These examples demonstrate that chemically the prodrugs converted to drug (compound 1) and the disappearance of the prodrug is very pH dependant with conversion taking place much faster at physiological pH and substantially slower at acidic pH.

EXAMPLE 74

Synthesis of Tumor Localizing Conjugate

The electrophilic group-bearing compounds (such as compound A036-48B, 1105, 1107, 1111, A024-79, and 1113) can be reacted with polymers bearing nucleohilic groups such as alcohols, amino, and thiol groups. N-(2-hyroxypropyl)methylacrylamide (HPMA) having molecular weight of 2000 to 100,000 is reacted with excess compound 1111 in a nonprotic organic solvent such as methylene chloride or tetrahydrofuran in the presensce of triethyl amine or diisopropylethyl amine and then separated by size exclusion chromatography, ultracentrifugation, or precipitation in another solvent such as methanol or ether. The polymer thus precipitated or separated is substantially free of 1111 and is used as a tumor localizing conjugate that releases active compound 1 overtime in the vicinity of the tumor resulting in antitumor and anti-angiogenic effects. Likewise polyglutamic acids can be converted to poly-nucleophilic bearing groups by reaction of the carboxylic acids with excess diamines using carbodiimide coupling followed by size exclusion chromatography or reverse phase HPLC purification to obtain poly-nucleophilic versions of polyglutamic acids. These polymers can then be reacted directly with excess portions of compounds 1111 or 1105 or A036-48B or A024-79 in an aprotic organic solvent such as methylene chloride or tetrahydrofuran in the presensce of triethyl amine or diisopropylethyl amine and then separated by size exclusion chromatography, ultracentrifugation, or precipitation in another solvent such as methanol or ether. The polyconjugated polymer thus precipitated or separated is substantially free of low molecular weight residual prodrug and is used as a tumor localizing conjugate that releases active compound 1 overtime in the vicinity of the tumor resulting in antitumor and anti-angiogenic effects.

What is claimed is:
1. A compound of the formula:

wherein,
Ring A is benzo;
$Z_1$ and $Z_2$ are O;
$R_1$ and $R_2$ independently are H, optionally substituted aliphatic, optionally substituted aryl, hydroxyl, halogen, alkoxy, heterocycle, cyano, amino, or, are taken together to form an optionally substituted cycloaliphatic or optionally substituted aryl;
$R_3$ represents H, optionally substituted aliphatic, and optionally substituted aryl;
$R_4$ and $R_5$ independently are H, optionally substituted aliphatic, optionally substituted aryl, heterocycle, aryloxy, carboxy, or, are taken together to form an optionally substituted heterocycle or optionally substituted heteroaryl;
$R_6$ represents H, optionally substituted aliphatic, optionally substituted aryl, alkoxy, carboxy, amino, heterocycle, aryloxy, and optionally substituted therewith a targeting agent;
L represents a linker group; and
the bond between $N^+$ and L is hydrolyzable.

2. The compound of claim 1, wherein $R_4$ and $R_5$ independently are optionally substituted aliphatic, optionally substituted aryl, heterocycle, aryloxy, carboxy, or, are taken together to form an optionally substituted heterocycle or optionally substituted heteroaryl.

3. The compound of claim 2, wherein $R_1$-Ring A-$R_2$ is selected from the group consisting of:

101
-continued
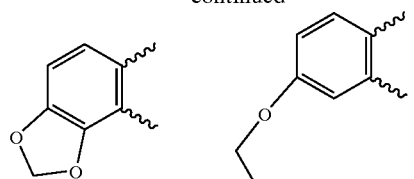 and
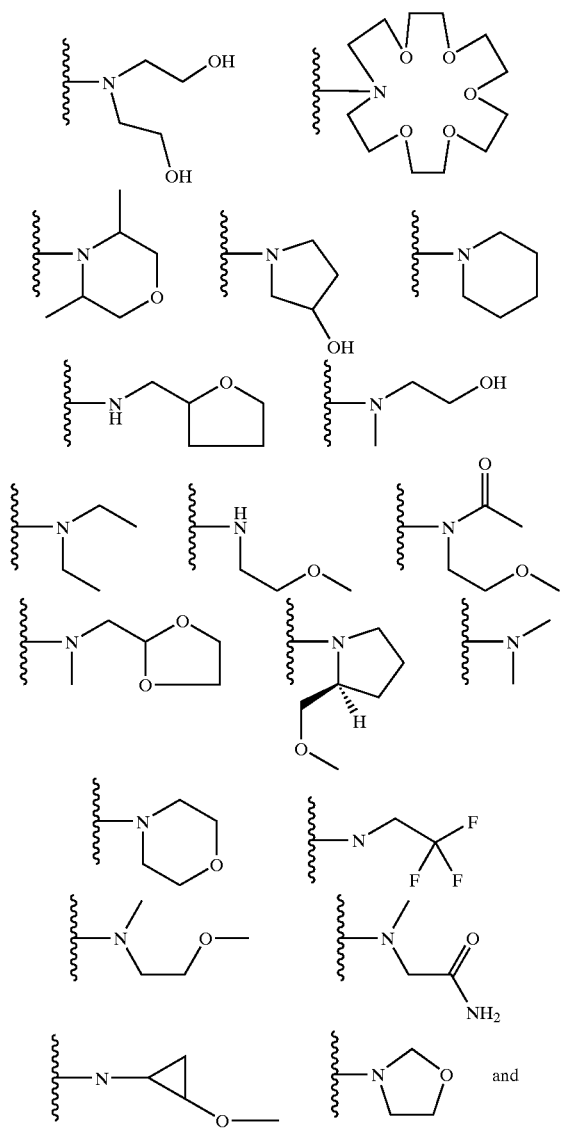
4. The compound of claim 2, wherein R₄—N—R₅ is selected from the group consisting of:
102
-continued
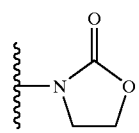
5. The compound of claim 2, wherein R₆ is selected from the group consisting of:
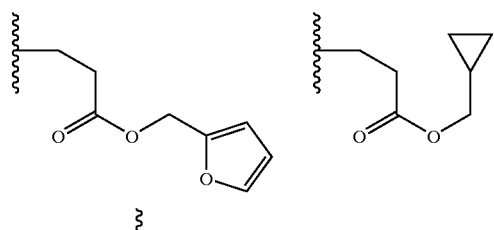
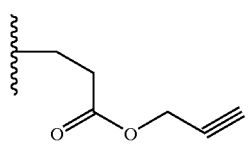
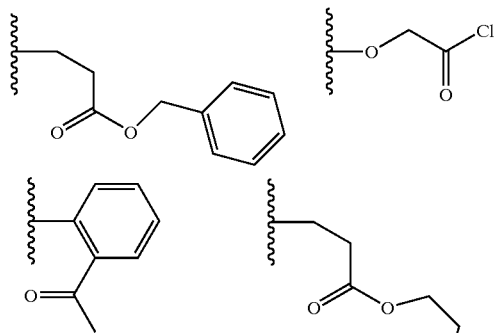
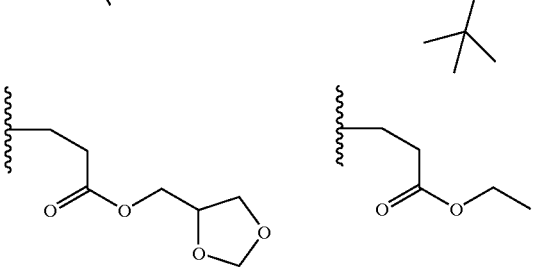
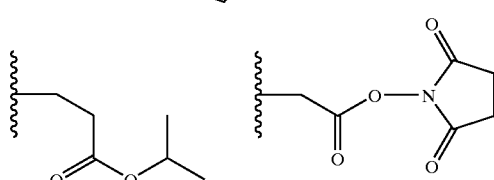
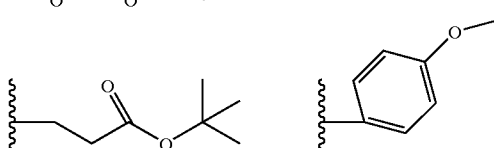
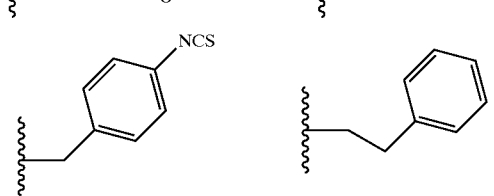

103
-continued
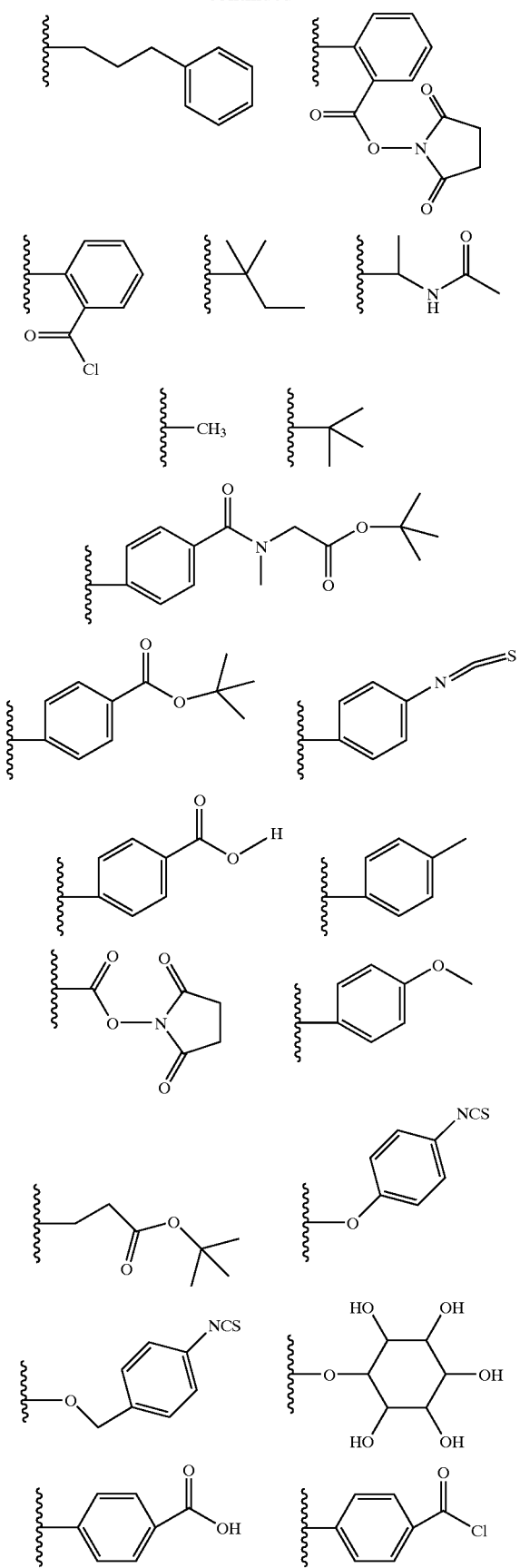
104
-continued
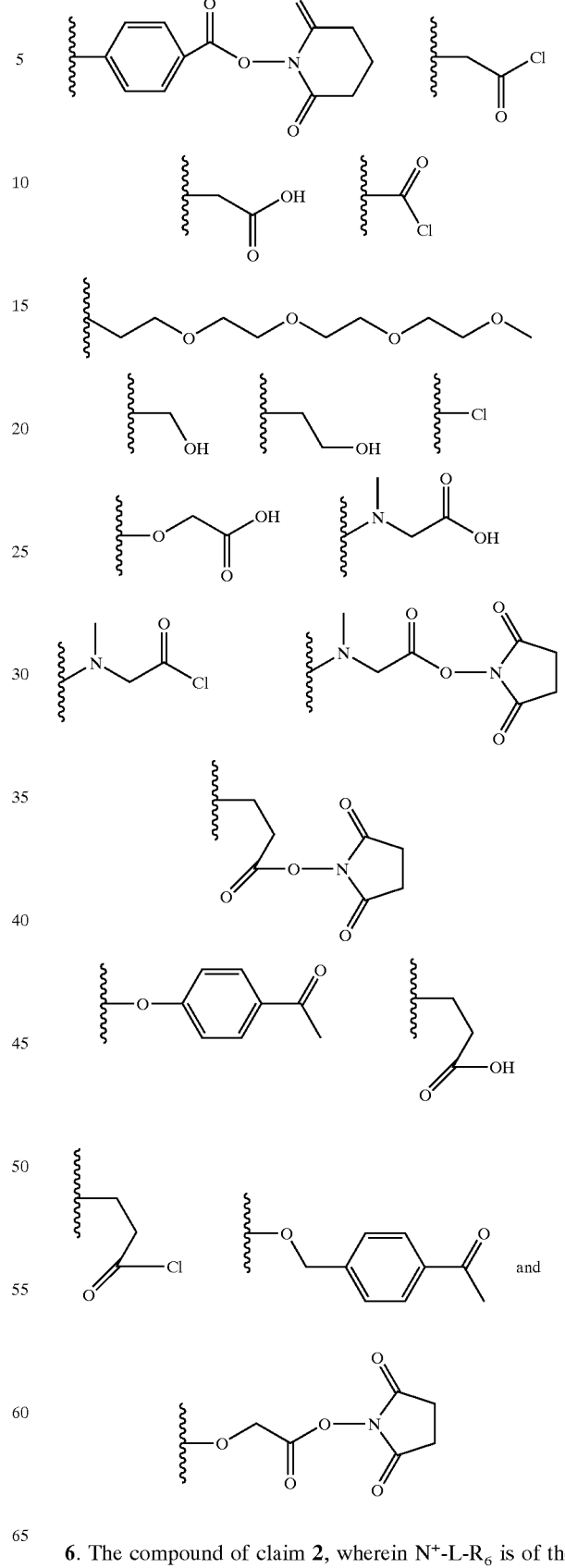
6. The compound of claim 2, wherein $N^+$-L-$R_6$ is of the formula:

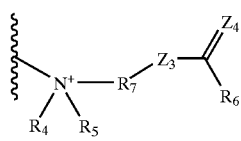

wherein, $Z_3$ and $Z_4$ independently are S or O; and $R_7$ represents —$CH_2$—, —$CH(CH_3)$—, —$CH(Ph)$-, —$C(CH3)(COOH)$— or $CH(CH(CH3)2)$—.

7. The compound of claim 6, wherein the bond between $R_7$ and the quaternary amine is hydrolyzable.

8. The compound of claim 6, wherein $R_6$ is substituted with a targeting agent and is of the formula:

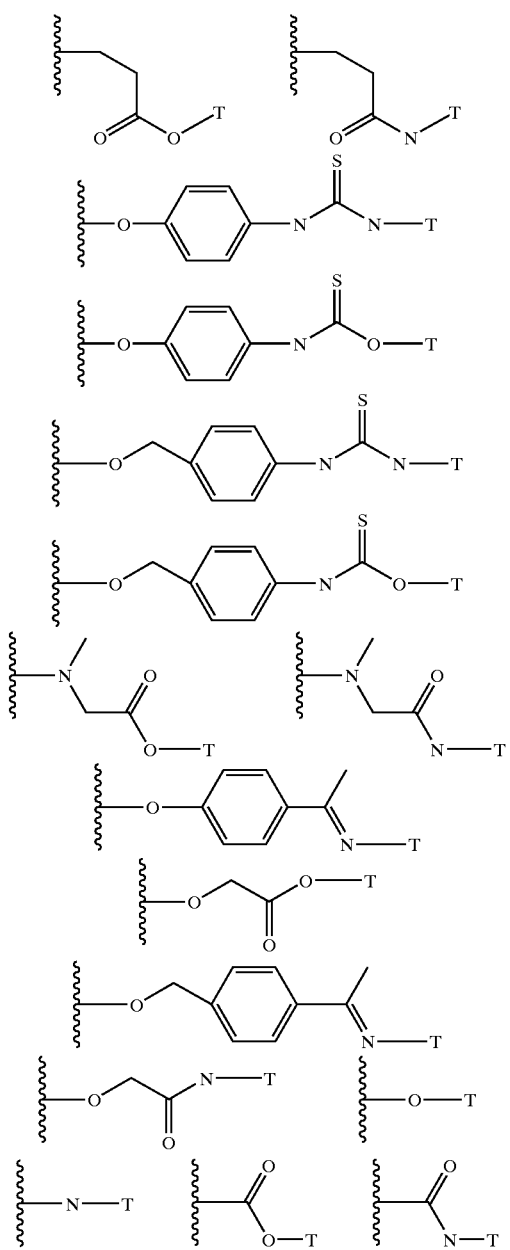

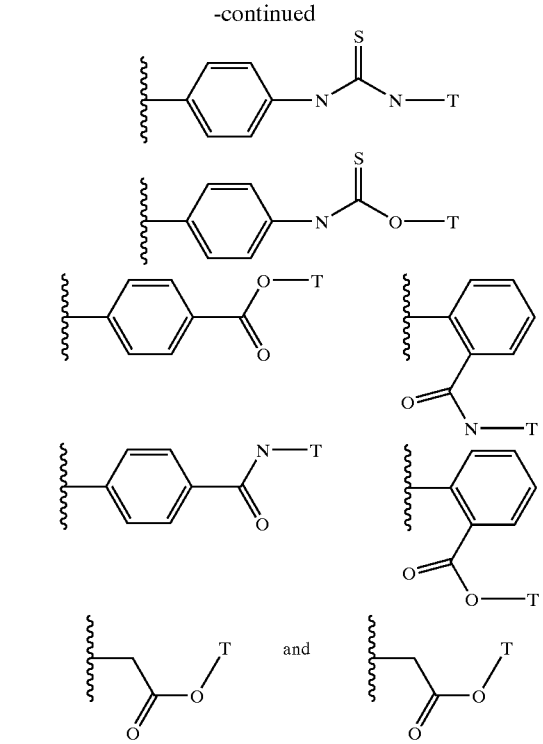

wherein, T is a targeting agent.

9. The compound of claim 8, wherein the targeting agent is selected from the group consisting of vitamins, peptides, proteins, liposomes, bone-seeking agents, and cartilage-seeking agents.

10. The compound of claim 9, wherein the vitamin is folate or vitamin C.

11. The compound of claim 9, wherein the peptide is an RGD-containing peptide selected from the group consisting of RGDs, c(RGDfK), vitronectin, fibronectin, somatostatin-receptor agonists and somatostatin-receptor antagonists.

12. The compound of claim 9, wherein the protein is a tumor-specific monoclonal antibody or fragment thereof.

13. The compound of claim 9, wherein the bone-seeking agent is selected from the group consisting of a phosphonate, phosphonic acid, aminomethylphosphonic acid, phosphate, polyphosphate, and hydroxyapatite-binding polypeptides.

14. The compound of claim 13, wherein the bone-seeking agent is EDTMP, DOTMP, ABDTMP, BAD, MTX-BP, CF—BP, $(Asp)_6$, $(Glu)_6$, alendronate, pamidronate, 4-aminobutylphosphonic acid, 1-hydroxyethane-1,1-diphosphonic acid, aminomethylenebisphosphonic acid, phytic acid, and N,N-bis(methylphosphono)-4-aminobenzoic acid.

15. A compound of the formula:

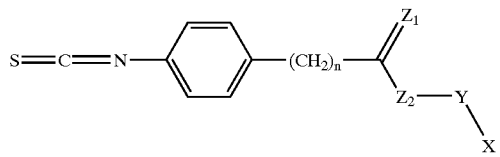

wherein,

X represents a halo group;

Y represents —$CH_2$—, —$CH(CH_3)$—, —$CH(Ph)$-, —$C(CH3)(COOH)$— or $CH(CH(CH3)_2)$—;

$Z_1$ and $Z_2$ independently are S or O; and
n=0 to 1.

16. The compound of claim 15, wherein,

X represents Cl or I;

Y represents —$CH_2$—, —$CH(CH_3)$—, —CH(Ph)-, —C(CH3)(COOH)— or $CH(CH(CH3)_2)$-

$Z_1$ and $Z_2$ are each O; and
n=0.

17. The compound of claim 15, wherein,

X represents Cl or I;

$Z_1$ and $Z_2$ are each O; and
n=1.

18. A method of purifying a compound according to claim 2, comprising:

(a) adding a composition comprising said compound to a solution, wherein said solution comprises at least 0.1% by (v/v) of an acid;

(b) adding the solution of (a) comprising said compound to a chromatography system; and (c) isolating said compound.

19. The method of claim 18 wherein said chromatography system is HPLC.

20. The compound of claim 2, wherein the compound is of the formula:

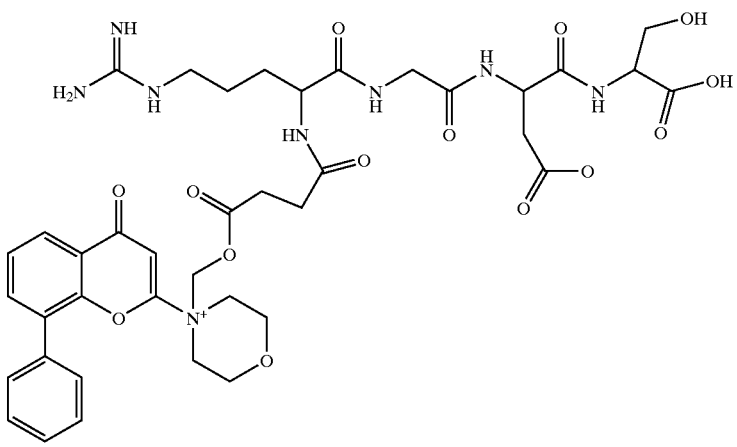

and pharmaceutically acceptable salts thereof.

* * * * *